United States Patent
Penner et al.

(10) Patent No.: US 8,303,643 B2
(45) Date of Patent: Nov. 6, 2012

(54) METHOD AND DEVICE FOR ELECTROCHEMICAL FORMATION OF THERAPEUTIC SPECIES IN VIVO

(75) Inventors: Avi Penner, Tel Aviv (IL); Eilezer Gileadi, Herzliya Pituach (IL)

(73) Assignee: Remon Medical Technologies Ltd., Arlington, VA (US)

( * ) Notice: Subject to any disclaimer, the term of this patent is extended or adjusted under 35 U.S.C. 154(b) by 340 days.

(21) Appl. No.: 12/784,708

(22) Filed: May 21, 2010

(65) Prior Publication Data

US 2010/0233237 A1    Sep. 16, 2010

Related U.S. Application Data

(62) Division of application No. 10/477,514, filed on Nov. 19, 2003, now Pat. No. 7,727,221.

(51) Int. Cl.
*A61F 2/06* (2006.01)

(52) U.S. Cl. .................... 623/1.15; 623/1.46; 604/890.1

(58) Field of Classification Search ............... 607/2, 50, 607/75; 623/1.15, 1.42, 1.46; 604/890.1
See application file for complete search history.

(56) References Cited

U.S. PATENT DOCUMENTS

| | | |
|---|---|---|
| 2,950,187 A | 8/1960 | Ototani |
| 3,560,362 A | 2/1971 | Kasamatsu et al. |
| 3,569,660 A | 3/1971 | Houldcroft |
| 3,687,135 A | 8/1972 | Stroganov et al. |
| 3,758,396 A | 9/1973 | Vieth et al. |
| 3,868,578 A | 2/1975 | Oldham |
| 3,910,819 A | 10/1975 | Rembaum et al. |
| 3,948,254 A | 4/1976 | Zaffaroni |
| 3,952,334 A | 4/1976 | Bokros et al. |
| 3,993,072 A | 11/1976 | Zaffaroni |
| 4,002,877 A | 1/1977 | Banas |
| 4,101,984 A | 7/1978 | MacGregor |
| 4,143,661 A | 3/1979 | LaForge et al. |
| 4,202,055 A | 5/1980 | Reiner et al. |
| 4,237,559 A | 12/1980 | Borom |
| 4,308,868 A | 1/1982 | Jhabvala |
| 4,334,327 A | 6/1982 | Lyman et al. |
| 4,401,546 A | 8/1983 | Nakamura et al. |
| 4,532,929 A | 8/1985 | Mattei et al. |
| 4,539,061 A | 9/1985 | Sagiv |
| 4,542,539 A | 9/1985 | Rowe, Jr. et al. |
| 4,585,652 A | 4/1986 | Miller et al. |
| 4,634,502 A | 1/1987 | Callahan et al. |

(Continued)

FOREIGN PATENT DOCUMENTS

AU    739 507    11/1998

(Continued)

OTHER PUBLICATIONS

Macias et al., "Electrospun mesoporous metal oxide fibers," *Microporous and Mesoporous Materials*, 2005, 86: 1-13.

(Continued)

*Primary Examiner* — Mark W Bockelman
(74) *Attorney, Agent, or Firm* — Fish & Richardson P.C.

(57) ABSTRACT

A device and method are provided for spontaneous electrochemical production of therapeutic species, in vivo. An active metal is implanted in the tissue. The metal undergoes corrosion, thus acting as a reducing agent to constituents in the tissue, so as to cause these constituents to form the therapeutic agents.

19 Claims, 8 Drawing Sheets

U.S. PATENT DOCUMENTS

| | | |
|---|---|---|
| 4,655,771 A | 4/1987 | Wallsten |
| 4,657,544 A | 4/1987 | Pinchuk |
| 4,665,896 A | 5/1987 | LaForge et al. |
| 4,705,502 A | 11/1987 | Patel |
| 4,713,070 A | 12/1987 | Mano |
| 4,725,273 A | 2/1988 | Kira |
| 4,733,665 A | 3/1988 | Palmaz |
| 4,767,418 A | 8/1988 | Deininger et al. |
| 4,784,659 A | 11/1988 | Fleckenstein et al. |
| 4,800,882 A | 1/1989 | Gianturco |
| 4,804,382 A | 2/1989 | Turina et al. |
| 4,886,062 A | 12/1989 | Wiktor |
| 4,954,126 A | 9/1990 | Wallsten |
| 4,976,692 A | 12/1990 | Atad |
| 4,994,071 A | 2/1991 | MacGregor |
| 5,024,671 A | 6/1991 | Tu et al. |
| 5,059,211 A | 10/1991 | Stack et al. |
| 5,061,275 A | 10/1991 | Wallsten et al. |
| 5,061,914 A | 10/1991 | Busch et al. |
| 5,073,365 A | 12/1991 | Katz et al. |
| 5,079,203 A | 1/1992 | Pinnavaia |
| 5,091,024 A | 2/1992 | DeBold et al. |
| 5,091,205 A | 2/1992 | Fan |
| 5,102,403 A | 4/1992 | Alt |
| 5,120,322 A | 6/1992 | Davis et al. |
| 5,125,971 A | 6/1992 | Nonami et al. |
| 5,147,370 A | 9/1992 | McNamara et al. |
| 5,163,958 A | 11/1992 | Pinchuk |
| 5,195,969 A | 3/1993 | Wang et al. |
| 5,205,921 A | 4/1993 | Shirkanzadeh |
| 5,234,457 A | 8/1993 | Andersen |
| 5,236,413 A | 8/1993 | Feiring |
| 5,236,447 A | 8/1993 | Kubo et al. |
| 5,270,086 A | 12/1993 | Hamlin |
| 5,279,292 A | 1/1994 | Baumann et al. |
| 5,290,585 A | 3/1994 | Elton |
| 5,292,558 A | 3/1994 | Heller et al. |
| 5,302,414 A | 4/1994 | Alkhimov et al. |
| 5,304,121 A | 4/1994 | Sahatjian |
| 5,304,195 A | 4/1994 | Twyford, Jr. et al. |
| 5,306,286 A | 4/1994 | Stack et al. |
| 5,314,453 A | 5/1994 | Jeutter |
| 5,322,520 A | 6/1994 | Milder |
| 5,342,348 A | 8/1994 | Kaplan |
| 5,348,553 A | 9/1994 | Whitney |
| 5,356,433 A | 10/1994 | Rowland et al. |
| 5,360,440 A | 11/1994 | Andersen |
| 5,366,504 A | 11/1994 | Andersen et al. |
| 5,380,298 A | 1/1995 | Zabetakis et al. |
| 5,383,935 A | 1/1995 | Shirkhanzadeh |
| 5,385,776 A | 1/1995 | Maxfield et al. |
| 5,397,307 A | 3/1995 | Goodin |
| 5,405,367 A | 4/1995 | Schulman et al. |
| 5,421,955 A | 6/1995 | Lau et al. |
| 5,439,446 A | 8/1995 | Barry |
| 5,443,458 A | 8/1995 | Eury |
| 5,443,496 A | 8/1995 | Schwartz et al. |
| 5,443,500 A | 8/1995 | Sigwart |
| 5,449,373 A | 9/1995 | Pinchasik et al. |
| 5,449,382 A | 9/1995 | Dayton |
| 5,458,627 A | 10/1995 | Baranowski, Jr. et al. |
| 5,462,575 A | 10/1995 | Del Corso |
| 5,464,450 A | 11/1995 | Buscemi et al. |
| 5,464,650 A | 11/1995 | Berg et al. |
| 5,468,574 A | 11/1995 | Ehrenberg et al. |
| 5,474,797 A | 12/1995 | Sioshansi et al. |
| 5,500,013 A | 3/1996 | Buscemi et al. |
| 5,514,154 A | 5/1996 | Lau et al. |
| 5,527,337 A | 6/1996 | Stack et al. |
| 5,536,573 A | 7/1996 | Rubner et al. |
| 5,545,208 A | 8/1996 | Wolff et al. |
| 5,549,664 A | 8/1996 | Hirata et al. |
| 5,551,954 A | 9/1996 | Buscemi et al. |
| 5,578,075 A | 11/1996 | Dayton |
| 5,587,200 A | 12/1996 | Lorenz et al. |
| 5,587,507 A | 12/1996 | Kohn et al. |
| 5,591,222 A | 1/1997 | Susawa et al. |
| 5,591,224 A | 1/1997 | Schwartz et al. |
| 5,599,352 A | 2/1997 | Dinh et al. |
| 5,603,556 A | 2/1997 | Klink |
| 5,605,696 A | 2/1997 | Eury et al. |
| 5,607,463 A | 3/1997 | Schwartz et al. |
| 5,609,629 A | 3/1997 | Fearnot et al. |
| 5,614,549 A | 3/1997 | Greenwald et al. |
| 5,624,411 A | 4/1997 | Tuch |
| 5,628,787 A | 5/1997 | Mayer |
| 5,629,077 A | 5/1997 | Turnlund et al. |
| 5,632,771 A | 5/1997 | Boatman et al. |
| 5,632,840 A | 5/1997 | Campbell |
| 5,649,951 A | 7/1997 | Davidson |
| 5,658,327 A | 8/1997 | Altman et al. |
| 5,674,192 A | 10/1997 | Sahatjian et al. |
| 5,674,242 A | 10/1997 | Phan |
| 5,676,685 A | 10/1997 | Razavi |
| 5,679,440 A | 10/1997 | Kubota |
| 5,690,670 A | 11/1997 | Davidson |
| 5,693,085 A | 12/1997 | Buirge et al. |
| 5,693,928 A | 12/1997 | Egitto et al. |
| 5,697,967 A | 12/1997 | Dinh et al. |
| 5,700,286 A | 12/1997 | Tartaglia et al. |
| 5,716,981 A | 2/1998 | Hunter et al. |
| 5,721,049 A | 2/1998 | Marcolongo et al. |
| 5,725,570 A | 3/1998 | Heath |
| 5,733,925 A | 3/1998 | Kunz et al. |
| 5,741,331 A | 4/1998 | Pinchuk |
| 5,744,515 A | 4/1998 | Clapper |
| 5,749,809 A | 5/1998 | Lin |
| 5,749,880 A | 5/1998 | Banas et al. |
| 5,758,562 A | 6/1998 | Thompson |
| 5,759,192 A | 6/1998 | Saunders |
| 5,761,775 A | 6/1998 | Legome et al. |
| 5,769,883 A | 6/1998 | Buscemi et al. |
| 5,769,884 A | 6/1998 | Solovay |
| 5,773,925 A | 6/1998 | Kimura et al. |
| 5,776,184 A | 7/1998 | Tuch |
| 5,779,904 A | 7/1998 | Ruderman et al. |
| 5,780,807 A | 7/1998 | Saunders |
| 5,788,626 A | 8/1998 | Thompson |
| 5,788,687 A | 8/1998 | Batich et al. |
| 5,788,979 A | 8/1998 | Alt et al. |
| 5,797,898 A | 8/1998 | Santini, Jr. et al. |
| 5,800,511 A | 9/1998 | Mayer |
| 5,815,904 A | 10/1998 | Clubb et al. |
| 5,817,046 A | 10/1998 | Glickman |
| 5,824,045 A | 10/1998 | Alt |
| 5,824,048 A | 10/1998 | Tuch |
| 5,824,077 A | 10/1998 | Mayer |
| 5,830,217 A | 11/1998 | Ryan |
| 5,833,715 A | 11/1998 | Vachon et al. |
| 5,837,007 A | 11/1998 | Altman et al. |
| 5,837,275 A | 11/1998 | Burrell et al. |
| 5,840,387 A | 11/1998 | Berlowitz-Tarrant et al. |
| 5,843,089 A | 12/1998 | Sahatjian et al. |
| 5,843,172 A | 12/1998 | Yan |
| 5,852,277 A | 12/1998 | Gustafson |
| 5,854,382 A | 12/1998 | Loomis |
| 5,858,556 A | 1/1999 | Eckert et al. |
| 5,869,140 A | 2/1999 | Blohowiak et al. |
| 5,873,904 A | 2/1999 | Ragheb et al. |
| 5,876,756 A | 3/1999 | Takada et al. |
| 5,879,697 A | 3/1999 | Ding et al. |
| 5,880,661 A | 3/1999 | Davidson et al. |
| 5,882,335 A | 3/1999 | Leone et al. |
| 5,891,108 A | 4/1999 | Leone et al. |
| 5,891,191 A | 4/1999 | Stinson |
| 5,899,935 A | 5/1999 | Ding |
| 5,902,266 A | 5/1999 | Leone et al. |
| 5,906,759 A | 5/1999 | Richter |
| 5,907,893 A | 6/1999 | Zadno-Azizi et al. |
| 5,922,005 A | 7/1999 | Richter et al. |
| 5,922,021 A | 7/1999 | Jang |
| 5,928,247 A | 7/1999 | Barry et al. |
| 5,935,506 A | 8/1999 | Schmitz et al. |
| 5,938,903 A | 8/1999 | Broderick |
| 5,941,843 A | 8/1999 | Atanasoska et al. |
| 5,951,458 A | 9/1999 | Hastings et al. |
| 5,951,881 A | 9/1999 | Rogers et al. |

| Patent No. | Date | Inventor(s) |
|---|---|---|
| 5,954,706 A | 9/1999 | Sahatjian |
| 5,957,975 A | 9/1999 | Lafont et al. |
| 5,958,440 A | 9/1999 | Burrell et al. |
| 5,961,547 A | 10/1999 | Razavi |
| 5,968,091 A | 10/1999 | Pinchuk et al. |
| 5,968,092 A | 10/1999 | Buscemi et al. |
| 5,972,027 A | 10/1999 | Johnson |
| 5,972,192 A | 10/1999 | Dubin et al. |
| 5,976,169 A | 11/1999 | Imran |
| 5,976,454 A | 11/1999 | Sterzel et al. |
| 5,977,204 A | 11/1999 | Boyan et al. |
| 5,980,554 A | 11/1999 | Lenker et al. |
| 5,980,564 A | 11/1999 | Stinson |
| 5,980,566 A | 11/1999 | Alt et al. |
| 6,001,125 A | 12/1999 | Golds et al. |
| 6,013,591 A | 1/2000 | Ying et al. |
| 6,017,553 A | 1/2000 | Burrell et al. |
| 6,017,577 A | 1/2000 | Hostettler et al. |
| 6,021,347 A | 2/2000 | Herbst et al. |
| 6,025,036 A | 2/2000 | McGill et al. |
| 6,027,742 A | 2/2000 | Lee et al. |
| 6,034,295 A | 3/2000 | Rehberg et al. |
| 6,042,597 A | 3/2000 | Kveen et al. |
| 6,056,776 A | 5/2000 | Lau et al. |
| 6,063,101 A | 5/2000 | Jacobsen et al. |
| 6,071,305 A | 6/2000 | Brown et al. |
| 6,080,190 A | 6/2000 | Schwartz |
| 6,086,773 A | 7/2000 | Dufresne et al. |
| 6,096,070 A | 8/2000 | Ragheb et al. |
| 6,096,175 A | 8/2000 | Roth |
| 6,099,561 A | 8/2000 | Alt |
| 6,099,562 A | 8/2000 | Ding et al. |
| 6,106,473 A | 8/2000 | Violante et al. |
| 6,107,004 A | 8/2000 | Donadio, III |
| 6,117,592 A | 9/2000 | Hoshino et al. |
| 6,120,260 A | 9/2000 | Jirele |
| 6,120,535 A | 9/2000 | McDonald et al. |
| 6,120,660 A | 9/2000 | Chu et al. |
| 6,123,861 A | 9/2000 | Santini, Jr. et al. |
| 6,132,463 A | 10/2000 | Lee et al. |
| 6,139,573 A | 10/2000 | Sogard et al. |
| 6,139,574 A | 10/2000 | Vacanti et al. |
| 6,139,913 A | 10/2000 | Van Steenkiste et al. |
| 6,140,740 A | 10/2000 | Porat et al. |
| 6,143,370 A | 11/2000 | Panagiotou et al. |
| 6,153,252 A | 11/2000 | Hossainy et al. |
| 6,159,142 A | 12/2000 | Alt |
| 6,162,238 A | 12/2000 | Kaplan et al. |
| 6,164,284 A | 12/2000 | Schulman et al. |
| 6,165,211 A | 12/2000 | Thompson |
| 6,167,307 A | 12/2000 | Hess |
| 6,168,602 B1 | 1/2001 | Ryan |
| 6,170,488 B1 | 1/2001 | Spillman, Jr. et al. |
| 6,174,329 B1 | 1/2001 | Callol et al. |
| 6,174,330 B1 | 1/2001 | Stinson |
| 6,180,222 B1 | 1/2001 | Schulz et al. |
| 6,185,455 B1 | 2/2001 | Loeb et al. |
| 6,185,457 B1 | 2/2001 | Kroll et al. |
| 6,190,404 B1 | 2/2001 | Palmaz et al. |
| 6,192,271 B1 | 2/2001 | Hayman |
| 6,201,991 B1 | 3/2001 | Chekanov |
| 6,203,536 B1 | 3/2001 | Berg et al. |
| 6,206,914 B1 | 3/2001 | Soykan et al. |
| 6,206,915 B1 | 3/2001 | Fagan et al. |
| 6,206,916 B1 | 3/2001 | Furst |
| 6,212,434 B1 | 4/2001 | Scheiner |
| 6,214,037 B1 | 4/2001 | Mitchell et al. |
| 6,214,042 B1 | 4/2001 | Jacobsen et al. |
| 6,217,607 B1 | 4/2001 | Alt |
| 6,231,597 B1 | 5/2001 | Deem et al. |
| 6,240,616 B1 | 6/2001 | Yan |
| 6,241,762 B1 | 6/2001 | Shanley |
| 6,245,103 B1 | 6/2001 | Stinson |
| 6,245,104 B1 | 6/2001 | Alt |
| 6,249,952 B1 | 6/2001 | Ding |
| 6,251,136 B1 | 6/2001 | Guruwaiya et al. |
| 6,251,980 B1 | 6/2001 | Lan et al. |
| 6,253,252 B1 | 6/2001 | Schofield |
| 6,253,443 B1 | 7/2001 | Johnson |
| 6,254,632 B1 | 7/2001 | Wu et al. |
| 6,258,117 B1 | 7/2001 | Camrud et al. |
| 6,264,687 B1 | 7/2001 | Tomonto |
| 6,270,831 B2 | 8/2001 | Kumar et al. |
| 6,273,908 B1 | 8/2001 | Ndondo-Lay |
| 6,273,913 B1 | 8/2001 | Wright et al. |
| 6,277,078 B1 | 8/2001 | Porat et al. |
| 6,280,385 B1 | 8/2001 | Melzer et al. |
| 6,280,411 B1 | 8/2001 | Lennox |
| 6,283,386 B1 | 9/2001 | Van Steenkiste et al. |
| 6,287,331 B1 | 9/2001 | Heath |
| 6,287,332 B1 | 9/2001 | Bolz et al. |
| 6,287,335 B1 | 9/2001 | Drasler et al. |
| 6,287,628 B1 | 9/2001 | Hossainy et al. |
| 6,290,721 B1 | 9/2001 | Heath |
| 6,290,722 B1 | 9/2001 | Wang |
| 6,291,076 B1 | 9/2001 | Nakatsugawa |
| 6,299,604 B1 | 10/2001 | Ragheb et al. |
| 6,299,755 B1 | 10/2001 | Richter |
| 6,306,144 B1 | 10/2001 | Sydney et al. |
| 6,309,414 B1 | 10/2001 | Rolando et al. |
| 6,312,463 B1 | 11/2001 | Rourke et al. |
| 6,315,708 B1 | 11/2001 | Salmon et al. |
| 6,323,146 B1 | 11/2001 | Pugh et al. |
| 6,325,825 B1 | 12/2001 | Kula et al. |
| 6,327,504 B1 | 12/2001 | Dolgin et al. |
| 6,331,312 B1 | 12/2001 | Lee et al. |
| 6,335,029 B1 | 1/2002 | Kamath et al. |
| 6,337,076 B1 | 1/2002 | Studin |
| 6,338,739 B1 | 1/2002 | Datta et al. |
| 6,342,507 B1 | 1/2002 | Naicker et al. |
| 6,344,055 B1 | 2/2002 | Shukov |
| 6,348,960 B1 | 2/2002 | Etori et al. |
| 6,358,276 B1 | 3/2002 | Edwin |
| 6,364,823 B1 | 4/2002 | Garibaldi et al. |
| 6,364,856 B1 | 4/2002 | Ding et al. |
| 6,364,903 B2 | 4/2002 | Tseng et al. |
| 6,366,808 B1 | 4/2002 | Schroeppel et al. |
| 6,368,658 B1 | 4/2002 | Schwarz et al. |
| 6,369,355 B1 | 4/2002 | Saunders |
| 6,375,826 B1 | 4/2002 | Wang et al. |
| 6,379,379 B1 | 4/2002 | Wang |
| 6,379,382 B1 | 4/2002 | Yang et al. |
| 6,379,383 B1 | 4/2002 | Palmaz et al. |
| 6,379,392 B1 | 4/2002 | Walak |
| 6,383,214 B1 | 5/2002 | Banas et al. |
| 6,387,121 B1 | 5/2002 | Alt |
| 6,387,124 B1 | 5/2002 | Buscemi et al. |
| 6,390,967 B1 | 5/2002 | Forman et al. |
| 6,391,033 B2 | 5/2002 | Ryan |
| 6,391,052 B2 | 5/2002 | Bulrge et al. |
| 6,395,326 B1 | 5/2002 | Castro et al. |
| 6,398,806 B1 | 6/2002 | You |
| 6,409,754 B1 | 6/2002 | Smith et al. |
| 6,419,692 B1 | 7/2002 | Yang et al. |
| 6,423,092 B2 | 7/2002 | Datta et al. |
| 6,425,855 B2 | 7/2002 | Tomonto |
| 6,436,133 B1 | 8/2002 | Furst et al. |
| 6,440,166 B1 | 8/2002 | Kolluri |
| 6,440,487 B1 | 8/2002 | Delfino et al. |
| 6,440,503 B1 | 8/2002 | Merdan et al. |
| 6,447,540 B1 | 9/2002 | Fontaine et al. |
| 6,451,871 B1 | 9/2002 | Winterton et al. |
| 6,458,153 B1 | 10/2002 | Bailey et al. |
| 6,468,304 B1 | 10/2002 | Dubois-Rande et al. |
| 6,471,721 B1 | 10/2002 | Dang |
| 6,471,980 B1 | 10/2002 | Sirhan et al. |
| 6,475,477 B1 | 11/2002 | Kohn et al. |
| 6,478,815 B1 | 11/2002 | Alt |
| 6,479,146 B1 | 11/2002 | Caruso et al. |
| 6,486,588 B2 | 11/2002 | Doron |
| 6,488,702 B1 | 12/2002 | Besselink |
| 6,491,666 B1 | 12/2002 | Santini, Jr. et al. |
| 6,491,720 B1 | 12/2002 | Vallana et al. |
| 6,492,096 B1 | 12/2002 | Liu et al. |
| 6,503,556 B2 | 1/2003 | Harish et al. |
| 6,503,921 B2 | 1/2003 | Naicker et al. |
| 6,506,437 B1 | 1/2003 | Harish et al. |
| 6,506,972 B1 | 1/2003 | Wang |

| | | |
|---|---|---|
| 6,514,283 B2 | 2/2003 | DiMatteo et al. |
| 6,517,571 B1 | 2/2003 | Brauker et al. |
| 6,517,888 B1 | 2/2003 | Weber |
| 6,524,274 B1 | 2/2003 | Rosenthal et al. |
| 6,524,334 B1 | 2/2003 | Thompson |
| 6,527,801 B1 | 3/2003 | Dutta |
| 6,527,938 B2 | 3/2003 | Bales et al. |
| 6,529,774 B1 * | 3/2003 | Greene .................. 600/545 |
| 6,530,949 B2 | 3/2003 | Konya et al. |
| 6,530,951 B1 | 3/2003 | Bates et al. |
| 6,533,905 B2 | 3/2003 | Johnson et al. |
| 6,537,310 B1 | 3/2003 | Palmaz et al. |
| 6,537,312 B2 | 3/2003 | Datta et al. |
| 6,544,582 B1 | 4/2003 | Yoe |
| 6,545,097 B2 | 4/2003 | Pinchuk et al. |
| 6,549,811 B2 | 4/2003 | Stewart et al. |
| 6,554,854 B1 | 4/2003 | Flanagan |
| 6,558,422 B1 | 5/2003 | Baker et al. |
| 6,558,733 B1 | 5/2003 | Hossainy et al. |
| 6,565,602 B2 | 5/2003 | Rolando et al. |
| 6,569,489 B1 | 5/2003 | Li |
| 6,584,349 B1 | 6/2003 | Sage, Jr. et al. |
| 6,585,764 B2 | 7/2003 | Wright et al. |
| 6,585,765 B1 | 7/2003 | Hossainy et al. |
| 6,586,705 B1 | 7/2003 | Schell |
| 6,589,286 B1 | 7/2003 | Litner |
| 6,599,558 B1 | 7/2003 | Al-Lamee et al. |
| 6,602,287 B1 | 8/2003 | Millare et al. |
| 6,607,598 B2 | 8/2003 | Schwarz et al. |
| 6,613,077 B2 | 9/2003 | Gilligan et al. |
| 6,613,083 B2 | 9/2003 | Alt |
| 6,613,432 B2 | 9/2003 | Zamora et al. |
| 6,616,765 B1 | 9/2003 | Wu et al. |
| 6,626,933 B1 | 9/2003 | Lau et al. |
| 6,626,936 B2 | 9/2003 | Stinson |
| 6,626,939 B1 | 9/2003 | Burnside et al. |
| 6,627,321 B1 | 9/2003 | Ellingsen et al. |
| 6,628,989 B1 | 9/2003 | Penner |
| 6,629,992 B2 | 10/2003 | Bigus et al. |
| 6,635,082 B1 | 10/2003 | Hossainy et al. |
| 6,638,302 B1 | 10/2003 | Curcio et al. |
| 6,641,607 B1 | 11/2003 | Hossainy et al. |
| 6,652,575 B2 | 11/2003 | Wang |
| 6,652,578 B1 | 11/2003 | Bailey et al. |
| 6,652,581 B1 | 11/2003 | Ding |
| 6,652,582 B1 | 11/2003 | Stinson |
| 6,660,034 B1 | 12/2003 | Mandrusov et al. |
| 6,663,662 B2 | 12/2003 | Pacetti et al. |
| 6,663,664 B1 | 12/2003 | Pacetti |
| 6,669,980 B2 | 12/2003 | Hansen |
| 6,673,105 B1 | 1/2004 | Chen |
| 6,673,385 B1 | 1/2004 | Ding et al. |
| 6,673,999 B1 | 1/2004 | Wang et al. |
| 6,676,987 B2 | 1/2004 | Zhong |
| 6,676,989 B2 | 1/2004 | Kirkpatrick et al. |
| 6,689,160 B1 | 2/2004 | Okuda et al. |
| 6,689,803 B2 | 2/2004 | Hunter |
| 6,695,865 B2 | 2/2004 | Boyle et al. |
| 6,696,666 B2 | 2/2004 | Weber et al. |
| 6,696,667 B1 | 2/2004 | Flanagan |
| 6,699,281 B2 | 3/2004 | Vallana et al. |
| 6,699,282 B2 | 3/2004 | Sceusa |
| 6,709,379 B1 | 3/2004 | Brandau et al. |
| 6,709,397 B2 | 3/2004 | Taylor |
| 6,709,451 B1 | 3/2004 | Noble et al. |
| 6,710,053 B2 | 3/2004 | Naicker et al. |
| 6,712,844 B2 | 3/2004 | Pacetti |
| 6,712,845 B2 | 3/2004 | Hossainy |
| 6,713,671 B1 | 3/2004 | Wang et al. |
| 6,716,444 B1 | 4/2004 | Castro et al. |
| 6,719,987 B2 | 4/2004 | Langford et al. |
| 6,720,402 B2 | 4/2004 | Langer et al. |
| 6,723,120 B2 | 4/2004 | Yan |
| 6,723,350 B2 | 4/2004 | Burrell et al. |
| 6,725,901 B1 | 4/2004 | Kramer et al. |
| 6,726,712 B1 | 4/2004 | Raeder-Devens |
| 6,730,117 B1 | 5/2004 | Tseng et al. |
| 6,730,120 B2 | 5/2004 | Berg et al. |
| 6,730,699 B2 | 5/2004 | Li et al. |
| 6,733,513 B2 | 5/2004 | Boyle et al. |
| 6,740,077 B1 | 5/2004 | Brandau et al. |
| 6,743,388 B2 | 6/2004 | Sridharan et al. |
| 6,752,826 B2 | 6/2004 | Holloway et al. |
| 6,752,829 B2 | 6/2004 | Kocur et al. |
| 6,753,071 B1 | 6/2004 | Pacetti |
| 6,758,859 B1 | 7/2004 | Dang et al. |
| 6,764,505 B1 | 7/2004 | Hossainy et al. |
| 6,764,579 B2 | 7/2004 | Veerasamy et al. |
| 6,764,709 B2 | 7/2004 | Flanagan |
| 6,765,144 B1 | 7/2004 | Wang et al. |
| 6,767,360 B1 | 7/2004 | Alt et al. |
| 6,770,086 B1 | 8/2004 | Girton |
| 6,770,729 B2 | 8/2004 | Van Antwerp |
| 6,774,278 B1 | 8/2004 | Ragheb et al. |
| 6,776,022 B2 | 8/2004 | Kula et al. |
| 6,776,094 B1 | 8/2004 | Whitesides et al. |
| 6,776,793 B2 | 8/2004 | Brown et al. |
| 6,780,424 B2 | 8/2004 | Claude |
| 6,783,543 B2 | 8/2004 | Jang |
| 6,790,228 B2 | 9/2004 | Hossainy et al. |
| 6,793,877 B1 | 9/2004 | Pettersen et al. |
| 6,796,435 B2 | 9/2004 | Izumi |
| 6,803,070 B2 | 10/2004 | Weber |
| 6,805,709 B1 | 10/2004 | Schaldach et al. |
| 6,805,898 B1 | 10/2004 | Wu et al. |
| 6,807,440 B2 | 10/2004 | Weber |
| RE38,653 E | 11/2004 | Igaki et al. |
| 6,815,609 B1 | 11/2004 | Wang et al. |
| 6,820,676 B2 | 11/2004 | Palmaz et al. |
| 6,827,737 B2 | 12/2004 | Hill et al. |
| 6,827,966 B2 | 12/2004 | Qiu et al. |
| 6,833,004 B2 | 12/2004 | Ishii et al. |
| 6,846,323 B2 | 1/2005 | Yip et al. |
| 6,846,841 B2 | 1/2005 | Hunter et al. |
| 6,847,837 B1 | 1/2005 | Melzer et al. |
| 6,849,085 B2 | 2/2005 | Marton |
| 6,849,089 B2 | 2/2005 | Stoll |
| 6,852,122 B2 | 2/2005 | Rush |
| 6,854,172 B2 | 2/2005 | Kaese et al. |
| 6,861,088 B2 | 3/2005 | Weber et al. |
| 6,865,810 B2 | 3/2005 | Stinson |
| 6,866,805 B2 | 3/2005 | Hong et al. |
| 6,869,443 B2 | 3/2005 | Buscemi et al. |
| 6,869,701 B1 | 3/2005 | Aita et al. |
| 6,875,227 B2 | 4/2005 | Yoon |
| 6,878,249 B2 | 4/2005 | Kouyama et al. |
| 6,884,429 B2 | 4/2005 | Koziak et al. |
| 6,887,270 B2 | 5/2005 | Miller et al. |
| 6,887,857 B2 | 5/2005 | Naimark et al. |
| 6,896,697 B1 | 5/2005 | Yip et al. |
| 6,899,731 B2 | 5/2005 | Li et al. |
| 6,899,914 B2 | 5/2005 | Schaldach et al. |
| 6,904,658 B2 | 6/2005 | Hines |
| 6,908,506 B2 | 6/2005 | Zimmermann |
| 6,908,622 B2 | 6/2005 | Barry et al. |
| 6,908,624 B2 | 6/2005 | Hossainy et al. |
| 6,913,617 B1 | 7/2005 | Reiss |
| 6,913,765 B2 | 7/2005 | Li et al. |
| 6,918,869 B2 | 7/2005 | Shaw et al. |
| 6,918,927 B2 | 7/2005 | Bates et al. |
| 6,921,390 B2 | 7/2005 | Bucay-Couto et al. |
| 6,923,996 B2 | 8/2005 | Epstein et al. |
| 6,926,735 B2 | 8/2005 | Henderson |
| 6,932,930 B2 | 8/2005 | DeSimone et al. |
| 6,936,066 B2 | 8/2005 | Palmaz et al. |
| 6,938,668 B2 | 9/2005 | Whicher et al. |
| 6,939,320 B2 | 9/2005 | Lennox |
| 6,945,993 B2 | 9/2005 | Kveen et al. |
| 6,951,053 B2 | 10/2005 | Padilla et al. |
| 6,953,560 B1 | 10/2005 | Castro et al. |
| 6,953,594 B2 | 10/2005 | Lee et al. |
| 6,954,977 B2 | 10/2005 | Maguire et al. |
| 6,955,661 B1 | 10/2005 | Herweck et al. |
| 6,955,685 B2 | 10/2005 | Escamilla et al. |
| 6,962,822 B2 | 11/2005 | Hart et al. |
| 6,964,817 B2 | 11/2005 | Date et al. |
| 6,971,813 B2 | 12/2005 | Shekalim et al. |
| 6,972,130 B1 | 12/2005 | Lee et al. |

| | | |
|---|---|---|
| 6,973,718 B2 | 12/2005 | Sheppard, Jr. et al. |
| 6,979,346 B1 | 12/2005 | Hossainy et al. |
| 6,979,347 B1 | 12/2005 | Wu et al. |
| 6,979,348 B2 | 12/2005 | Sundar |
| 6,981,986 B1 | 1/2006 | Brown et al. |
| 6,984,404 B1 | 1/2006 | Talton et al. |
| 6,986,899 B2 | 1/2006 | Hossainy et al. |
| 6,989,156 B2 | 1/2006 | Gillis |
| 6,991,709 B2 | 1/2006 | Gopalraja et al. |
| 7,001,421 B2 | 2/2006 | Cheng et al. |
| 7,004,968 B2 | 2/2006 | Lootz et al. |
| 7,011,670 B2 | 3/2006 | Radisch, Jr. |
| 7,011,678 B2 | 3/2006 | Tenerz et al. |
| 7,011,680 B2 | 3/2006 | Alt |
| 7,018,408 B2 | 3/2006 | Bailey et al. |
| 7,022,334 B1 | 4/2006 | Ding et al. |
| 7,041,130 B2 | 5/2006 | Santini, Jr. |
| 7,048,767 B2 | 5/2006 | Namavar |
| 7,048,939 B2 | 5/2006 | Elkins et al. |
| 7,052,488 B2 | 5/2006 | Uhland |
| 7,056,338 B2 | 6/2006 | Shanley et al. |
| 7,056,339 B2 | 6/2006 | Elkins et al. |
| 7,060,051 B2 | 6/2006 | Palasis |
| 7,060,240 B2 | 6/2006 | Costa et al. |
| 7,063,748 B2 | 6/2006 | Talton |
| 7,067,606 B2 | 6/2006 | Mather et al. |
| 7,070,576 B2 | 7/2006 | O'Brien et al. |
| 7,078,108 B2 | 7/2006 | Zhang et al. |
| 7,099,091 B2 | 8/2006 | Taniguchi et al. |
| 7,101,391 B2 | 9/2006 | Scheuermann et al. |
| 7,101,394 B2 | 9/2006 | Hamm et al. |
| 7,105,018 B1 | 9/2006 | Yip et al. |
| 7,105,199 B2 | 9/2006 | Blinn et al. |
| 7,108,716 B2 | 9/2006 | Burnside et al. |
| 7,157,096 B2 | 1/2007 | Zhang et al. |
| 7,160,592 B2 | 1/2007 | Rypacek et al. |
| 7,163,715 B1 | 1/2007 | Kramer |
| 7,169,173 B2 | 1/2007 | Hossainy et al. |
| 7,169,178 B1 | 1/2007 | Santos et al. |
| 7,195,640 B2 | 3/2007 | Falotico et al. |
| 7,195,641 B2 | 3/2007 | Palmaz et al. |
| 7,198,675 B2 | 4/2007 | Fox et al. |
| 7,208,011 B2 | 4/2007 | Shanley et al. |
| 7,208,172 B2 | 4/2007 | Birdsall et al. |
| 7,220,816 B2 | 5/2007 | Pacetti |
| 7,226,475 B2 | 6/2007 | Lenz et al. |
| 7,229,471 B2 | 6/2007 | Gale et al. |
| 7,235,096 B1 | 6/2007 | Van Tassel et al. |
| 7,235,098 B2 | 6/2007 | Palmaz |
| 7,238,199 B2 | 7/2007 | Feldman et al. |
| 7,241,295 B2 | 7/2007 | Maguire |
| 7,244,272 B2 | 7/2007 | Dubson et al. |
| 7,261,732 B2 | 8/2007 | Justino |
| 7,261,735 B2 | 8/2007 | Llanos et al. |
| 7,267,960 B2 | 9/2007 | Galibert et al. |
| 7,279,174 B2 | 10/2007 | Pacetti |
| 7,279,175 B2 | 10/2007 | Chen |
| 7,294,409 B2 | 11/2007 | Lye et al. |
| 7,311,727 B2 | 12/2007 | Mazumder et al. |
| 7,323,189 B2 | 1/2008 | Pathak |
| RE40,122 E | 2/2008 | Thompson |
| 7,331,993 B2 | 2/2008 | White |
| 7,335,375 B2 | 2/2008 | Li et al. |
| 7,344,560 B2 | 3/2008 | Gregorich et al. |
| 7,344,563 B2 | 3/2008 | Vallana et al. |
| 7,393,589 B2 | 7/2008 | Aharonov et al. |
| 7,402,173 B2 | 7/2008 | Scheuermann et al. |
| 7,416,558 B2 | 8/2008 | Yip et al. |
| 7,432,327 B2 | 10/2008 | Glasgow et al. |
| 7,462,366 B2 | 12/2008 | Lanphere |
| 7,498,385 B2 | 3/2009 | Swetlin et al. |
| 7,507,433 B2 | 3/2009 | Weber |
| 7,537,610 B2 | 5/2009 | Reiss |
| 7,547,445 B2 | 6/2009 | Chudzik et al. |
| 7,563,277 B2 | 7/2009 | Case et al. |
| 7,637,941 B1 | 12/2009 | Manicka et al. |
| 7,651,527 B2 | 1/2010 | Krivoruchko et al. |
| 7,691,401 B2 | 4/2010 | Castro et al. |
| 7,713,297 B2 | 5/2010 | Alt |
| 7,713,573 B2 | 5/2010 | Owens et al. |
| 7,722,805 B2 | 5/2010 | Hao et al. |
| 7,749,264 B2 | 7/2010 | Gregorich et al. |
| 7,758,635 B2 | 7/2010 | Parsonage |
| 7,771,773 B2 | 8/2010 | Namavar |
| 7,776,926 B1 | 8/2010 | Claude et al. |
| 2001/0001834 A1 | 5/2001 | Palmaz et al. |
| 2001/0002000 A1 | 5/2001 | Kumar et al. |
| 2001/0002435 A1 | 5/2001 | Berg et al. |
| 2001/0013166 A1 | 8/2001 | Yan |
| 2001/0021871 A1 | 9/2001 | Stinson |
| 2001/0021873 A1 | 9/2001 | Stinson |
| 2001/0027299 A1 | 10/2001 | Yang et al. |
| 2001/0029398 A1 | 10/2001 | Jadhav |
| 2001/0029660 A1 | 10/2001 | Johnson |
| 2001/0032011 A1 | 10/2001 | Stanford |
| 2001/0032013 A1 | 10/2001 | Marton |
| 2001/0032014 A1 | 10/2001 | Yang et al. |
| 2001/0044650 A1 | 11/2001 | Simso et al. |
| 2002/0000175 A1 | 1/2002 | Hintermaier et al. |
| 2002/0000406 A1 | 1/2002 | Izumi |
| 2002/0004060 A1 | 1/2002 | Heublein et al. |
| 2002/0007102 A1 | 1/2002 | Salmon et al. |
| 2002/0007209 A1 | 1/2002 | Scheerder et al. |
| 2002/0010505 A1 | 1/2002 | Richter |
| 2002/0016623 A1 | 2/2002 | Kula et al. |
| 2002/0016624 A1 | 2/2002 | Patterson et al. |
| 2002/0028827 A1 | 3/2002 | Naicker et al. |
| 2002/0032477 A1 | 3/2002 | Helmus et al. |
| 2002/0035394 A1 | 3/2002 | Fierens et al. |
| 2002/0038146 A1 | 3/2002 | Harry |
| 2002/0042039 A1 | 4/2002 | Kim et al. |
| 2002/0049495 A1 | 4/2002 | Kutryk et al. |
| 2002/0051730 A1 | 5/2002 | Bodnar et al. |
| 2002/0051846 A1 | 5/2002 | Kirkpatrick et al. |
| 2002/0065553 A1 | 5/2002 | Weber |
| 2002/0082679 A1 | 6/2002 | Sirhan et al. |
| 2002/0087123 A1 | 7/2002 | Hossainy et al. |
| 2002/0090313 A1 | 7/2002 | Wang et al. |
| 2002/0091375 A1 | 7/2002 | Sahatjian et al. |
| 2002/0098278 A1 | 7/2002 | Bates et al. |
| 2002/0099434 A1 | 7/2002 | Buscemi et al. |
| 2002/0099438 A1 | 7/2002 | Furst |
| 2002/0103527 A1 | 8/2002 | Kocur et al. |
| 2002/0103528 A1 | 8/2002 | Schaldach et al. |
| 2002/0111694 A1 | 8/2002 | Ellingsen et al. |
| 2002/0121497 A1 | 9/2002 | Tomonto |
| 2002/0123801 A1 | 9/2002 | Pacetti et al. |
| 2002/0133222 A1 | 9/2002 | Das |
| 2002/0133224 A1 | 9/2002 | Bajgar et al. |
| 2002/0138100 A1 | 9/2002 | Stoll et al. |
| 2002/0138131 A1 | 9/2002 | Solovay et al. |
| 2002/0138136 A1 | 9/2002 | Chandresekaran et al. |
| 2002/0138154 A1 | 9/2002 | Li et al. |
| 2002/0144757 A1 | 10/2002 | Craig et al. |
| 2002/0151964 A1 | 10/2002 | Smith et al. |
| 2002/0155212 A1 | 10/2002 | Hossainy |
| 2002/0165265 A1 | 11/2002 | Hunter et al. |
| 2002/0165578 A1 | 11/2002 | Sawitowski et al. |
| 2002/0165600 A1 | 11/2002 | Banas et al. |
| 2002/0165607 A1 | 11/2002 | Alt |
| 2002/0169493 A1 | 11/2002 | Widenhouse et al. |
| 2002/0178570 A1 | 12/2002 | Sogard et al. |
| 2002/0182241 A1 | 12/2002 | Borenstein et al. |
| 2002/0183581 A1 | 12/2002 | Yoe et al. |
| 2002/0183682 A1 | 12/2002 | Darvish et al. |
| 2002/0193336 A1 | 12/2002 | Elkins et al. |
| 2002/0193682 A1 | 12/2002 | Torchia et al. |
| 2002/0193869 A1 | 12/2002 | Dang |
| 2002/0197178 A1 | 12/2002 | Yan |
| 2002/0198601 A1 | 12/2002 | Bales et al. |
| 2003/0003127 A1 | 1/2003 | Brown et al. |
| 2003/0003220 A1 | 1/2003 | Zhong et al. |
| 2003/0004563 A1 | 1/2003 | Jackson et al. |
| 2003/0004564 A1 | 1/2003 | Elkins et al. |
| 2003/0009214 A1 | 1/2003 | Shanley |
| 2003/0018380 A1 | 1/2003 | Craig et al. |
| 2003/0018381 A1 | 1/2003 | Whitcher et al. |
| 2003/0023300 A1 | 1/2003 | Bailey et al. |

| | | |
|---|---|---|
| 2003/0028242 A1 | 2/2003 | Vallana et al. |
| 2003/0028243 A1 | 2/2003 | Bates et al. |
| 2003/0032892 A1 | 2/2003 | Erlach et al. |
| 2003/0033007 A1 | 2/2003 | Sirhan et al. |
| 2003/0044446 A1 | 3/2003 | Moro et al. |
| 2003/0050687 A1 | 3/2003 | Schwade et al. |
| 2003/0050692 A1 | 3/2003 | Sirhan et al. |
| 2003/0059640 A1 | 3/2003 | Marton et al. |
| 2003/0060871 A1 | 3/2003 | Hill et al. |
| 2003/0060873 A1 | 3/2003 | Gertner et al. |
| 2003/0064095 A1 | 4/2003 | Martin et al. |
| 2003/0068355 A1 | 4/2003 | Shanley et al. |
| 2003/0069631 A1 | 4/2003 | Stoll |
| 2003/0074053 A1 | 4/2003 | Palmaz et al. |
| 2003/0077200 A1 | 4/2003 | Craig et al. |
| 2003/0077310 A1 | 4/2003 | Pathak et al. |
| 2003/0083614 A1 | 5/2003 | Eisert |
| 2003/0083646 A1 | 5/2003 | Sirhan et al. |
| 2003/0083731 A1 | 5/2003 | Kramer et al. |
| 2003/0087024 A1 | 5/2003 | Flanagan |
| 2003/0088307 A1 | 5/2003 | Shulze et al. |
| 2003/0088312 A1 | 5/2003 | Kopia et al. |
| 2003/0099684 A1 | 5/2003 | Domb |
| 2003/0100815 A1 | 5/2003 | Da Silva et al. |
| 2003/0100830 A1 | 5/2003 | Zhong et al. |
| 2003/0104030 A1 | 6/2003 | Igaki et al. |
| 2003/0105511 A1 | 6/2003 | Welsh et al. |
| 2003/0108659 A1 | 6/2003 | Bales et al. |
| 2003/0114917 A1 | 6/2003 | Holloway et al. |
| 2003/0114921 A1 | 6/2003 | Yoon |
| 2003/0118692 A1 | 6/2003 | Wang et al. |
| 2003/0120339 A1 | 6/2003 | Banik et al. |
| 2003/0124055 A1 | 7/2003 | Li et al. |
| 2003/0125803 A1 | 7/2003 | Vallana |
| 2003/0130718 A1 | 7/2003 | Palmas et al. |
| 2003/0139799 A1 | 7/2003 | Ley et al. |
| 2003/0143330 A1 | 7/2003 | Loomis et al. |
| 2003/0144728 A1 | 7/2003 | Scheuermann et al. |
| 2003/0150380 A1 | 8/2003 | Yoe |
| 2003/0153901 A1 | 8/2003 | Herweck et al. |
| 2003/0158598 A1 | 8/2003 | Ashton et al. |
| 2003/0170605 A1 | 9/2003 | Long et al. |
| 2003/0181975 A1 | 9/2003 | Ishii et al. |
| 2003/0185895 A1 | 10/2003 | Lanphere |
| 2003/0190406 A1 | 10/2003 | Hossainy et al. |
| 2003/0195613 A1 | 10/2003 | Curcio et al. |
| 2003/0199993 A1 | 10/2003 | Gellman et al. |
| 2003/0204239 A1 | 10/2003 | Carlyle et al. |
| 2003/0211135 A1 | 11/2003 | Greenhalgh et al. |
| 2003/0216803 A1 | 11/2003 | Ledergerber |
| 2003/0219562 A1 | 11/2003 | Rypacek et al. |
| 2003/0221307 A1 | 12/2003 | Kaese et al. |
| 2003/0228523 A1 | 12/2003 | DeLongchamp et al. |
| 2003/0236513 A1 | 12/2003 | Schwarz et al. |
| 2004/0000046 A1 | 1/2004 | Stinson |
| 2004/0000540 A1 | 1/2004 | Soboyejo et al. |
| 2004/0004063 A1 | 1/2004 | Merdan |
| 2004/0006382 A1 | 1/2004 | Sohier |
| 2004/0018296 A1 | 1/2004 | Castro et al. |
| 2004/0019376 A1 | 1/2004 | Alt |
| 2004/0022939 A1 | 2/2004 | Kim et al. |
| 2004/0024448 A1 | 2/2004 | Chang et al. |
| 2004/0029303 A1 | 2/2004 | Hart et al. |
| 2004/0030218 A1 | 2/2004 | Kocur et al. |
| 2004/0030377 A1 | 2/2004 | Dubson et al. |
| 2004/0030379 A1 | 2/2004 | Hamm et al. |
| 2004/0034409 A1 | 2/2004 | Heublein et al. |
| 2004/0039438 A1 | 2/2004 | Alt |
| 2004/0039441 A1 | 2/2004 | Rowland et al. |
| 2004/0044397 A1 | 3/2004 | Stinson |
| 2004/0047980 A1 | 3/2004 | Pacetti et al. |
| 2004/0059407 A1 | 3/2004 | Escamilla et al. |
| 2004/0059409 A1 | 3/2004 | Stenzel |
| 2004/0067301 A1 | 4/2004 | Ding |
| 2004/0071861 A1 | 4/2004 | Mandrusov et al. |
| 2004/0073155 A1 | 4/2004 | Laufer et al. |
| 2004/0073284 A1 | 4/2004 | Bates et al. |
| 2004/0073293 A1 | 4/2004 | Thompson |
| 2004/0073297 A1 | 4/2004 | Rohde et al. |
| 2004/0073298 A1 | 4/2004 | Hossainy |
| 2004/0078071 A1 | 4/2004 | Escamilla et al. |
| 2004/0082682 A1 | 4/2004 | Loomis et al. |
| 2004/0088038 A1 | 5/2004 | Dehnad et al. |
| 2004/0088041 A1 | 5/2004 | Stanford |
| 2004/0093071 A1 | 5/2004 | Jang |
| 2004/0093075 A1 | 5/2004 | Kuehne |
| 2004/0093076 A1 | 5/2004 | White et al. |
| 2004/0098089 A1 | 5/2004 | Weber |
| 2004/0098108 A1 | 5/2004 | Harder et al. |
| 2004/0098119 A1 | 5/2004 | Wang |
| 2004/0106975 A1 | 6/2004 | Solovay et al. |
| 2004/0106984 A1 | 6/2004 | Stinson |
| 2004/0106985 A1 | 6/2004 | Jang |
| 2004/0111150 A1 | 6/2004 | Berg et al. |
| 2004/0116999 A1 | 6/2004 | Ledergerber |
| 2004/0117005 A1 | 6/2004 | Gadde et al. |
| 2004/0117008 A1 | 6/2004 | Wnendt et al. |
| 2004/0122504 A1 | 6/2004 | Hogendijk |
| 2004/0126566 A1 | 7/2004 | Axen et al. |
| 2004/0133270 A1 | 7/2004 | Grandt |
| 2004/0134886 A1 | 7/2004 | Wagner et al. |
| 2004/0137039 A1 | 7/2004 | Sukhishvili et al. |
| 2004/0138738 A1 | 7/2004 | Stinson |
| 2004/0142014 A1 | 7/2004 | Litvack et al. |
| 2004/0143317 A1 | 7/2004 | Stinson et al. |
| 2004/0143321 A1 | 7/2004 | Litvack et al. |
| 2004/0148010 A1 | 7/2004 | Rush |
| 2004/0148015 A1 | 7/2004 | Lye et al. |
| 2004/0153138 A1 | 8/2004 | Murphy |
| 2004/0157073 A1 | 8/2004 | Burrell et al. |
| 2004/0158308 A1 | 8/2004 | Hogendijk et al. |
| 2004/0158310 A1 | 8/2004 | Weber et al. |
| 2004/0167572 A1 | 8/2004 | Roth et al. |
| 2004/0167609 A1 | 8/2004 | Majercak |
| 2004/0167612 A1 | 8/2004 | Grignani et al. |
| 2004/0172124 A1 | 9/2004 | Vallana et al. |
| 2004/0181252 A1 | 9/2004 | Boyle et al. |
| 2004/0181275 A1 | 9/2004 | Noble et al. |
| 2004/0181276 A1 | 9/2004 | Brown et al. |
| 2004/0181278 A1 | 9/2004 | Tseng et al. |
| 2004/0182511 A1 | 9/2004 | Rakos et al. |
| 2004/0186553 A1 | 9/2004 | Yan |
| 2004/0191293 A1 | 9/2004 | Claude |
| 2004/0191404 A1 | 9/2004 | Hossainy et al. |
| 2004/0202692 A1 | 10/2004 | Shanley et al. |
| 2004/0204750 A1 | 10/2004 | Dinh |
| 2004/0211362 A1 | 10/2004 | Castro et al. |
| 2004/0219214 A1 | 11/2004 | Gravett et al. |
| 2004/0220510 A1 | 11/2004 | Koullick et al. |
| 2004/0220659 A1 | 11/2004 | Girton |
| 2004/0220660 A1 | 11/2004 | Shanley et al. |
| 2004/0220662 A1 | 11/2004 | Dang et al. |
| 2004/0224001 A1 | 11/2004 | Pacetti et al. |
| 2004/0225346 A1 | 11/2004 | Mazumder et al. |
| 2004/0228905 A1 | 11/2004 | Greenspan et al. |
| 2004/0230176 A1 | 11/2004 | Shanahan et al. |
| 2004/0230225 A1 | 11/2004 | Penner et al. |
| 2004/0230290 A1 | 11/2004 | Weber et al. |
| 2004/0230293 A1 | 11/2004 | Yip et al. |
| 2004/0234737 A1 | 11/2004 | Pacetti |
| 2004/0236415 A1 | 11/2004 | Thomas |
| 2004/0236416 A1 | 11/2004 | Falotico |
| 2004/0237282 A1 | 12/2004 | Hines |
| 2004/0242106 A1 | 12/2004 | Rabasco et al. |
| 2004/0243217 A1 | 12/2004 | Andersen |
| 2004/0243237 A1 | 12/2004 | Unwin et al. |
| 2004/0243241 A1 | 12/2004 | Istephanous et al. |
| 2004/0247671 A1 | 12/2004 | Prescott et al. |
| 2004/0249440 A1 | 12/2004 | Bucker et al. |
| 2004/0249443 A1 | 12/2004 | Shanley et al. |
| 2004/0249444 A1 | 12/2004 | Reiss |
| 2004/0249445 A1 | 12/2004 | Rosenthal et al. |
| 2004/0249449 A1 | 12/2004 | Shanley et al. |
| 2004/0254419 A1 | 12/2004 | Wang et al. |
| 2004/0254635 A1 | 12/2004 | Shanley et al. |
| 2005/0004661 A1 | 1/2005 | Lewis et al. |
| 2005/0010275 A1 | 1/2005 | Sahatjian |
| 2005/0010279 A1 | 1/2005 | Tenerz et al. |

| | | | | | |
|---|---|---|---|---|---|
| 2005/0015142 A1 | 1/2005 | Austin et al. | 2005/0187611 A1 | 8/2005 | Ding et al. |
| 2005/0019265 A1 | 1/2005 | Hammer et al. | 2005/0187615 A1 | 8/2005 | Williams et al. |
| 2005/0019371 A1 | 1/2005 | Anderson et al. | 2005/0192657 A1 | 9/2005 | Colen et al. |
| 2005/0021127 A1 | 1/2005 | Kawula | 2005/0192662 A1 | 9/2005 | Ward |
| 2005/0021128 A1 | 1/2005 | Nakahama et al. | 2005/0192664 A1 | 9/2005 | Eisert |
| 2005/0022627 A1 | 2/2005 | Chen | 2005/0196424 A1 | 9/2005 | Chappa |
| 2005/0025804 A1 | 2/2005 | Heller | 2005/0208098 A1 | 9/2005 | Castro et al. |
| 2005/0027350 A1 | 2/2005 | Momma et al. | 2005/0208100 A1 | 9/2005 | Weber et al. |
| 2005/0033407 A1 | 2/2005 | Weber et al. | 2005/0209680 A1 | 9/2005 | Gale et al. |
| 2005/0033411 A1 | 2/2005 | Wu et al. | 2005/0209681 A1 | 9/2005 | Curcio et al. |
| 2005/0033412 A1 | 2/2005 | Wu et al. | 2005/0211680 A1 | 9/2005 | Li et al. |
| 2005/0033417 A1 | 2/2005 | Borges et al. | 2005/0214951 A1 | 9/2005 | Nahm et al. |
| 2005/0037047 A1 | 2/2005 | Song | 2005/0216074 A1 | 9/2005 | Sahatjian |
| 2005/0037050 A1 | 2/2005 | Weber | 2005/0216075 A1 | 9/2005 | Wang et al. |
| 2005/0038134 A1 | 2/2005 | Loomis et al. | 2005/0220853 A1 | 10/2005 | Dao et al. |
| 2005/0038501 A1 | 2/2005 | Moore, Jr. et al. | 2005/0221072 A1 | 10/2005 | Dubrow et al. |
| 2005/0042288 A1 | 2/2005 | Koblish et al. | 2005/0222671 A1 | 10/2005 | Schaeffer et al. |
| 2005/0042440 A1 | 2/2005 | Bach et al. | 2005/0228477 A1 | 10/2005 | Grainger et al. |
| 2005/0055044 A1 | 3/2005 | Kangas | 2005/0228483 A1 | 10/2005 | Kaplan et al. |
| 2005/0055080 A1 | 3/2005 | Istephanous et al. | 2005/0228491 A1 | 10/2005 | Snyder et al. |
| 2005/0055085 A1 | 3/2005 | Rivron et al. | 2005/0232968 A1 | 10/2005 | Palmaz et al. |
| 2005/0060020 A1 | 3/2005 | Jenson | 2005/0233965 A1 | 10/2005 | Schwartz et al. |
| 2005/0060021 A1 | 3/2005 | O'Brien et al. | 2005/0234538 A1 | 10/2005 | Litvack et al. |
| 2005/0064088 A1 | 3/2005 | Fredrickson | 2005/0240280 A1 | 10/2005 | Aliski et al. |
| 2005/0069630 A1 | 3/2005 | Fox et al. | 2005/0244459 A1 | 11/2005 | DeWitt et al. |
| 2005/0070989 A1 | 3/2005 | Lye et al. | 2005/0251245 A1 | 11/2005 | Sieradzki et al. |
| 2005/0070990 A1 | 3/2005 | Stinson | 2005/0251249 A1 | 11/2005 | Sahatjian |
| 2005/0070996 A1 | 3/2005 | Dinh et al. | 2005/0252893 A1 | 11/2005 | Shapovalov et al. |
| 2005/0071016 A1 | 3/2005 | Hausdorf et al. | 2005/0255707 A1 | 11/2005 | Hart et al. |
| 2005/0072544 A1 | 4/2005 | Palmaz et al. | 2005/0261760 A1 | 11/2005 | Weber |
| 2005/0074479 A1 | 4/2005 | Weber et al. | 2005/0266039 A1 | 12/2005 | Weber |
| 2005/0074545 A1 | 4/2005 | Thomas | 2005/0266040 A1 | 12/2005 | Gerberding |
| 2005/0075714 A1 | 4/2005 | Cheng et al. | 2005/0266041 A1 | 12/2005 | Gerold et al. |
| 2005/0077305 A1 | 4/2005 | Guevara | 2005/0267560 A1 | 12/2005 | Bates et al. |
| 2005/0079132 A1 | 4/2005 | Wang et al. | 2005/0267561 A1 | 12/2005 | Jones et al. |
| 2005/0079199 A1 | 4/2005 | Heruth et al. | 2005/0271706 A1 | 12/2005 | Anderson et al. |
| 2005/0079356 A1 | 4/2005 | Rathenow et al. | 2005/0276837 A1 | 12/2005 | Anderson et al. |
| 2005/0092615 A1 | 5/2005 | Birdsall et al. | 2005/0278016 A1 | 12/2005 | Welsh et al. |
| 2005/0096731 A1 | 5/2005 | Looi et al. | 2005/0278021 A1 | 12/2005 | Bates et al. |
| 2005/0100577 A1 | 5/2005 | Parker et al. | 2005/0281863 A1 | 12/2005 | Anderson et al. |
| 2005/0100609 A1 | 5/2005 | Claude | 2005/0283224 A1 | 12/2005 | King |
| 2005/0102025 A1 | 5/2005 | Laroche et al. | 2005/0283229 A1 | 12/2005 | Dugan et al. |
| 2005/0106212 A1 | 5/2005 | Gertner et al. | 2005/0287188 A1 | 12/2005 | Anderson et al. |
| 2005/0107869 A1 | 5/2005 | Sirhan et al. | 2006/0002979 A1 | 1/2006 | Ashammakhi et al. |
| 2005/0107870 A1 | 5/2005 | Wang et al. | 2006/0009839 A1 | 1/2006 | Tan |
| 2005/0113936 A1 | 5/2005 | Brustad et al. | 2006/0013850 A1 | 1/2006 | Domb |
| 2005/0119723 A1 | 6/2005 | Peacock | 2006/0014039 A1 | 1/2006 | Zhang et al. |
| 2005/0129727 A1 | 6/2005 | Weber et al. | 2006/0015175 A1 | 1/2006 | Palmaz et al. |
| 2005/0129731 A1 | 6/2005 | Horres et al. | 2006/0015361 A1 | 1/2006 | Sattler et al. |
| 2005/0131509 A1 | 6/2005 | Atanassoska et al. | 2006/0020742 A1 | 1/2006 | Au et al. |
| 2005/0131521 A1 | 6/2005 | Marton | 2006/0025848 A1 | 2/2006 | Weber et al. |
| 2005/0131522 A1 | 6/2005 | Stinson et al. | 2006/0035026 A1 | 2/2006 | Atanassoska et al. |
| 2005/0131527 A1 | 6/2005 | Pathak | 2006/0036281 A1 | 2/2006 | Patterson et al. |
| 2005/0131528 A1 | 6/2005 | Buscemi et al. | 2006/0036311 A1 | 2/2006 | Nakayama et al. |
| 2005/0136090 A1 | 6/2005 | Falotico et al. | 2006/0038027 A1 | 2/2006 | O'Connor et al. |
| 2005/0137677 A1 | 6/2005 | Rush | 2006/0040388 A1 | 2/2006 | Bromberg et al. |
| 2005/0137679 A1 | 6/2005 | Changelian et al. | 2006/0041182 A1 | 2/2006 | Forbes et al. |
| 2005/0137684 A1 | 6/2005 | Changelian et al. | 2006/0051397 A1 | 3/2006 | Maier et al. |
| 2005/0149169 A1 | 7/2005 | Wang et al. | 2006/0052744 A1 | 3/2006 | Weber |
| 2005/0149170 A1 | 7/2005 | Tassel et al. | 2006/0052863 A1 | 3/2006 | Harder et al. |
| 2005/0149175 A1 | 7/2005 | Hunter et al. | 2006/0052864 A1 | 3/2006 | Harder et al. |
| 2005/0149177 A1 | 7/2005 | Weber et al. | 2006/0058868 A1 | 3/2006 | Gale et al. |
| 2005/0159804 A1 | 7/2005 | Lad et al. | 2006/0062820 A1 | 3/2006 | Gertner et al. |
| 2005/0159805 A1 | 7/2005 | Weber et al. | 2006/0064160 A1 | 3/2006 | Gerold et al. |
| 2005/0159809 A1 | 7/2005 | Hezi-Yamit et al. | 2006/0067908 A1 | 3/2006 | Ding |
| 2005/0160600 A1 | 7/2005 | Bien et al. | 2006/0069427 A1 | 3/2006 | Savage et al. |
| 2005/0163821 A1 | 7/2005 | Sung et al. | 2006/0075044 A1 | 4/2006 | Fox et al. |
| 2005/0163954 A1 | 7/2005 | Shaw | 2006/0075092 A1 | 4/2006 | Kidokoro |
| 2005/0165301 A1 | 7/2005 | Smith et al. | 2006/0079958 A1 | 4/2006 | Stratford et al. |
| 2005/0165468 A1 | 7/2005 | Marton | 2006/0085062 A1 | 4/2006 | Lee et al. |
| 2005/0165470 A1 | 7/2005 | Weber | 2006/0085065 A1 | 4/2006 | Krause et al. |
| 2005/0169969 A1 | 8/2005 | Li et al. | 2006/0088566 A1 | 4/2006 | Parsonage et al. |
| 2005/0171595 A1 | 8/2005 | Feldman et al. | 2006/0088567 A1 | 4/2006 | Warner et al. |
| 2005/0177226 A1 | 8/2005 | Banik et al. | 2006/0088653 A1 | 4/2006 | Chappa et al. |
| 2005/0180919 A1 | 8/2005 | Tedeschi | 2006/0088666 A1 | 4/2006 | Kobrin et al. |
| 2005/0182361 A1 | 8/2005 | Lennox | 2006/0100696 A1 | 5/2006 | Atanasoska et al. |
| 2005/0182478 A1 | 8/2005 | Holman et al. | 2006/0115512 A1 | 6/2006 | Peacock et al. |
| 2005/0186250 A1 | 8/2005 | Gertner et al. | 2006/0118236 A1 | 6/2006 | House et al. |
| 2005/0187605 A1 | 8/2005 | Greenhalgh et al. | 2006/0121080 A1 | 6/2006 | Lye et al. |

| | | |
|---|---|---|
| 2006/0122694 A1 | 6/2006 | Stinson et al. |
| 2006/0122697 A1 | 6/2006 | Shanley et al. |
| 2006/0124472 A1 | 6/2006 | Rokicki |
| 2006/0127266 A1 | 6/2006 | Miura et al. |
| 2006/0129215 A1 | 6/2006 | Helmus et al. |
| 2006/0129222 A1 | 6/2006 | Stinson |
| 2006/0129225 A1 | 6/2006 | Kopia et al. |
| 2006/0136048 A1 | 6/2006 | Pacetti et al. |
| 2006/0136051 A1 | 6/2006 | Furst et al. |
| 2006/0141156 A1 | 6/2006 | Viel et al. |
| 2006/0149352 A1 | 7/2006 | Schlun |
| 2006/0153729 A1 | 7/2006 | Stinson et al. |
| 2006/0155361 A1 | 7/2006 | Schomig et al. |
| 2006/0167543 A1 | 7/2006 | Bailey et al. |
| 2006/0177480 A1 | 8/2006 | Sung et al. |
| 2006/0178727 A1 | 8/2006 | Richter |
| 2006/0184235 A1 | 8/2006 | Rivron et al. |
| 2006/0193886 A1 | 8/2006 | Owens et al. |
| 2006/0193887 A1 | 8/2006 | Owens et al. |
| 2006/0193888 A1 | 8/2006 | Lye et al. |
| 2006/0193889 A1 | 8/2006 | Spradlin et al. |
| 2006/0193890 A1 | 8/2006 | Owens et al. |
| 2006/0193892 A1 | 8/2006 | Furst et al. |
| 2006/0195142 A1 | 8/2006 | Shalaby |
| 2006/0198869 A1 | 9/2006 | Furst et al. |
| 2006/0199876 A1 | 9/2006 | Troczynski et al. |
| 2006/0200229 A1 | 9/2006 | Burgermeister et al. |
| 2006/0200231 A1 | 9/2006 | O'Brien et al. |
| 2006/0200232 A1 | 9/2006 | Phaneuf et al. |
| 2006/0200233 A1 | 9/2006 | Kujawski |
| 2006/0204441 A1 | 9/2006 | Atala et al. |
| 2006/0204445 A1 | 9/2006 | Atala et al. |
| 2006/0210595 A1 | 9/2006 | Singhvi et al. |
| 2006/0212108 A1 | 9/2006 | Tittelbach |
| 2006/0222679 A1 | 10/2006 | Shanley et al. |
| 2006/0222844 A1 | 10/2006 | Stinson |
| 2006/0224237 A1 | 10/2006 | Furst et al. |
| 2006/0229711 A1 | 10/2006 | Yan et al. |
| 2006/0229713 A1 | 10/2006 | Shanley et al. |
| 2006/0230476 A1 | 10/2006 | Atanasoska et al. |
| 2006/0233941 A1 | 10/2006 | Olson |
| 2006/0241739 A1 | 10/2006 | Besselink et al. |
| 2006/0251701 A1 | 11/2006 | Lynn et al. |
| 2006/0259133 A1 | 11/2006 | Sowinski et al. |
| 2006/0264138 A1 | 11/2006 | Sowinski et al. |
| 2006/0271156 A1 | 11/2006 | Ledergerber |
| 2006/0271168 A1 | 11/2006 | Kleine et al. |
| 2006/0271169 A1 | 11/2006 | Lye et al. |
| 2006/0271192 A1 | 11/2006 | Olsen et al. |
| 2006/0275554 A1 | 12/2006 | Zhao et al. |
| 2006/0276877 A1 | 12/2006 | Owens et al. |
| 2006/0276878 A1 | 12/2006 | Owens et al. |
| 2006/0276879 A1 | 12/2006 | Lye et al. |
| 2006/0276884 A1 | 12/2006 | Lye et al. |
| 2006/0276885 A1 | 12/2006 | Lye et al. |
| 2006/0280770 A1 | 12/2006 | Hossainy et al. |
| 2006/0287709 A1 | 12/2006 | Rao |
| 2006/0292388 A1 | 12/2006 | Palumbo et al. |
| 2007/0003589 A1 | 1/2007 | Astafieva et al. |
| 2007/0003596 A1 | 1/2007 | Tittelbach et al. |
| 2007/0020306 A1 | 1/2007 | Schultheiss |
| 2007/0027532 A1 | 2/2007 | Wang et al. |
| 2007/0032858 A1 | 2/2007 | Santos et al. |
| 2007/0032862 A1 | 2/2007 | Weber et al. |
| 2007/0032864 A1 | 2/2007 | Furst et al. |
| 2007/0034615 A1 | 2/2007 | Kleine |
| 2007/0036905 A1 | 2/2007 | Kramer |
| 2007/0038176 A1 | 2/2007 | Weber et al. |
| 2007/0038289 A1 | 2/2007 | Nishide et al. |
| 2007/0038290 A1 | 2/2007 | Huang et al. |
| 2007/0045252 A1 | 3/2007 | Kleine et al. |
| 2007/0048350 A1 | 3/2007 | Falotico et al. |
| 2007/0050007 A1 | 3/2007 | Kondyurin et al. |
| 2007/0050009 A1 | 3/2007 | Flanagan |
| 2007/0052497 A1 | 3/2007 | Tada |
| 2007/0055349 A1 | 3/2007 | Santos et al. |
| 2007/0055354 A1 | 3/2007 | Santos et al. |
| 2007/0055364 A1 | 3/2007 | Hossainy et al. |
| 2007/0059435 A1 | 3/2007 | Santos et al. |
| 2007/0065418 A1 | 3/2007 | Vallana et al. |
| 2007/0073385 A1 | 3/2007 | Schaeffer et al. |
| 2007/0073390 A1 | 3/2007 | Lee |
| 2007/0077163 A1 | 4/2007 | Furst et al. |
| 2007/0100385 A1 | 5/2007 | Rawat et al. |
| 2007/0104753 A1 | 5/2007 | Flanagan |
| 2007/0106347 A1 | 5/2007 | Lin |
| 2007/0106363 A1 | 5/2007 | Weber |
| 2007/0123131 A1 | 5/2007 | Nguyen et al. |
| 2007/0123973 A1 | 5/2007 | Roth et al. |
| 2007/0129789 A1 | 6/2007 | Cottone, Jr. et al. |
| 2007/0129792 A1 | 6/2007 | Picart et al. |
| 2007/0134288 A1 | 6/2007 | Parsonage et al. |
| 2007/0135908 A1 | 6/2007 | Zhao |
| 2007/0141106 A1 | 6/2007 | Bonutti et al. |
| 2007/0142897 A1 | 6/2007 | Consigny et al. |
| 2007/0142899 A1 | 6/2007 | Lootz et al. |
| 2007/0148251 A1 | 6/2007 | Hossainy et al. |
| 2007/0151093 A1 | 7/2007 | Curcio et al. |
| 2007/0156231 A1 | 7/2007 | Weber |
| 2007/0156248 A1 | 7/2007 | Marco et al. |
| 2007/0160641 A1 | 7/2007 | Jang |
| 2007/0168016 A1 | 7/2007 | Gronemeyer et al. |
| 2007/0173923 A1 | 7/2007 | Savage et al. |
| 2007/0178129 A1 | 8/2007 | Flanagan |
| 2007/0181433 A1 | 8/2007 | Birdsall et al. |
| 2007/0184083 A1 | 8/2007 | Coughlin |
| 2007/0190104 A1 | 8/2007 | Kamath et al. |
| 2007/0191923 A1 | 8/2007 | Weber |
| 2007/0191928 A1 | 8/2007 | Rolando et al. |
| 2007/0191931 A1 | 8/2007 | Weber et al. |
| 2007/0191943 A1 | 8/2007 | Shrivastava et al. |
| 2007/0197980 A1 | 8/2007 | Barry et al. |
| 2007/0202466 A1 | 8/2007 | Schwarz et al. |
| 2007/0207186 A1 | 9/2007 | Scanlon et al. |
| 2007/0208412 A1 | 9/2007 | Elmaleh |
| 2007/0219626 A1 | 9/2007 | Rolando et al. |
| 2007/0224116 A1 | 9/2007 | Chandrasekaran et al. |
| 2007/0224244 A1 | 9/2007 | Weber et al. |
| 2007/0225799 A1 | 9/2007 | Doty |
| 2007/0244541 A1 | 10/2007 | Schulman |
| 2007/0244569 A1 | 10/2007 | Weber et al. |
| 2007/0250155 A1 | 10/2007 | Simpson |
| 2007/0250156 A1 | 10/2007 | Palmaz |
| 2007/0250158 A1 | 10/2007 | Krivoruchko et al. |
| 2007/0255388 A1 | 11/2007 | Rudakov et al. |
| 2007/0255392 A1 | 11/2007 | Johnson |
| 2007/0264199 A1 | 11/2007 | Labhasetwar et al. |
| 2007/0264303 A1 | 11/2007 | Atanasoska et al. |
| 2007/0270940 A1 | 11/2007 | Doty |
| 2007/0270942 A1 | 11/2007 | Thomas |
| 2007/0281073 A1 | 12/2007 | Gale et al. |
| 2007/0281117 A1 | 12/2007 | Kaplan et al. |
| 2007/0282432 A1 | 12/2007 | Stinson et al. |
| 2007/0299509 A1 | 12/2007 | Ding |
| 2007/0299512 A1 | 12/2007 | Korzuschnik et al. |
| 2008/0003251 A1 | 1/2008 | Zhou |
| 2008/0003256 A1 | 1/2008 | Martens et al. |
| 2008/0003431 A1 | 1/2008 | Fellinger et al. |
| 2008/0004691 A1 | 1/2008 | Weber et al. |
| 2008/0031765 A1 | 2/2008 | Gerold et al. |
| 2008/0033522 A1 | 2/2008 | Grewe et al. |
| 2008/0033530 A1 | 2/2008 | Zberg et al. |
| 2008/0033531 A1 | 2/2008 | Barthel et al. |
| 2008/0033533 A1 | 2/2008 | Borck |
| 2008/0033536 A1 | 2/2008 | Wittchow |
| 2008/0033537 A1 | 2/2008 | Tittelbach |
| 2008/0033538 A1 | 2/2008 | Borck et al. |
| 2008/0033539 A1 | 2/2008 | Sternberg et al. |
| 2008/0033576 A1 | 2/2008 | Gerold et al. |
| 2008/0038146 A1 | 2/2008 | Wachter et al. |
| 2008/0050413 A1 | 2/2008 | Horvers et al. |
| 2008/0051335 A1 | 2/2008 | Kleiner et al. |
| 2008/0051866 A1 | 2/2008 | Chen et al. |
| 2008/0051872 A1 | 2/2008 | Borck |
| 2008/0051881 A1 | 2/2008 | Feng et al. |
| 2008/0057105 A1 | 3/2008 | Atanasoska et al. |
| 2008/0058919 A1 | 3/2008 | Kramer-Brown et al. |
| 2008/0058921 A1 | 3/2008 | Lindquist |

| | | | | | | |
|---|---|---|---|---|---|---|
| 2008/0058923 A1 | 3/2008 | Bertsch et al. | | 2009/0024211 A1 | 1/2009 | Wittchow |
| 2008/0069854 A1 | 3/2008 | Xiao et al. | | 2009/0028785 A1 | 1/2009 | Clarke |
| 2008/0069858 A1 | 3/2008 | Weber | | 2009/0030494 A1 | 1/2009 | Stefanadis et al. |
| 2008/0071348 A1 | 3/2008 | Boismier et al. | | 2009/0030500 A1 | 1/2009 | Weber et al. |
| 2008/0071349 A1 | 3/2008 | Atanasoska et al. | | 2009/0030504 A1 | 1/2009 | Weber et al. |
| 2008/0071350 A1 | 3/2008 | Stinson | | 2009/0030506 A1 | 1/2009 | Klocke et al. |
| 2008/0071351 A1 | 3/2008 | Flanagan et al. | | 2009/0030507 A1 | 1/2009 | Klocke et al. |
| 2008/0071352 A1 | 3/2008 | Weber et al. | | 2009/0035351 A1 | 2/2009 | Berglund et al. |
| 2008/0071353 A1 | 3/2008 | Weber et al. | | 2009/0043330 A1 | 2/2009 | To |
| 2008/0071355 A1 | 3/2008 | Weber et al. | | 2009/0043374 A1 | 2/2009 | Nakano |
| 2008/0071357 A1 | 3/2008 | Girton et al. | | 2009/0043380 A1 | 2/2009 | Blaha et al. |
| 2008/0071358 A1 | 3/2008 | Weber et al. | | 2009/0048660 A1 | 2/2009 | Adden |
| 2008/0082162 A1 | 4/2008 | Boismier et al. | | 2009/0062905 A1 | 3/2009 | Moore, Jr. et al. |
| 2008/0086199 A1 | 4/2008 | Dave et al. | | 2009/0069884 A1 | 3/2009 | Mueller |
| 2008/0086201 A1 | 4/2008 | Weber et al. | | 2009/0076588 A1 | 3/2009 | Weber |
| 2008/0090097 A1 | 4/2008 | Shaw et al. | | 2009/0076596 A1 | 3/2009 | Adden et al. |
| 2008/0097577 A1 | 4/2008 | Atanasoska et al. | | 2009/0081293 A1 | 3/2009 | Murase et al. |
| 2008/0103589 A1 | 5/2008 | Cheng et al. | | 2009/0081450 A1 | 3/2009 | Ascher et al. |
| 2008/0103594 A1 | 5/2008 | Loffler et al. | | 2009/0088831 A1 | 4/2009 | Goto |
| 2008/0107890 A1 | 5/2008 | Bureau et al. | | 2009/0088834 A1 | 4/2009 | Wang |
| 2008/0109072 A1 | 5/2008 | Girton | | 2009/0093871 A1 | 4/2009 | Rea et al. |
| 2008/0113083 A1 | 5/2008 | Sutermeister et al. | | 2009/0095715 A1 | 4/2009 | Sabaria |
| 2008/0124373 A1 | 5/2008 | Xiao et al. | | 2009/0118809 A1 | 5/2009 | Scheuermann et al. |
| 2008/0131479 A1 | 6/2008 | Weber et al. | | 2009/0118812 A1 | 5/2009 | Kokate et al. |
| 2008/0140172 A1 | 6/2008 | Carpenter et al. | | 2009/0118813 A1 | 5/2009 | Scheuermann et al. |
| 2008/0140186 A1 | 6/2008 | Grignani et al. | | 2009/0118814 A1 | 5/2009 | Schoenle et al. |
| 2008/0145400 A1 | 6/2008 | Weber et al. | | 2009/0118815 A1 | 5/2009 | Arcand et al. |
| 2008/0147175 A1 | 6/2008 | Krivoruchko et al. | | 2009/0118818 A1 | 5/2009 | Foss et al. |
| 2008/0147177 A1 | 6/2008 | Scheuermann et al. | | 2009/0118819 A1 | 5/2009 | Merz et al. |
| 2008/0148002 A1 | 6/2008 | Fleming | | 2009/0118820 A1 | 5/2009 | Gregorich et al. |
| 2008/0152929 A1 | 6/2008 | Zhao | | 2009/0118821 A1 | 5/2009 | Scheuermann et al. |
| 2008/0160166 A1 | 7/2008 | Rypacek et al. | | 2009/0118822 A1 | 5/2009 | Holman et al. |
| 2008/0160259 A1 | 7/2008 | Nielson et al. | | 2009/0118823 A1 | 5/2009 | Atanasoska et al. |
| 2008/0161906 A1 | 7/2008 | Atanasoska et al. | | 2009/0123517 A1 | 5/2009 | Flanagan et al. |
| 2008/0171929 A1 | 7/2008 | Katims | | 2009/0123521 A1 | 5/2009 | Weber et al. |
| 2008/0175885 A1 | 7/2008 | Asgari | | 2009/0124956 A1 | 5/2009 | Swetlin et al. |
| 2008/0177378 A1 | 7/2008 | Asgari | | 2009/0131540 A1 | 5/2009 | Hiromoto et al. |
| 2008/0183269 A2 | 7/2008 | Kaplan et al. | | 2009/0143855 A1 | 6/2009 | Weber et al. |
| 2008/0183277 A1 | 7/2008 | Atanasoska et al. | | 2009/0149942 A1 | 6/2009 | Edelman et al. |
| 2008/0183278 A1 | 7/2008 | Atanasoska et al. | | 2009/0157165 A1 | 6/2009 | Miller et al. |
| 2008/0188927 A1 | 8/2008 | Rohde et al. | | 2009/0157172 A1 | 6/2009 | Kokate et al. |
| 2008/0195170 A1 | 8/2008 | Asgari | | 2009/0164002 A1 | 6/2009 | Becher et al. |
| 2008/0195189 A1 | 8/2008 | Asgari | | 2009/0171452 A1 | 7/2009 | Yamamoto et al. |
| 2008/0195198 A1 | 8/2008 | Asgari | | 2009/0177273 A1 | 7/2009 | Piveteau et al. |
| 2008/0208308 A1 | 8/2008 | Allen et al. | | 2009/0182290 A1 | 7/2009 | Harder et al. |
| 2008/0208313 A1 | 8/2008 | Yu et al. | | 2009/0182337 A1 | 7/2009 | Stopek et al. |
| 2008/0208352 A1 | 8/2008 | Krivoruchko et al. | | 2009/0182425 A1 | 7/2009 | Duda et al. |
| 2008/0213377 A1 | 9/2008 | Bhatia et al. | | 2009/0192571 A1 | 7/2009 | Stett et al. |
| 2008/0215129 A1 | 9/2008 | Venturelli et al. | | 2009/0192594 A1 | 7/2009 | Borck |
| 2008/0215139 A1 | 9/2008 | McMorrow et al. | | 2009/0192595 A1 | 7/2009 | Nagura et al. |
| 2008/0215140 A1 | 9/2008 | Borck et al. | | 2009/0192596 A1 | 7/2009 | Adden |
| 2008/0241218 A1 | 10/2008 | McMorrow et al. | | 2009/0196899 A1 | 8/2009 | Birdsall et al. |
| 2008/0243113 A1 | 10/2008 | Shastri et al. | | 2009/0198320 A1 | 8/2009 | Mueller et al. |
| 2008/0243230 A1 | 10/2008 | Lootz et al. | | 2009/0202610 A1 | 8/2009 | Wilson |
| 2008/0243231 A1 | 10/2008 | Flanagan et al. | | 2009/0204203 A1 | 8/2009 | Allen et al. |
| 2008/0243234 A1 | 10/2008 | Wilcox | | 2009/0208428 A1 | 8/2009 | Hill et al. |
| 2008/0243240 A1 | 10/2008 | Doty et al. | | 2009/0208555 A1 | 8/2009 | Kuttler et al. |
| 2008/0243242 A1 | 10/2008 | Kappelt et al. | | 2009/0214373 A1 | 8/2009 | Stinson et al. |
| 2008/0249600 A1 | 10/2008 | Atanasoska et al. | | 2009/0220612 A1 | 9/2009 | Perera |
| 2008/0249615 A1 | 10/2008 | Weber | | 2009/0228037 A1 | 9/2009 | Rego |
| 2008/0255508 A1 | 10/2008 | Wang | | 2009/0240323 A1 | 9/2009 | Wilcox |
| 2008/0255509 A1 | 10/2008 | Wang | | 2009/0254171 A1 | 10/2009 | Heikkila |
| 2008/0262589 A1 | 10/2008 | Nagura | | 2009/0259300 A1 | 10/2009 | Dorogy, Jr. et al. |
| 2008/0268308 A1 | 10/2008 | Schilling et al. | | 2009/0270979 A1 | 10/2009 | Adden |
| 2008/0269872 A1 | 10/2008 | Lootz et al. | | 2009/0274737 A1 | 11/2009 | Borck |
| 2008/0288048 A1 | 11/2008 | Rolando et al. | | 2009/0281613 A1 | 11/2009 | Atanasoska et al. |
| 2008/0290467 A1 | 11/2008 | Shue | | 2009/0287301 A1 | 11/2009 | Weber |
| 2008/0294236 A1 | 11/2008 | Anand et al. | | 2009/0287302 A1 | 11/2009 | Thomas et al. |
| 2008/0294246 A1 | 11/2008 | Scheuermann | | 2009/0306584 A1 | 12/2009 | Schmidtlein et al. |
| 2008/0306584 A1 | 12/2008 | Kramer-Brown | | 2009/0306756 A1 | 12/2009 | Cho et al. |
| 2009/0005862 A1 | 1/2009 | Nakatani et al. | | 2009/0306765 A1 | 12/2009 | Weber |
| 2009/0012599 A1 | 1/2009 | Broome et al. | | 2009/0306766 A1 | 12/2009 | McDermott et al. |
| 2009/0018639 A1 | 1/2009 | Kuehling | | 2009/0311300 A1 | 12/2009 | Wittchow |
| 2009/0018647 A1 | 1/2009 | Benco et al. | | 2009/0312807 A1 | 12/2009 | Boudreault et al. |
| 2009/0018648 A1 | 1/2009 | Wittchow | | 2009/0319035 A1 | 12/2009 | Terry |
| 2009/0022771 A1 | 1/2009 | Lynn et al. | | 2009/0324684 A1 | 12/2009 | Atanasoska et al. |
| 2009/0024199 A1 | 1/2009 | Birdsall et al. | | 2009/0326638 A1 | 12/2009 | Atanasoska et al. |
| 2009/0024209 A1 | 1/2009 | Ozdil et al. | | 2010/0008970 A1 | 1/2010 | O'Brien et al. |
| 2009/0024210 A1 | 1/2009 | Klocke et al. | | 2010/0010621 A1 | 1/2010 | Klocke |

| | | | | | | |
|---|---|---|---|---|---|---|
| 2010/0010640 A1 | 1/2010 | Gerold et al. | | EP | 1 653 885 | 4/2009 |
| 2010/0015206 A1 | 1/2010 | Flanagan et al. | | EP | 1 632 256 | 9/2009 |
| 2010/0016940 A1 | 1/2010 | Shokoohi et al. | | EP | 1 703 858 | 10/2009 |
| 2010/0021523 A1 | 1/2010 | Scheuermann et al. | | EP | 2 139 535 | 1/2010 |
| 2010/0023112 A1 | 1/2010 | Borck et al. | | EP | 1 883 380 | 3/2010 |
| 2010/0023116 A1 | 1/2010 | Borck et al. | | EP | 2 189 169 | 5/2010 |
| 2010/0028436 A1 | 2/2010 | Ohrlander et al. | | JP | 06-306298 | 11/1992 |
| 2010/0030326 A1 | 2/2010 | Radhakrishnan et al. | | JP | 06-292716 | 10/1994 |
| 2010/0034899 A1 | 2/2010 | Harder et al. | | JP | 2003-052834 | 2/2003 |
| 2010/0042205 A1 | 2/2010 | Atanasoska et al. | | JP | 2003-169846 | 6/2003 |
| 2010/0042206 A1 | 2/2010 | Yadav et al. | | JP | 2003-250880 | 9/2003 |
| 2010/0047312 A1 | 2/2010 | Wittchow | | JP | 2003-526386 | 9/2003 |
| 2010/0047324 A1 | 2/2010 | Fritz et al. | | JP | 2004-121827 | 4/2004 |
| 2010/0049146 A1 | 2/2010 | Nielsen et al. | | RU | 2 218 242 | 12/2003 |
| 2010/0049296 A1 | 2/2010 | Sarasam et al. | | WO | 93/04118 | 3/1993 |
| 2010/0049299 A1 | 2/2010 | Popowski et al. | | WO | 97/11724 | 4/1997 |
| 2010/0049300 A1 | 2/2010 | Harder | | WO | 98/29025 | 7/1998 |
| 2010/0055151 A1 | 3/2010 | Flanagan | | WO | 98/48851 | 11/1998 |
| 2010/0057188 A1 | 3/2010 | Weber | | WO | 99/33410 | 7/1999 |
| 2010/0057197 A1 | 3/2010 | Weber et al. | | WO | 99/47077 | 9/1999 |
| 2010/0070024 A1 | 3/2010 | Venturelli et al. | | WO | 99/64580 | 12/1999 |
| 2010/0075162 A1 | 3/2010 | Yang et al. | | WO | 00/25841 | 5/2000 |
| 2010/0076544 A1 | 3/2010 | Hoffmann et al. | | WO | 00/48660 | 8/2000 |
| 2010/0076556 A1 | 3/2010 | Tomantschger et al. | | WO | 00/51136 | 8/2000 |
| 2010/0081735 A1 | 4/2010 | Mao et al. | | WO | 00/54704 | 9/2000 |
| 2010/0082092 A1 | 4/2010 | Gerold | | WO | 00/66190 | 11/2000 |
| 2010/0087910 A1 | 4/2010 | Weber | | WO | 01/32072 | 5/2001 |
| 2010/0087911 A1 | 4/2010 | Mueller | | WO | 01/49338 | 7/2001 |
| 2010/0087914 A1 | 4/2010 | Bayer et al. | | WO | 01/78906 | 10/2001 |
| 2010/0087915 A1 | 4/2010 | Bayer et al. | | WO | 01/80920 | 11/2001 |
| 2010/0087916 A1 | 4/2010 | Bayer et al. | | WO | 01/87371 | 11/2001 |
| 2010/0092535 A1 | 4/2010 | Cook et al. | | WO | 02/39875 | 5/2002 |
| 2010/0106243 A1 | 4/2010 | Wittchow | | WO | 02/45764 | 6/2002 |
| 2010/0119576 A1 | 5/2010 | Harder et al. | | WO | 02/47739 | 6/2002 |
| 2010/0119581 A1 | 5/2010 | Gratz et al. | | WO | 02/053202 | 7/2002 |
| 2010/0121432 A1 | 5/2010 | Klocke et al. | | WO | 02/076523 | 10/2002 |
| 2010/0125325 A1 | 5/2010 | Allen et al. | | WO | 03/002243 | 1/2003 |
| 2010/0125328 A1 | 5/2010 | Flanagan | | WO | 03/013396 | 2/2003 |
| 2010/0131050 A1 | 5/2010 | Zhao | | WO | 03/035123 | 5/2003 |
| 2010/0131052 A1 | 5/2010 | Kappelt et al. | | WO | 03/035131 | 5/2003 |
| 2010/0161031 A1 | 6/2010 | Papirov et al. | | WO | 03/035134 | 5/2003 |
| 2010/0217370 A1 | 8/2010 | Scheuermann et al. | | WO | 03/035278 | 5/2003 |
| | | | | WO | 03/046062 | 6/2003 |
| | FOREIGN PATENT DOCUMENTS | | | WO | 03/063733 | 8/2003 |
| | | | | WO | 03/068285 | 8/2003 |
| AU | 2003 203 722 | 11/2003 | | WO | 03/094990 | 11/2003 |
| CA | 2 235 031 | 10/1998 | | WO | 2004/025332 | 3/2004 |
| CA | 2 346 857 | 5/2000 | | WO | 2004/026361 | 4/2004 |
| CA | 2 371 800 | 8/2000 | | WO | 2004/029313 | 4/2004 |
| DE | 198 11 033 | 8/1999 | | WO | 2004/043292 | 5/2004 |
| DE | 198 56 983 | 12/1999 | | WO | 2004/093643 | 11/2004 |
| DE | 103 57 281 | 7/2005 | | WO | 2005/025449 | 3/2005 |
| DE | 103 61 941 | 7/2005 | | WO | 2005/065576 | 7/2005 |
| DE | 10 2006 38236 | 2/2008 | | WO | 2005/079335 | 9/2005 |
| EP | 0 006 544 | 6/1979 | | WO | 2005/110395 | 11/2005 |
| EP | 0 337 035 | 11/1993 | | WO | 2005/118019 | 12/2005 |
| EP | 0 615 769 | 9/1994 | | WO | 2006/008739 | 1/2006 |
| EP | 0 923 389 | 7/1998 | | WO | 2006/060033 | 6/2006 |
| EP | 0 966 979 | 12/1999 | | WO | 2006/060534 | 6/2006 |
| EP | 0 972 563 | 1/2000 | | WO | 2006/065356 | 6/2006 |
| EP | 1 054 644 | 11/2000 | | WO | 2006/077154 | 7/2006 |
| EP | 1 071 490 | 1/2001 | | WO | 2006/080381 | 8/2006 |
| EP | 1 222 901 | 7/2002 | | WO | 2006/097503 | 9/2006 |
| EP | 1 270 023 | 1/2003 | | WO | 2006/104644 | 10/2006 |
| EP | 1 273 314 | 1/2003 | | WO | 2006/108065 | 10/2006 |
| EP | 1 370 306 | 12/2003 | | WO | 2007/005806 | 1/2007 |
| EP | 0 923 912 | 2/2004 | | WO | 2007/013102 | 2/2007 |
| EP | 1 393 766 | 3/2004 | | WO | 2007/018931 | 2/2007 |
| EP | 1 419 793 | 5/2004 | | WO | 2007/024552 | 3/2007 |
| EP | 0 951 877 | 6/2004 | | WO | 2007/035791 | 3/2007 |
| EP | 1 260 214 | 6/2004 | | WO | 2007/079363 | 7/2007 |
| EP | 0 875 218 | 2/2005 | | WO | 2007/079636 | 7/2007 |
| EP | 1 389 471 | 8/2006 | | WO | 2007/082147 | 9/2007 |
| EP | 1 733 746 | 12/2006 | | WO | 2007/139668 | 12/2007 |
| EP | 1 752 167 | 2/2007 | | WO | 2008/003450 | 3/2008 |
| EP | 1 465 552 | 5/2007 | | WO | 2008/034048 | 3/2008 |
| EP | 1 835 042 | 9/2007 | | WO | 2008/034066 | 3/2008 |
| EP | 1 750 780 | 10/2007 | | WO | 2008/036548 | 3/2008 |
| EP | 1 562 565 | 3/2008 | | WO | 2008/036549 | 3/2008 |
| EP | 1 642 551 | 12/2008 | | | | |

| | | |
|---|---|---|
| WO | 2008/036554 | 3/2008 |
| WO | 2008/062414 | 5/2008 |
| WO | 2008/092436 | 8/2008 |
| WO | 2008/106271 | 9/2008 |
| WO | 2008/117315 | 10/2008 |
| WO | 2008/118606 | 10/2008 |
| WO | 2009/045773 | 4/2009 |

OTHER PUBLICATIONS

Viswanathamurthi et al., "Preparation and morphology of niobuim oxide fibres by electrospinning," *Chemical Physics Letters*, 2003, 374: 79-84.

Authorized Officer Henrique Amaro, International Preliminary Report on Patentability from PCT/US09/043326 mailed Nov. 18, 2010, 7 pages.

Authorized Officer Jasmine Messemanne, International Search Report from PCT/US09/051965 mailed Aug. 20, 2010, 13 pages.

Authorized Officer Jasmine Messemanne, International Preliminary Report on Patentability from PCT/US09/051965 mailed Feb. 10, 2011, 8 pages.

Authorized Officer Antonio Espuch, International Preliminary Report on Patentability in PCT/US09/49422 mailed Jan. 13, 2011, 7 pages.

Authorized Officer Aurore Schneider, International Preliminary Report on Patentability from PCT/US2010/042772 mailed Feb. 4, 2011, 9 pages.

Authorized Officer Henrique Amaro, International Preliminary Report on Patentability in PCT/US2009/43326 mailed Nov. 18, 2010, 7 pages.

Authorized Officer Antoine Laurent, International Preliminary Report on Patentability in PCT/US09/046750 mailed Dec. 23, 2010, 8 pages.

Chou et al., "Electrochemical treatment of mouse and rat fibrosarcomas with direct current," *Bioelectromagnetics*, 1997, 18:14-24.

Li et al., "Effects of Direct Current on Dog Liver: Possible Mechanisms for Tumor Electrochemical Treatment," *Bioelectromagnetics*, 1997, 18:2-7.

*Methods in Cell Biology* (*Cell Death*), vol. 46, p. 163.

James A. Plambeck, "Electrolytic Processes of Nonmetals," *Chemical Sciences*, 1995, 2 pages.

Ren et al., "Variations of dose and electrode spacing for rat breast cancer electrochemical treatment," *Bioelectromagnetics*, 2001, 22(3):205-211.

Stoner et al., "The mechanism of low frequency a.c. Electrochemical Disinfection," *Bioelectrochemistry and Bioenergetics*, 1982, 9:229-243.

Turler et al., "Experimental low-level direct current therapy in liver metastases: influence of polarity and current dose," *Bioelectromagnetics*, 2000, 21(5):395-401.

Xin et al., "Electrochemical Treatment of Lung Cancer," *Bioelectromagnetics*, 1997, 18:8-13.

Yen et al., "Electrochemical treatment of human KB cells in vitro," Bioelectromagnetics, 1999, 20:34-41.

US 6,533,715, 3/2003, Hossainy et al. (withdrawn).

U.S. Appl. No. 10/849,742, filed May 20, 2004, Chen et al.

U.S. Appl. No. 60/826,002, filed Sep. 18, 2006, Girton et al.

U.S. Appl. No. 60/845,136, filed Sep. 15, 2006, Weber and Atanasoska.

U.S. Appl. No. 60/862,318, filed Oct. 20, 2006, Atanasoska et al.

"Best of the ACC Scientific Session 2002," *Rev. Cardiovasc. Med.*, 2002, 3(2):85-104.

"Chapter 2: Corrosion Theory and Corrosion Protection," *EM 1110-2-3400*, 1995, 8 pages.

"Galvanic cell" printout from wikipedia, 5 pages, printed on Aug. 16, 2010.

"Galvanicc corrosion," http://www.corrosion-doctors.org/aiscraft/galvdefi.htm, 3 pgs,, printed Oct. 28, 2005.

"Galvanic series" printout from Wikipedia, p. 1 of 2, printed Oct. 28, 2005.

Aaltonen, "Atomic Layer Deposition of Noble Metal Thin Films," *University of Helsinki*, Apr. 8, 2005, pp. 1-71.

Aghion et al., "Newly Developed Magnesium Alloys for Powertrain Applications," *JOM*, 2003, p. 30.

Albion Research Notes, Newsletter, Oct. 1994, 3(4): 1-4.

Anand et al., "Ion-exchange resins: carrying drug delivery forward," DDT, 2001, 6: 905-914.

Anderson et al., "A new conductive polymer as a replacement for chrome conversion coatings," *2003 Aerospace Coatings Removel and Coatings Conference*, May 20-22, 2003, Colorado Springs, CO, 7 pages.

Andión et al., "Corrosion behaviour at the interface of steel bars embedded in cement slurries Effect of phenol polymer coatings," *Corrosion Science*, 2002, 44:2805-2816.

Antipov et al., "Polyelectrolyte Multilayer Capsule Permeability Control," *Colloids and Surfaces A: Physiochem. Eng. Aspects*, 2002, 198-200, 535-541.

Antipov et al., "Polyelectrolyte Multilayer Capsules as Vehicles with Tunable Permeability", *Advances in Colloid and Interface Science*, 2004, 111: 49-61.

Arts et al., "Polyphenols and disease risk in epidemiologic studies," *Am. J. Clin. Nutr.*, 2005, 81:317S-325S.

Artyukhin et al., "Layer-by-Layer Electrostatic Self-Assembly of Polyelectrolyte Nanoshells on Individual Carbon Nanotube Templates," *Langmuir*, 2004, 20:1442-1448.

Ashtari et al. "An efficient method for recovery of target ssDNA based on amino-modified silica-coated magnetic nanoparticles" *Talanta 67.* (2005). 548-554.

Atta, "Electrochemical synthesis, characterization and some properties of a polymer derived from thioflavin S.," *European Polymer Journal*, 2005, 41: 3018-3025.

Australian Government, Department of Health and Aging, "Horizon Scanning Prioritising Summary-Biodegradable stents for coronary artery disease," *Australia and New Zealand Horizon Scanning Network (ANZHSN)*, Aug. 2007, pp. 1-13.

Authorized Officer Athina Nickitas-Etienne, International Preliminary Report on Patentability in PCT/US07/78449 mailed Mar. 26, 2009, 9 pages.

Authorized Officer Athina Nickitas-Etienne, International Preliminary Report on Patentability in PCT/US07/79841 mailed Apr. 30, 2009, 7 pages.

Authorized officer Athina Nickitas-Etienne, International Preliminary Report on Patentability in PCT/US08/86639 mailed Jun. 24, 2010, 2 pages.

Authorized Officer Cecilia Giel-Barragan Ramos, International Search Report/Written in PCT/US07/79841 mailed Feb. 4, 2009, 11 pages.

Authorized Officer Elisabeth Reinecke, International Search Report/ Written Opinion in PCT/US07/60137 mailed Jul. 27, 2007, 20 pages (656W01).

Authorized Officer Joëlle Gerber, International Search Report/Written Opinion in PCT/US07/78450 mailed Nov. 19, 2008, 17 pages.

Authorized Officer Joëlle Gerber, International Search Report/Written Opinion in PCT/US07/88888 mailed Jul. 13, 2009, 24 pages.

Authorized Officer Nora Lindner, International Preliminary Report on Patentability in PCT/US07/88888 mailed Jul. 30, 2009, 11 pages.

International Search Report/Written Opinion in PCT/US2008/86639 mailed Feb. 23, 2010, 8 pages.

Authorized Officer Simin Baharlou, International Preliminary Report on Patentability in PCT/US07/66568 mailed Oct. 23, 2008, 10 pages.

Authorized Officer Simin Baharlou, International Preliminary Report on Patentability in PCT/US07/75072 mailed Feb. 12, 2009, 9 pages.

Authorized Officer Trudy Hinterwimmer, International Search Report/Written Opinion in PCT/US07/78412 mailed Mar. 3, 2008, 10 pages.

Authorized Officer Trudy Hinterwimmer, International Search Report/Written Opinion in PCT/US09/49422 mailed Aug. 24, 2009, 10 pages.

Authorized Officer Véronique van Loon-Mégard, International Search Report/Written Opinion in PCT/US08/75976 mailed Nov. 25, 2008, 20 pages.

International Search Report/Written Opinion in PCT/US2009/43326 mailed Aug. 6, 2009, 9 pages.

Babapulle and Eisenberg, "Coatred stents for their prevention of restenosis: Part II," *Circulation*, 2021, 106: 2849-2866.

Bach et al., "Corrosion, Protection and Repassivation After the Deformation of Magnesium Alloys Coated With a Protective Magnesium Fluoride Layer," *JOM*, 2004, p. 343.

Bakkar et al., "Improving corrosion resistance of magnesium-based alloys by surface modification with hydrogen by electrochemical ion reduction (EIR) and by plasma immersion ion implantation (PIII)," *Corrosion Science*, 2005, 47:1211-1225.

Balasubramanian et al. "Dispersion and Stability Studies of Resorcinarene-Encapsulated Gold Nanoparticles." *Langmuir*, 2002, 1676-3681.

Bao, Y. et al. "Preparation of functionalized and gold-coated cobalt nanocrystals for biomedical applications." *Journal of Magnetism and Magnetic Materials*, 2005, 293:15-19.

Baurschmidt et al., "The Electrochemical Aspects of the Thrombogenicity of a Material," *J. Bioengineering*, 1977, 1:261-278.

Bekesi et al., "Efficient Submircon Processing of Metals with Femto," *Appl. Phys. A.*, Published Oct. 25, 2002, pp. 355-357.

Ben-Hamu et al., "Influence of Si, Ca and Ag addition on corrosion behaviour of new wrought Mg-Zn alloys," *Materials Science and Technology*, 2006, vol. 22, No. 10, pp. 1213-1218.

Bereket et al., "Electrochemical synthesis and anti-corrosive properties of polyaniline, poly(2-anisidine), and poly(aniline-co-2-anisidine) films on stainless steel," *Progress in Organic Coatings*, 2005, 54: 63-72.

Berkland et al., "Controlling Surface Nano-structure Using Flow-Limited Field-Injection Electrostatic Spraying (FFESS) of poly(D,L-lactide-co-glycolide)," *Biomaterials*, 2004, 25:5649-5658.

Bernkop-Schnurch, "Chitosan and its derivatives: potential excipients for peroral peptide delivery systems," *International J. of Pharmaceutics*, 2000, 194: 1-13.

Berry et al., "Functionalisation of magnetic nanoparticles for applications in biomedicine," *J. Phys. D; Appl. Phys.*, 2003, 36:R198-R206.

Biercuk et al., "Low-temperature atomic-layer-deposition lift-off method for microelectronic and nanoelectronic applications," *Applied Physics Letters*, vol. 83, No. 12, Sep. 22, 2003, pp. 2405-2407.

Blanusa et al., "Chelators as Antidotes of Metal Toxicity Therapeutic and Experimental Aspects," *Current Medicinal Chemistry*, 2005, vol. 12, pp. 2771-2794.

Bolz et al., "Effect of smooth, porous and fractal surface structure on the properties of an interface," *J. Materials Science: Materials in Medicine*, 1995, 844-848.

Bosiers et al., "Absorbable Metal stent for CLI in Infrapopliteal lesions: 1 year results," *CX 2005 Global Endovascular Forum*, Apr. 2005, pp. 1-23.

Brandau et al., "Nanoporous Ceramic Coatings for Synthesis of Radioactive Implants," *Journal of Nuclear Medicine Abstract Book*, Jun. 7, 2000, p. 244P, Abstract No. 1076.

Brückner et al., "Metal plasma immersion ion implantation and deposition (MPIIID): chromium on magnesium," *Surface and Coatings Technology*, 1998, 103-104, pp. 227-230.

Brunatto and Muzart, "Influence of the gas mixture flow on the processing parameters of hollow cathode discharge ion sintering," *J. Phys. D.: Appl. Phys.*, 2007, 40: 3937-3944.

Brunner et al., "Porosity Tailored Growth of Black Anodic Layers on Magnesium in an Organic Electrolyte," *Journal of the Electrochemical Society*, vol. 156 (2), Dec. 12, 2008, pp. C62-C66.

Buescher et al., "Characterization of Wet-Chemically Nanostructured Stainless Steel Surfaces," *Mat. Res. Soc. Symp. Proc.*, 2001, 676:1-6.

Caruso et al., "Ultrathin Molybdenum Polyoxometalate-Polyelectrolyte Multilayer Films," *Langmuir*, 1998, 14:3462-3465.

Casan-Pastor et al., "Polyoxometalates: From Inorganic Chemistry to Materials Science," *Frontiers in Bioscience*, 2004, 9:1759-1770.

Chaieb et al., "Inhibition of the corrosion of steel in 1 M HC1 by eugenol derivatives," *Applied Surface Science*, 2005, 246:199-206.

Chang et al., "Effect of Heat Treatment on Corrosion and Electrochemical behavior of Mg-3Nd-0.2Zn-0.4Zr (wt. %) alloy," *Science Direct, Electrochimica Acta 52*, 2007, 3160-3167.

Chang et al., "Templated sythesis of Gold-iron Alloy nanoparticles using pulsed laser deposition," *Nanotechnology*, vol. 17, 2006, pp. 5131-5135.

Changwen et al., "Polyoxometalate-based organic-inorganic hybrid materials," 2004, *Sol-Gel*, p. 1.

Chen et al., "Laser Cladding of Mg20A18o Powder on ZM5 Magnesium Alloy," *Corrosion Engineering, Science and Technology*, 2007, vol. 42, No. 2, pp. 130-136.

Cheng et al., "Electrogeneration and electrochemical properties of hybrid materials: polypyrrole doped with polyoxometalates $PW_{12-x}Mo_xO_{40}{}^{3-}$(x=0,3,6,12)," *Synthetic Metals*, 2002, 129: 53-59.

Cho et al., "Gold-coated iron nanoparticles: a novel magnetic resonance agent for $T_1$ and $T_2$ weighted imaging," *Nanotechnology*, vol. 17, 2006, pp. 640-644.

Clemente-Leon et al., "Hybrid Langmuir-Blodgett Films Formed by Alternating Layers of Magnetic Polyoxometalate Clusters and Organic Donor Molecules—Towards the Preparation of Multifunctional Molecular Materials," *Adv. Mater.*, 2001, 13:574-577.

Cogger et al. "An Introduction to Electrochemical Impedance Measurement," *Solartron Analytical*, 1999, 2-14.

Conolly et al., "X-Ray microtomography studies of localized corrosion and transitions to stress corrosion cracking," *Materials Science and Technology*, 2006, vol. 22, No. 9, pp. 1076-1085.

Costa et al., "The effect of the magnetic field on the corrosion behavior of Nd-Fe-B permanent magnets." *Journal of Magnetism and Magnetic Materials*, 278, 2004, pp. 348-358.

Damen et al., "Paclitaxel esters of malic acid as prodrugs with improved water solubility," *Bioorganic & Medicinal Chemistry*, 2000, 8: 427-432.

Damiani et al., "Vasorelaxant effects on eugenol on rat thoracic aorta," *Vascular Pharmacol.*, 2003, 40:59-66.

Davies, "Changing the salt, changing the drug," *The Pharmaceutical Journal*, 2001, 266: 322-323.

De Geest et al., "Self-rupturing Microcapsules," *Adv. Mater.*, 2005, vol. 17, pp. 2357-2361.

de Witte, "Analysis of the principal component of external casing corrosion in deep wells," *J. Appl. Electrochem.*, 1985, 15: 325-334.

Dexter, "Galvanic Corrosion," MAS Note, University of Delaware Sea Grant Marine Advisory Service, 2003.

Di Mario et al., "Drug-eluting bioabsorbable magnesium stent," *J. Interventional Cardiol.*, 2004, 17(6): 391-395.

Di Mario et al., "MOONLIGHT: a controlled registry of an iridium oxide-coated stent with angiographic follow-up," *Int. J. Cardiol.*, 2004, 95:329-331.

Dowling et al., "Anti-bacterial silver coatings exhibiting enhanced activity through the addition of Platinum," *Surf. & Coatings Tech.*, 2003, 163-164:637-640.

Duncan et al., "Polymer-drug conjugates, PDEPY and PELT: basic principles for design and transfer from the laboratory to clinic," *Journal of Controlled Release*, 2001, 74: 135-146.

Duncan, "The dawning era of polymer 360 therapeutics," *Nature Reviews/Drug Discovery*, 2003, 2: 347-360.

Duygu, "*Controlled Release Systems*," http://www.biomed.metu.edu.tr/courses/term_papers/contr-ret-sys_daygu.htm (Dec. 30, 2005).

Eggebrecht et al., "Novel Magnetic Resonance-Compatible Coronary Stent: The Absorbable Magnesium-Alloy Stent," *Circulation*, 2005, 112: 303-304.

Eniola et al., "Characterization of Biodegradable Drug Delivery Vehicles with the Adhesive Properties of Leukocytes II: Effect of Degradation on Targeting Activity," *Biomaterials*, 26:661-670.

Erbel et al., "Absorbierbare Stents-Eine Vielversprechende Neuerung?" *Urban & Vogel*, No. 4, 2007, pp. 308-319.

Erbel et al., "Temporary scaffolding of coronary arteries with bioabsorbable magnesium stents: a prospective, non-randomised multicentre trial," *Lancet*, 2007, vol. 369, pp. 1869-1875.

Erne et al., "The Road to Bioabsorbable Stents: Reaching Clinical Reality?" *Cardio Vascular and Interventional Radiology*, Sep. 26, 2005, pp. 11-16.

International Preliminary report on Patentability received in PCT/US2007/078417, mailed Mar. 26, 2009, 8 pages.

International Preliminary Report on Patentability, received in PCT/US2007/078407, mailed Mar. 26, 2009, 6 pages.
European Search Report from EP 10159664.1, mailed Jun. 4, 2010, 3 pages.
International Preliminary Report on Patentability in PCT/US05/16600 mailed Nov. 30, 2006, 7 pages.
International Search Report/Written Opinion in PCT/US05/16600 mailed May 4, 2006, 15 pages.
International Preliminary Report on Patentability in PCT/US07/78476 mailed Mar. 26, 2007, 7 pages.
International Preliminary Report on Patentability in PCT/US07/78411 mailed Feb. 4, 2009, 8 pages.
International Preliminary Report on Patentability in PCT/US07/78412 mailed Apr. 2, 2009, 7 pages.
International Preliminary Report on Patentability in PCT/US07/78505 mailed Mar. 26, 2009, 7 pages.
International Preliminary Report on Patentability in PCT/US07/78450 mailed Mar. 26, 2009, 7 pages.
Falotico, "Cordis Fully Bioabsorbable Stent Program," *Euro PCR09*, May 22, 2009, pp. 1-21.
Fan et al., "Influence of Lanthanum on the microstructure, mechanical property and corrosion resistance of magnesium alloy," *J. Mater Sci*, 2006, vol. 41, pp. 5409-5416.
Fan et al., "Metallic Stents Coated with Bioabsorable Polymers," *Cardiac Interventions Today*, Jun./Jul. 2009, pp. 42-49.
Farhat et al., "Corrosion Control Using Polyelectrolyte Multilayers," *Electrochemical and Solid State Letters*, 2002, 5(4):B13-B15.
Feng et al., "Sonochemical preparation of photochromic nanocomposite thin film based on polyoxometalates well dispersed in polyacrylamide," *Journal of Solid State Chemistry*, 2002, 169: 1-5.
Feng et al., "Superplasticity and texture of SiC whiskers in a magnesium-based compposite," *Scripta Materialia*, 2005, 53:361-365.
Ferguson et al., "Corrosion—Fatigue Performance of Magnesium Alloys," *International Journal of Modern Physics B*, vol. 17, Nos. 8 & 9, 2003, pp. 1601-1607.
Ferrando, "Review of Corrosion and Corrosion Control of Magnesium Alloys and Composites," *J. Mater. Eng.*, 1989, 11:299-313.
Fischer et al., "Determination of in-vivo corrosion rates of degradable implants by SR-microtomography," date unknown, pp. 1-2.
Fischer et al., "Hydrogen in magnesium alloys and magnesium interfaces: preparation, electronic properties and interdiffusion," *J. Less-Common Metals*, 1991, 172:808-815.
Fontenier et al., "Study of a 'Platinum-Magnesium' Cell to Supply Current to a Pacemaker," *Bioelectrochemistry and Bioenergetics*, 1975, 2(2):106-123.
Franhofer Institut Fertigungstechnik Material forschung, Evaluation of metal injection moulding (MIM) and extrusion as processing technology for biodegradable stents (A 208143), 8 pages.
Franhofer Institut Fertigungstechnik Material forschung, "Phase 2: Evaluation of mictoextrusion," 4 pages.
Fraunhofer EZRT, "Quantitative material analysis by dual energy computed tomography for industrial NDT applications," 2009, 1 pg.
Fraunhofer IIS—Poster (German), "Prinzip der hochauflosenden Comptuertomographie," 2009, 1 page.
Frei, "On the Role of Vitamin C and Other Antioxidants in Atherogenesis and Vascular Dysfunction," *Proceedings—Society for Experimental Biology and Medicine*, 1999, 222:196-204.
Gabrielli, Claude. "Use and Applications of Electrochemical Impedance Techniques," *Solartron Analytical*, 1997, 1-102.
Garner et al., "Polypyrrole-heparin composites as stimulus-responsive substrates for endothelial cell growth," *J. Biomed. Mater. Res.*, 1999, 44: 121-129.
Gettleman et al., "Measurement of in vivo corrosion rates in baboons, and correlation with in vitro tests," *Journal of Dental Research*, 1980, 59: 689-707.
Gettleman et al., "Materials Science: Measurement of in vivo Corrosion Rates in Baboons, and Correlation with in vitro Tests," *Journal of Dental Research*, 1980, vol. 59, pp. 689-707.
Gomes et al., "Alternative tissue engineering scaffolds based on starch: processing methodologies, morphology, degradation and mechanical properties," *Materials Science and Engineering C*, 2002, 20:19-26.
Grassi et al., "Short-term administration of dark chocolate is followed by a significant increase in insulin sensitivity and a decrease in blood pressure in healthy persons," *Am. J. Clin. Nutr.*, 2005, 81(3):611-614.
Gray and Luan, "Protective coatings on magnesium and its alloys—a critical review," *J. Alloys Compounds*, 2002, 336:88-113.
Griffiths et al., "Future devices: bioabsorbable stents," *Br. J. Cardiol. (Acute & Interventional Cardiology)*, 2004, 11: AIC80-AIC84.
Grube, "Bioabsorbable Stents—The Boston Scientific & REVA Technology," *EuroPCR 2009*, 2009, pp. 1-27.
Gu et al., "In vitro Corrosion and biocompatibility of binary magnesium alloys," *Biomaterials*, vol. 30, 2009, pp. 484-498.
Guo et al., "Manipulation of single-wall carbon nanotubes into aligned molecular layers," *Chem. Phys. Lett.*, 2002, 362:314-318.
Guo et al., "Multi-layer LB films of single-wall carbon nanotubes," *Physica B*, 2002, 323:235-236.
Gupta et al., "Nanometer spaced electrodes using selective area atomic layer deposition," *Applied Physics Letters*, vol. 90, 2007, pp. 1-4.
Gurib-Fakim, "Medicinal plants: Traditions of yesterday and drugs of tomorrow," *Molecular Aspects of Medicine*, 2006, 27:1-93.
Haenzi et al., "Design strategy for microalloyed ultra-ductile Mg alloys," 2009, *Phil. Mag. Letters*, 89(6): 377-390.
Haenzi et al., "Design strategy for new biodegradable Mg-Y-Zn alloys for medical applications," *Int. J. Mat. Res.*, 2009, 100: 1127-1136.
Haenzi et al., "On the biodegradation performance of an Mg-Y-RE alloy with various surface conditions in simulated body fluid," *Acto Biomat.*, 2009, 5: 162-171.
Haferkamp et al., "Magnesium-Base-Alloys as Implant-Material Steps to the Production of Thin Components," *Magnesium*, 2000, 159-164.
Hamu et al., "Influence of Si, Ca and Ag addition on corrosion behavior of new wrought Mg-Zn alloys," 2006, 22(10): 1213-1218.
Hänzi et al., "Design strategy for microalloyed ultra-ductile magnesium alloys," *Philosophical Magazine letters*, vol. 89, No. 6, Jun. 2009, pp. 377-390.
Hänzi et al., "Design strategy for new biodegradable Mg-Y-Zn alloys for medical applications," *Int. J. Mat. Res.*, vol. 100, 2009, pp. 1127-1136.
Hänzi et al., "On the biodegradation performance of an Mg-Y-Re alloy with various surface conditions in simulated body fluid," *Acta Biomaterialia*, vol. 5, 2009, pp. 162-171.
Haque et al. "Bioabsorption Qualities of Chitosan-absorbable Vascular Templates," *Current Surgery*, 2001, 58(1): 77-80.
Hau et al., "Surface-Chemistry Technology for Microfluidics," *J. Micromech. Microeng.*, 2003.13:272-278.
Heismann et al., "Density and atomic number measurements with spectral x-ray attenuation method," *Journal of Applied Physics*, vol. 94, No. 3, Aug. 1, 2003, pp. 2073-2079.
Hermawan et al., "Developments in metallic 1693-1697 biodegradable stents," *Acta Biomaterialia*, 2010, 6: 1693-1697.
Hermawan et al., "Degradable metallic biomaterials: Design and development of Fe-Mn alloys for stents," *Wiley InterScience: Article*, Apr. 19, 2008, pp. 1-12.
Hermawan et al., "Degradation Behaviour of Metallic Biomaterials for Degradable Stents," *Advanced Materials Research*, 2007, 15-17:113-118.
Hermawan et al., "Development of Degradable Fe-35Mn Alloy for Biomedical Application," *Advanced Material Research*, 2007, 15-17:107-112.
Hermawan et al., "Fe-Mn Alloys for Metallic Biodegradable Stents: Degradation and Cell Viability Studies," *Acta Biomaterialia*, Manuscript, Mar. 27, 2009, pp. 1-30.
Hermawan, et al., "Iron-Manganese: new class of metallic degradable biomaterials prepared by powder metallurgy," *Powder Metallurgy*, 2008, 51(1):38-45.
Heublein et al., "Biocorrosion of magnesium alloys: a new principle in cardiovascular implant technology?" *Heart*, 2003, 89:651-656.
Heublein et al., "Degradation of Metallic Alloys—A New Principle in Stent Technology?" *The American Journal of Cardiology, Eleventh Annual Symposium Transcatheter Cardiovascular Therapeutics Abstracts*, Sep. 22, 1999.

Heublein et al., "Bio-corrosion—a new principle for temporary cardiovascular implants?" *European Heart Journal, Journal of the European Society of Cardiology*, 2000, vol. 21, p. 286, Abstract No. P1605

Heublein et al., "Local Tissue Engineering by Biocorrosion Vision or Reality?" *The American Journal of Cardiology, TCT Abstracts/Poster*, Oct. 16, 2000.

Hildebrandt et al., "Prevention of surface encrustation of urological implants by coating with inhibitors," *Biomaterials*, 2001, 22:503-507.

Holclajtner-Antunovic et al., "Study of some polyoxometallates of Keggin's type as potention antitumour agents," *Jugoslov Med. Biohem.*, 2004, 23: 25-30.

Hourng et al., Influence of multisteps thermal control in metal powder injection moulding process, *Powder Metallurgy*, 2008, 51: 84-89.

Huang et al., "A Review on Polymer Nanofibers by Electro-spinning and their Applications in Nanocomposites," 2003, 63:2223-2253.

Hutten, A. et al. "Ferromagnetic FeCo nanoparticles for biotechnology". (2005) *Journal of Magnetism and Magnetic Materials* 293:93-101).

Iakovou et al., "Incidence, Predictors, and Outcome of Thrombosis Successful Implantation of Drug-Eluting Stents," *JAMA*, 2005, 293(17): 2126-2130.

Ignat et al., "Magnesium alloys (WE43 and ZE41) characterization for laser applications," *Applied Surface Science*, 2004, 233:382-391.

Iida et al. "Surface modification of of λFe2O3 nanoparticles with aminopropylsilyl groups and interparticle linkage with with a,w-Dicarboxylic Acids". *Electrochimica Acta*. 2005. 855-859.

Imgrund, "Evaluation of metal injection moulding (MIM) and extrusion as processing technology for biodegradable stents. A 208143: Final report for phase I MIM of Fe and Fe-Si powders and sample characterisation," Aug. 15, 2008, *Fraunhofer Institut Fertigungstechnik Material forschung*, 18 pages.

Integran, "Biodegradable Nanometallic Intracoronary Stents," May 12, 2009, 1 page.

Integran, "Biodegradable Nanometallic Intracoronary Stents," Proposal, May 12, 2009, 1 page.

International Preliminary Report on Patentability in PCT/US07/60137 mailed Jul. 17, 2008, 7 pages.

International Preliminary Report on Patentability in PCT/US07/73839 mailed Apr. 2, 2009.

International Preliminary Report on Patentability in PCT/US07/78429 mailed Apr. 2, 2009.

International Preliminary Report on Patentability in PCT/US07/78475 mailed Mar. 26, 2009, 8 pages.

International Preliminary Report on Patentability received in PCT/US2007/078479, mailed Mar. 26, 2009, 8 pages.

International Search Report / Written Opinion in PCT/US09/046750 mailed Jul. 20, 2010, 14 pages.

International Search Report and Written Opinion in PCT/US07/78449, mailed Jan. 13, 2009, 15 pages.

International Search Report and Written Opinion in PCT/US07/78475, mailed Feb. 4, 2009, 14 pages.

International Search Report and Written Opinion in PCT/US07/78476, mailed Jan. 28, 2009, 29 pages.

International Search Report and Written Opinion mailed Jan. 25, 2008 in PCT/US07/75072, 14 pages.

International Search Report and Written Opinion received in PCT/US2007/078417, mailed Jan. 22, 2009, 18 pages.

International Search Report and Written Opinion received in PCT/US2007/078479, mailed Dec. 30, 2008, 12 pages.

International Search Report for PCT/US05/16600 mailed May 4, 2006, 4 pages.

International Search Report for PCT/US07/66568 dated Oct. 8, 2007, 15 pages.

International Search Report from PCT/US 03/20215, mailed Nov. 11, 2003, 4 pages.

International Search Report/Written Opinion in PCT/US07/73839 mailed Apr. 16, 2008, 16 pages.

International Search Report/Written Opinion in PCT/US07/78411 mailed Mar. 6, 2008, 12 pages.

International Search Report/Written Opinion in PCT/US07/78429 mailed Mar. 28, 2008, 14 pages.

International Search Report/Written Opinion in PCT/US07/78505 mailed Mar. 4, 2008, 10 pages.

International Search Report/Written Opinion in PCT/US2007/078407, mailed Mar. 26, 2008, 10 pages.

Ito et al., "Antioxidant action of eugenol compounds; role of metal ion in the inhibition of lipid peroxidation," *Food Chem. Toxicol.*, 2005, 43:461-466.

Ivanova and Ivanov, "Mechanisms of the extracellular antioxidant defend," *Experimental Pathology and Parasitology*, 2000, 4:49-59.

Jabara et al., "Bioabsorbable Stents: The Future is Near," *Cardiac Interventions Today*, Jun./Jul. 2009, pp. 50-53.

Jabara, "Poly-anhydride based on salicylic acid and adipic acid anhydride," Glimpse into the future: bioabsorbable stents-aimint to restore vascular integrity, *Euro PCR09*, 2009, pp. 1-34.

Jiang et al., "Corrosion protection of polypyrrole electrodeposited on AZ91 magnesium alloys in alkaline solutions," *Synthetic Materials*, 2003, 139: 335-339.

Jiang et al., "Effect of $TiB_2$ particulate on partial remelting behavior of Mg-11A1-0.5Zn matrix composite," *Materials Science and Engineering A*, 2004, 381: 223-229.

Jiang, "A review of wet impregnation—An alternative method for the fabrication of high performance and nano-structured electrodes of solid oxide fuel cells," *Materials Science and Engineering A*, 2006, 418:199-210.

Kaesel et al., "Approach to Control the Corrosion of Magnesium by Alloying," *Magnesium: Proceedings of the 6th International Conference Magnesium Alloys and Their Applications*, 2004, pp. 534-539.

Kainer, "Magnesium alloys and technology," Wiley VCH, 2003, 119 pages.

Kaya et al., "Microstructure and Corrosion Resistance of Alloys of the Mg-Zn-Ag System," *Metal Science and Heat Treatment*, 2006, 48(11-12): 524-530.

Kean and Davies, "Cathodic Protection," 7 pages, 1981; http://www.npl.co.uk/upload/pdf/cathodic_protection.

Kececioglu, "Zur Biokompatibilitat eines neu entwickelten Stentmaterials aus korrodierbarem Reineisen," Jan. 25, 2007, pp. 1-131, *Ruhr-Universitat-Bochum*.

Kidambi et al., "Selective depositions on polyelectrolyte multilayers: self-assembled monolayers of m-dPEG acid as molecular template," *J. Am. Chem. Soc.*, 2004, 126: 4697-4703.

Kim et al., "Comprehensive study on vitamin C equivalent antioxidant capcity (VCEAC) of various polyphenols in scavenging a free radical and its structural relationship," *Crit. Rev. Food Sci. Nutr.*, 2004, 44(4):253-273.

Kim et al., "Effect of Anti-Oxidant (Carvedilol and Probucol) Loaded Stents in a Porcine Coronary Restenosis Model," *Circ. J.*, 2005, 69:101-106.

Kokubo et al., "How useful is SBF in predicting in vivo bone bioactivity?" *Biomaterials*, 2006, 27: 2907-2915.

Kong et al., "Polyelectrolyte-functionalized multiwalled carbon nanotubes: preparation, characterization and layer-by-layer self assembly," *Polymer*, 2005, 46:2472-2485.

Kumar et al., "Polyanhydrides: an overview," *Advanced Drug Delivery Reviews*, 2002, 54:889-910.

Kurth et al., "Multilayer on Solid Planar Substrates: From Structure to Function", *Multi-layer Thin Films Sequential Assembly of Nanocomposite Materials*, 2003, Chapter 14, pp. 393-426.

Kurth et al., "Ultrathin Composite Films Incorporating the Nanoporous Isopolyoxomolybdate 'Keplerate' $(NH_4)_{42}[Mo_{132}O_{372}(CH_3COO)_{30}(H_2O)_{72}]$," *Chem. Mater.*, 2000, 12:2829-2831.

Kutsenko et al., "Structural Changes in Mg Alloy induced by plasma immersion ion implantation of Ag," *Acta Materialia*, 2004, 52:4329-4335.

LaFont, "Arterial Remodeling Technologies: Bioresorbable Stents," *Euro PCR09*, 2009, pp. 1-28.

Lambert et al., "Inhibition of carcinogenesis by polyphenols: evidence from laboratory investigations," *Am. J. Clin. Nutr.*, 2005, 81(suppl):284S-291S.

Lee et al., "Retentive and compressive strengths of modified zinc oxide-eugenol cements," *J. Dentistry*, 2000, 28:69-75.

Lee, J. et al. "Simple synthesis of mesoporous carbon with magnetic nano particles embedded in carbon rods". (2005) Carbon 43:2536-2543.

Lee, Sang-Yup et al. "Surface modification of magentic nanoparticles capped by oleic acids: Characterization and colloidal stability in polar solvents" *Journal of Colloid and Interface Science* 293 (2006) 401-408.

Levesque et al., "Design of pseudo-physiological test bench specific to the development of biodegradable metallic biomaterials," *Acta Biomaterialia*, 2008, 4:284-295.

Li et al., "Photoacoustic Tomography and Sensing in Biomedicine," *Phys. Med. Biol.*, 2009, 54:59-97.

Li, "Poly(L-glutamic acid)-anticancer drug conjugates," *Advanced Drug Delivery Reviews*, 2002, 54: 695-713.

Liao et al., "Fabrication of porous biodegradable polymer scaffolds using a solvent merging/particulate leaching method," *J. Biomed. Mater. Res.*, 2002, 59:676-681.

Lin et al., "Micropatterning proteins and cells on polylactic acid and poly(lactide-*co*-glycolide)," *Biomaterials*, 2005, 26:3655-3662.

Liu et al., "Characterizations of polypyrrole (PPy) nano-tubules made by templated ac electropolymerization," *European Polymer Journal*, 2005, 41: 2117-2121.

Liu et al., "Layer-By-Layer Ionic Self-Assembly of Au Colloids Into Multilayer Thin-Films with Bulk Metal Conductivity," *Chemical Physics Letters*, 1998, 298:315-319.

Liu et al., "Functional Polyoxometalate Thin Films via Electrostatic Layer-by-Layer Self-Assembly," *Journal of Cluster Science*, 2003, 14:405-419.

Liu et al., "Sol-gel deposited TiO2 film on NiTi surgical alloy for biocompatibility improvement," *Thin Solid Films*, 2003, 429:225-230.

Liu, *Introduction to Corrosion and Protection*, Corrosion and Protection Centre, School of Materials, The University of Manchester, 2006, 36 pages.

Lu et al. "Magnetic Switch of Permeability for Polyelectrolyte Microcapsules Embedded with Co@Au Nanoparticles". *American Chemical Society*. 2004.

Lu et al., "Theoretical analysis of calcium phosphate precipitation in simulated body fluid," *Biomaterials*, 2005, 26:1097-1108.

Maeng et al., "Negative Vascular Remodelling after Implantation of Bioabsorbable Magnesium Alloy Stents in Porcine Coronary Arteries: A randomized Comparison with Bare-Metal and Sirolimus-Eluting Stents," *Heart*, 2009, 95:241-246.

Maier et al., "High concentrations of magnesium modulate vascular endothelial cell behaviour in vitro," *Biochim Biophys. Acta*, 2004, 1689:6-12.

Mamedov et al., "Molecular Design of Strong Single-Wall Carbon Nanotube/Polyelectrolyte Multilayer Composites," *Nature Materials*, 2002, 1:190-194.

Maendl, "Zerstaubungsabscheidung von Mg-Legierungen," *Leibniz-Institut fur Oberflachenmodifizierung*, 2001, pp. 1-17.

Mani et al., "Coronary Stents: A materials perspective," *Biomaterials*, 2007, 28:1689-1710.

Mansfeld, Florian. "Analysis and Interpretation of EIS Data for Metals and Alloys," *Solartron Analytical*, 1999, 1-77.

Marijan et al. "Surface Modification of Stainless Steel-304 Electrode. 2. An Experimental Comparative Study of Electrochemically, Hydrothermally and Chemically Modified Oxide Films." CCACAA, 1999, 72(4) 751-761.

Markman, "Absorbable Coronary stents," *The Lancet*, Jun. 2, 2007, 369:1839-1840.

Massaro et al., "Comparative Investigation of the surface properties of commercial titanium dental implants. Part 1: chemical composition," *Journal of Materials Science: Materials in Medicine*, vol. 13, 2002, pp. 535-548.

Matsuoka et al., "Hyperthermia Using Magnetite Cationic Liposomes for Hamster Osteosarcoma," *Biomagnetic Research and Technology*, Mar. 25, 2004, pp. 1-6.

Medical Device Daily, "Conor Cites Positive 12-month Results for Its CoStar Stent", May 2005 (1 page).

Meng Han, "Laser nitriding of metals: Influences of the ambient pressure and the pulse duration," 2001, Dissertation, Georg-August-Universität Göttingen, 134 pages.

Miao et al., "Porous Calcium Phosphate Ceramics prepared by coating polyurethane foams with Calcium phosphate cements," *Materials Letters*, vol. 58, 2004, pp. 397-402.

Middleton and Tipton. "*Synthetic Biodegradable Polymers as MedicalDevices*," http://www.devicelink.com/mpb/archive/98/03/002.html, Mar. 1998. 9 pages.

Mihailovic et al., "Unusual Magnetic State in Lithium-Doped $MoS_2$ Nanotubes," *Phys. Rev. Lett.*, 2003, 90 146401-1-4.

Mikos and Temenoff, "Formation of highly porous biodegradable scaffolds for tissue engineering," *Electronic Journal of Biotechnology*, 2000, 3(2):114-119.

Mohanty et al. "Evaluation of soft tissue response to a poly[urethane urea]," *Biomaterials*, 1992, 13(10):651-656.

Mohanty et al., "Effect of *Curcuma longa* and *Ocimum sanctum* on myocardial apoptosis in experimentally induced myocardial ischemic-reperfusion injury," *BMC Complementary and Alternative Medicine*, 2006, 6:3-14.

Molnar and Garai, "Plant-derived anti-inflammatory compounds affect MIF tautomerase activity," *International Immunopharmacology*, 2005, 5:849-856.

Moskaug et al., "Polyphenols and glutathione synthesis regulation," *Am. J. Clin. Nutr.*, 2005, 81 (suppl):277S-283S.

Mueller et al., "Control of smooth muscle cell proliferation by ferrous iron," *Biomaterials*, vol. 27, 2006, pp. 2193-2200.

Mueller et al., "Magnesium and its Alloys as Degradable Biomaterials, Corrosion Studies Using Potentiodynamic and EIS Electrochemical Tenchiques," *Materials Research*, 2007, 10(1): 5-10.

Mueller et al., "Preparation of SBF with different $HCO_3$ content and its influence on the composition of biomimetic apatites," *Acta Biomaterialia*, 2006, 2:181-189.

Munoz et al., "Interactive Effects of Albumin and Phosphate Ions on the Corrosion of CoCrMo Implant Alloy," *Journal of the Electrochemical Society*, 2007, 154(10):562-570.

Nachtrab et al., "Quantitative Material Analysis by Dual-Energy Computed Tomography for Industrial NDT Applications," *Fraunhofer EZRT*, date unknown, 1 page.

Naderi et al., "Effect of some volatile oils on the affinity of intact and oxidized low-density lipoproteins for adrenal cell surface receptors," *Mol. Cell. Biochem.*, 2004, 267:59-66.

Nair and Laurencin, "Biodegradable polymers as biomaterials," *Prog. Polym. Sci.*, 2007, 32: 762-798.

Nguyen et al., "Mechanism for protection of iron corrosion by an intrinsically electronic conducting polymer," *Journal of Electroanalytical Chemistry*, 2004, 572: 225-234.

Ni et al., "Cellular localization of antiviral polyoxometalates in J774 macrophages," *Antiviral Research*, 1995, 32: 141-148.

Niemeyer et al., "Magnesium alloys as biodegradable metallic implant materials for cardiovascularic and orthopaedic surgery," *Euromat 2001, 7th European Conference on Advanced Materials and Processes*, Jun. 10-14, 2001 (Abstract).

Niinisto, "Atomic Layer deposition: A key technology for the controlled growth of oxide thin films for advanced applications," *Proc. Estonian Acad. Sci. Phys. Math.*, 2003, 52(3):266-276.

Nilsson et al., "Development of a dosage method for electrochemical treatment of tumours: a simplified mathematical model," *Bioelectrochemistry and Bioenergetics*, 1998, 47:11-18.

Ogata et al., "A novel anti-tumor agent, polyoxomolybdate induces apoptotic cell death in AsPC-1 human pancreatic cancer cells," *Biomedicine & Pharmacotherapy*, 2005, 59: 240-244.

Onuma et al., "Everolimus-eluting bioabsorbable stent," *Euro PCR09*, May 22, 2009, pp. 1-28.

Ormiston et al., "Bioabsorbable Coronary Stents," *Circulation Cardiovasc Intervent*, vol. 2, 2009, pp. 255-260.

Ou et al., "Protective effects of eugenol against oxidized LDL-induced cytotoxicity and adhesion molecule expression in endothelial cells," *Food Chem. Toxicol.*, 2006, 44:1485-1495.

Ouerd et al., "Reactivity of Titanium in Physiolgoical Medium- I. Electrochemical Characterization of the Metal/Protein Interface," *Journal of the Electrochemical Society*, vol. 154, No. 10, 2007, pp. 593-601.

Oyane et al., "Preparation and assessment of revised simulated body fluids," *Wiley Periodicals, Inc.*, 2003, pp. 188-195.

Paliwoda-Porebska et al., "On the development of polypyrrole coatings with self-healing properties for iron corrosion protection," *Corrosion Science*, 2005, 47: 3216-3233.

Park et al., "Microstructural change and precipitation hardening in melt-spun Mg-X-Ca alloys," *Science and Technology of Advanced Materials*, 2001, 2:73-78.

Peeters et al., "Preliminary Results after Application of Absorbable Metal Stents in Patients with Critical Limb Ischemia," *J. Endovasc Ther*, 2005, 12:1-5.

Peeters, et al., "Preliminary Data on Absorbable Metal Stents," *MEET 2006*, Jun. 2006, pp. 1-30.

Peuster et al. "Long-term biocompatibility of a corrodible peripheral iron stent in the porcine of descending aorta," *Biomaterials*, 2006, 4955-4962.

Peuster et al., "A novel approach to temporary stenting: degradable cardiovascular stents produced from corrodible metal-results 6-18 months after implantation into New Zealand white rabbits," *Heart*, 2001, 86(5):563-569.

Peuster et al., "Are resorbable implants about to become a reality," *Cardiol Young*, 2006, 16:107-116.

Pinto Slattow et al., "Optical coherence tomography and intravascular ultrasound imaging of bioabsorbable magnesium stent degradation in porcine coronary arteries," *Cardiovascular Revascularization Medicine 9*, (2008) pp. 248-254.

Prasse et al., "Electric Anisotropy of Carbon Nanofibre/Epoxy Resin Composites Due to Electric Field Induced Alignment," *Composites Science and Technology*, 2003, 63:1835-1841.

Purushothaman et al. "Reducing Mass-Transport Limitations by Application of Special Pulsed Current Modes". *Journal of the Electrochemical Society*. 152 (4), 2005, J33-J39.

Qasem et al., "Kinetics of paclitaxel 2'-N-methylpyridinium mesylate decomposition," *AAPS PharmSciTech*, 2003, 4(2), Article 21, 8 pages.

Quinard et al., "Development of metal/polymer mixtures for micro powder injection moulding," *10th ESAFORM Conference on Material Forming*, 2007, pp. 933-939.

Qureshi et al., "The emerging role of iron, zinc, copper, magnesium and selenium and oxidative stress in health and diseases," *Biogenic Amines*, vol. 19, No. 2, 2005, pp. 147-169.

Raman et al., "Laser assisted modification of surface microstructure for localised corrosion resistance of magnesium alloys," *Surface Engineering*, 2007, 23(2): 107-111.

Ratnam et al., "Role of antioxidants in prophylaxis and therapy: A pharmaceutical perspective," *J. Controlled Release*, 2006, 113:189-207.

Reece et al., "Metal transport studies on inherently conducting polymer membrances containing cyclodextrin dopants," *Journal of Membrane Science*, 2005, 249: 9-20.

Remskar et al., "Self-Assembly of Subnanometer-Diameter Single-Wall $MoS_2$ Nanotubes," *Science*, 2001, 292:479-481.

Rettig et al., "Composition of corrosion layers on a magnesium rare-earth alloy in simulated body fluids," *Journal of Biomedical Materials Research Part A*, Oct. 18, 2006, pp. 359-369.

Rettig et al., "Corrosion resistance studies on grain-boundary etched drug-eluting stents," *J. Mater. Sci: Mater Med.*, 2007, vol. 18, pp. 1377-1387.

Rettig et al., "Time-dependent electrochemical characterization of the corrosion of a magnesium rare-earth alloy in simulated body fluids," *Journal of Biomedical Materials Research Part A*, 2007, 167-175.

Rezwan et al., "Biodegradable and bio active porous polymer/inorganic composite scaffolds for bone tissue engineering," *Biomaterials*, 2006, 27:3413-3431.

Rhule et al., "Polyoxometalates in Medicine," *Chem. Rev.*, 1998, 98:327-357.

Rinkevich et al., "Regeneration of Amputated Avian Bone by a Coral Skeletal Implant," *Biol. Bull.*, vol. 197, Aug. 1999, pp. 11-13.

Rivers et al., "Synthesis of a novel, biodegradable electrically conducting polymer for biomedical applications," *Advanced Functional Materials*, 2002, 12: 33-37.

Russell-Stevens et al., "The effect of thermal cycling on the properties of a carbon fibre reinforced magnesium composite," *Materials Science and Engineering A*, 2005, 397: 249-256.

Rutledge et al., "Electrostatic Spinning and Properties of Ultrafine Fibers," *National Textile Center Annual Report*, Nov. 2001, M01-D22, pp. 1-10.

Ryan et al., "Fabrication methods of porous metals for use in orthopaedic applications," *Biomaterials*, 2006, 27:2651-2670.

Sastry et al., "DNA-Mediated Electrostatic Assembly of Gold Nanoparticles into Linear Arrays by a Simple Drop-Coating Procedure," *Appl. Phys. Left.*, 2001, 78:2943-2945.

Satoh et al., "Effect of Antioxidants on Radical Intensity and Cytotoxic Activity of Eugenol," *Anticancer Res.*, 1998, 18:1549-1552.

Sawitowski et al., "Nanoporous Alumina Coatings for Medical Implants and Stents—Radiotherapy, Drug Delivery, Biological Compatibility," *Materials Research Society Symposium Proceedings*, 1999, 581:523-528.

Sawitowski, "New Drug Delivery Systems—Examples of Applied Nanotechnology," *VDE World Microtechnologies Congress*, Sep. 25-27, 2000, Expo 2000, Hannover, Germany, Proveeds vol. 1, p. 343-346.

Sawyer et al., "Electrochemical Criteria in the Choice of Materials used in Vascular Prostheses," *Biophysical Mechanisms in Vascular Homeostasis and Intravascular Thrombosis*, 1965, pp. 337-348.

Schauer et al., "Protection of iron against corrosion with polyaniline primers," *Progress in Organic Coatings*, 1998, 33: 20-27.

Schetky, "Shape Memory Alloys," *Encyclopedia of Chemical Technology* (3rd ed.), 1982, John Wiley & Sons, 20:726.

Schinhammer et al., "Design strategy for biodegradable Fe-based alloys for medical applications," *Acta Biomaterialia*, 2009, pp. 1-9.

Schmidt et al., "Physiochemical changes in London clay adjacent to cast iron pipes," *IAEG 2006, The Geological Society of London*, Paper 313, 12 pages.

Schneider et al., "From functional core/shell nanoparticles prepared via layer-by-layer deposition to empty nanospheres," *Nano Letters*, 2004, 4: 1833-1839.

Schranz et al., "Bioabsorbable Metal Stents for Percutaneous Treatment of Critical Recoarctation of the Aorta in a Newborn," *Catheterization and Cardiovascular Interventions*, vol. 67, 2006, pp. 671-673.

Secheresse et al., "$(Mo_2O_2X_2)^{2+}$ (X=O,S), a magic building block for the design of wheel shaped metalates," *C.R. Chimie*, 2005, 8: 1927-1938.

Serruys et al., "A bioabsorbable everolimus-eluting coronary stent system (ABSORB): 2-year outcomes and results from multiple imaging methods," *The Lancet*, 2009, 373: 897-910.

Serruys, "Fourth Annual American College of Cardiology International Lecture," *Journal of the American College of Cardiology*, 2006, vol. 47, No. 9, pp. 1754-1768.

Serruys, "Glimpse into the future: bioabsorbable stents-aiming to restore vascular integrity—Introduction & Objectives," *Euro PCR09*, May 18, 2009, pp. 1-4.

Shaw, "Corrosion Resistance of Magnesium Alloys," *ASM Handbook vol. 13A: Corrosion: Fundamentals, Testing, and Protection*. 2003, 5 pages.

Shenoy et al., "Role of Chain Entanglements on Fiber Formation During Electrospinning of Polymer Solutions: Good Solvent, Non-Specific Polymer-polymer Interaction Limit," *Polymer*, 2005, 46:3372-3384.

Shevchenk et al., "Porous Surface of NiTi Alloy Produced by Plasma Ion Implantation," *Institute of Ion Beam Physics and Materials Research*, 2005, Strasbourg, 1 page.

Shevchenko, "Structure, composition and mechanical properties of porous layers produced by argon PIII," *Forschungszentrum Dresden*, Oct. 2007, 8 pages.

Shi et al., "A novel electrically conductive and biodegradable composite made of polypyrrole nanoparticles and polylactide," *Biomaterials*, 2004, 25:2477-2488.

Shieh et al. "Aqueous dispersions of magnetite nanoparticles with NH3 surfaces for magnetic manipulations of biomolecules and MRI contrast agents" *Biomaterials*, 2005 26: 7183-7191.

Shin, "Experimental Characterization of Electrospinning: the Electrically Forced Jet and Instabilities," *Polymer*, 2001, 42:9955-9967.

Sieber, et al., "Investigations on the passivity of iron in borate and phosphate buffers, pH 8.4," *Corrosion Science*, vol. 48, 2006, pp. 3472-3488.

Singh et al., "Electrocatalytic Activity of Electrodeposited Composite Films of Polypyrrole and $CoFe_2O_4$ Nanoparticles Towards Oxygen Reduction Reaction," *Electrochimica Acta*, 2004, 49:4605-4612.

Singh Raman et al., "Laser assisted modification of surface microstructure for localised corrosion resistance of magnesium alloys," *Surface Engineering*, 2007, 23(2):107-111.

Smith et al. "Patterning self-assembled monolayers" *Progress in Surface Science*. 2004. 75:1-68.

Song et al., "Galvanic corrosion of magnesium alloy AZ91D in contact with an aluminium alloy, steel and zinc," *Corrosion Science*, 2004, 46:955-977.

Soto et al., "Amporphous magnesium nitride films produced by reactive pulsed lasar deposition," Journal of Non-Crystalline Solids, 2004, 342: 65-69.

Stoclet et al., "Vascular protection by dietary polyphenols," *Eur. J. Pharmacol.*, 2004, 500:299-313.

Straumal et al., "Vacuum arc deposition of protective layers on glass and polymer," *Thin Solid Films*, 2001, 383:224-226.

Su et al., "Photoacoustic imaging of coronary artery stents," *Optics Express*, vol. 17, No. 22, Oct. 26, 2009, pp. 1-8.

Suhaj, "Spice antioxidants isolation and their antiradical activity: a review," *J. Food Composition and Analysis*, 2006, 19:531-537.

Sukhorukov et al., "Comparative Analysis of Hollow and Filled Polyelectrolyte Microcapsules Templated on Melamine Formaldehyde and Carbonate Cores," *Macromol. Chem. Phys.*, 2004, 205:530-535.

Sun et al., "Fabrication of a multilayer film electrode containing porphyrin and its application as a potentiometric sensor of iodide ion," *Talanta*, 1998, 46: 15-21.

Suslick et al., "The photochemistry of chromium, manganese, and iron porphytin complexes," *J. Chem.*, 1992, 16:633-642.

Tada et al., "Distribution of pH during galvanic corrosion of a Zn/steel couple," *Electrochimica Acta*, 2004, 49:1019-1026.

Tan et al., "Systematic Parameter Study for Ultra-Fine Fiber Fabrication Via Electrospinning Process," *Polymer*, 2005, 46:6128-6134.

Tian et al., "Corrosion resistance improvement of magnesium alloy using nitrogen plasma ion implantation," *Surface & Coatings Technology*, 2005, 198:454-458.

Truong et al., "Corrosion protection of magnesium by electroactive polypyrrole/paint coatings," *Synthetic Metals*, 2000, 110: 7-15.

Uhlmann et al., "Schnelle 3D-Analyse von Gefugemerkmalen" *Druckguss*, Apr. 2009, pp. 1-5.

Van Alst, "Potential conflicts of interest," *Euro PCR09*, 2009, pp. 1-22.

Vermette et al., "Immobilized Liposome Layers for Drug Delivery Applications," *J. Controlled Release*, 2002, 80:179-195.

Virtanen et al., "Electrochemical Behavior of Fe in Phosphate Solutions Studied by In Situ X-Ray Absorption Near Edge Structure," *Journal of the Electrochemical Society*, vol. 146, No. 11, 1999, pp. 4087-4094.

Virtanen et al., "Special modes of corrosion under physiological and simulated physiological conditions," *Acta Biomaterialia*, vol. 4, 2008, pp. 468-476.

Virtanen, "Corrosion of Biomedical Implant Materials," *Corrosion of Biomedical Implant Materials*, vol. 26, Nos. 2-3, 2008, pp. 147-171.

Volkova, "Effect of Deformation and Heat Treatment on the Structure and Properties of Magnesium Alloys of the Mg-Zn-Zr System," *Metal Science and Heat Treatment*, vol. 48, Nos. 11-12, 2006, pp. 508-512.

Volynova et al., "Mechanical Properties and the Fine Structure of Powdered Iron-Manganese Alloys," *Plenum Publishing Corp.*, 1987, pp. 999-1006.

von Euler et al., "Cell proliferation and apoptosis in rat mammary cancer after electrochemical treatment (EChT)," *Bioelectrochemistry*, 2004, 62:57-65.

Vrbanic et al., "Air-Stable Monodispersed $Mo_6S_3I_6$ Nanowires," *Nanotechnology*, 2004, 15:635-638.

Waksman et al., "Early-and Long-Term Intravascular Ultrasound and Angiographic Findings After Bioabsorbable Magnesium Stent Implantation in Human Coronary Arteries," *JACC: Cardiovascular Interventions*, vol. 2, No. 4, 2009, pp. 1-9.

Waksman et al., "Safety and Efficacy of Bioabsorbable Magnesium Alloy Stents in Procine Coronary Arteries," *Catherterization and Cardiovascular Intervnetions*, 2006, vol. 68, pp. 607-617.

Waksman et al., "Short-term Effects of Biocorrodible Iron Stents in Porcine Coronary Arteries," *Journal of Interventional Cardiology*, vol. 21, No. 1, 2008, pp. 15-20.

Waksman, "Update on Bioabsorbable Stents: From Bench to Clinical," *Journal of Interventional Cardiology*, vol. 19, No. 5, 2006, pp. 414-421.

Waksman, Ron, "Current state of the metallic bioabsorbable stent," Glimpse to the Future, *Euro PCR09*, 2009, pp. 1-24.

Waksman, Ron, "Why Bioabsorbale Stent Technology," Glimpse to the Future, *Euro PCR09*, 2009, pp. 1-16.

Wallerath et al., "A blend of polyphenolic compounds explains the stimulatory effect of red wine on human endothelial NO synthase," *Nitric Oxide*, 2005, 12:97-104.

Wan et al., "Preparation and characterization of porous conducting poly(DL-lactide) composite membrances," *Journal of Membrane Science*, 2005, 246: 193-201.

Wan et al., "Influence of Plasma Immersion Ion Implantation on Corrosion Properties of Magnesium," *Southwest Jiaotong University*, 2005, Chengu, 11 pages.

Wang et al., "Nonlinear optical properties of thin iron films grown on MgO (100) by uplsed laser deposition," *Thin Solid Films*, 2005, 471:86-90.

Wang et al., "Polyaniline microrods synthesized by a polyoxometalates/poly(vinyl alcohol) microfibers template," *Materials Letters*, 2005, 59: 3982-3985.

Weiss et al., "Pyrrole derivatives for electrochemical coating of metallic medical devices," J. Polymer Science, Part A: Polymer Chemistry, 2004, 42: 1658-1667.

Wang et al., "Characterisation of Severely Deformed Austenitic Stainless Steel Wire," *Materials Science and Technology*, 21(11):1323-1328

Wang, "Recent development of non-platinum catalysts for oxygen reduction reaction," *J. Power Sources*, 2005, 152:1-15

Weber et al., "Hardness and corrosion resistance of single-phase nitride and carbide on ion," *Materials Science and Engineering*, 1995, 99:205-210.

Weh et al., "Evolution of afractal-like surface structures in layers of polyacrylonitrile solutions by interfacial dynamic processes," *J. Colloid and Interface Science*, 2004, 271: 407-415.

White and Slade, "Polymer electrodes doped with heterpolymetallates and their use within solid-state supercapacitors," *Synthetic Metals*, 2003, 139: 123-131.

Widmer et al., "Manufacture of porous biodegradable polymer conduits by an extrusion process for guided tissue regeneration," *Biomaterials*, 1998, 19:1945-1955.

Wieneke et al., "Stent Coating: A New Approach in Interventional Cardiology," *Herz*, 2002, 27(6):518-526.

Wilcox, "Biodegradable Technology: Medtronic Biodegradable Stent Program," *Euro PCR09*, 2009, pp. 1-25.

Williamson and Manach, "Bioavailability and bioefficacy of polyphenols in humans. II. Review of 93 intervention studies," *Am. J. Clin. Nutr.*, 2005, 81(suppl):243S-255S.

Windecker et al., "Biolimus-eluting stent with biodegradable polymer versus sirolimus-eluting stent with durable polymer for coronary revascularisations (LEADRERS): a randomized non-inferiority trial," *The Lancet*, Sep. 1, 2008, pp. 1-11.

Witte et al., "Biodegradable magnesium-hydroxyapatite metal matrix composites," *Biomaterials*, vol. 28, 2007, pp. 2163-2174.

Witte et al., "In vitro and in vivo corrosion measurements of magnesium alloys," *Biomaterials*, 2006, 27:1013-1018.

Witte et al., "In Vivo Corrosion of Four Magnesium Alloys and the Associated Bone Response," *Biomaterials*, vol. 26, 2005, pp. 3557-3563.

Witte, "The history of biodegradable magnesium implants: A review," *Acta Biomaterialia*, 2010, 6: 1680-1692.

Witte, "Magnesium Corrosion: a New Challaenge for temporary Biomaterials," *Laboratory for Biomechanic and Biomaterials*, 2009, pp. 1-20.

Wuisman and Smit, "Bioresorbable polymers: heading for a new generation of spinal cages," *Eur. Spine J.*, 2006, 15: 133-148.

Xu et al., "In Vivo corrosion behaviouc of Mg-MnZn alloy for bone implant application," *Journal of Biomedical Materials Research Part A*, Jun. 4, 2007, pp. 703-711.

Yamaguchi et al., "Mg2Si Coating Technology on Magnesium Alloys to Improve Corrosion and Wear Resistance", *JOM*, 2004, p. 343.

Ye et al., "In situ synthesis of AlN particles in Mg-Al alloy by $Mg_3$-$N_2$ addition," *Materials Letters*, 2004, 58: 2361-2361.

Yfantis et al., "Novel corrosion-resistant films for Mg alloys," *Surface and Coatings Technology*, 2002, 151-152: 400-404.

Yi et al., "Characterization of a bioactive nanotextured surface created by controlled chemical oxidation of titanium," *Surface Science*, 2006, 600:4613-4621.

You et al., "The Effect of Calcium Additions on the Oxidation Behavior in Magnesium Alloys," *Scripta mater.*, 2000, 42:1089-1094.

Yu and Uan, "Sacrificial Mg film anode for cathodic protection of die cast Mg-9-wt.%-1 wt.%Zn alloy in NaCl aqueous solution," *Scripta Mat.*, 2006, 54:1253-1257.

Yue et al., "Improvement in the Corrosion Resistance of Magnesium ZK60/SiC Composite by Excimer Laser Surface Treatment," *Scripta Materialia*, 1998, 38(2):191-198.

Yuen et al., "Findings from an Accelerated in Vivo Corrosion Model of Magnesium," *Department of Orthopaedics and Traumatology*, date unknown, pp. 1-2.

Yun et al., "Revolutionizing Biodegradable Materials," *Materials Today*, Oct. 2009, vol. 12, No. 10, pp. 1-11.

Zarras et al., "Progress in using conductive polymers as corrosion-inhibiting coatings," *Radiation Physics and Chemistry*, 2003, 68: 387-394.

Zberg et al., "MgZnCa glasses without clinically observable hydrogen evolution for biodegradable implants," *Nature materials*, Sep. 27, 2009, vol. 8, pp. 887-891.

Zeta Potential—An Introduction in 30 Minutes, Technical Note; http://www.nbtc.cornell.edu/facilities/downioads/
Zeta%20potential%20-
%)20An%20introduction%20in%2030%20minutes.pdf, Retrieved from the Internet on May 9, 2005 (6 pages).

Zhang et al., "Improving multilayer films endurance by photoinduced interaction between Dawson-type polyoxometalate and diazo resin," *Materials Chemistry and Physics*, 2005, 90:47-52.

Zhang et al., "Natural Polyelectrolyte Films Based on Layer-by-Layer Deposition of Collagen and Hyaluronic Acid," *Biomaterials*, 2005, 26:3353-3361.

Zhang et al., "Ways for fabricating stable layer-by layer self-assemblies: combined ionic self-assembly and post chemical reaction," *Colloids and Surfaces A: physiochemical and Engineering Aspects*, 2002, pp. 198-200, 439-442.

Zheng, "Symposium on Biodegradable/Biocorroded metallic materials," Nov. 24, 2009, pp. 1-74.

Zhou et al., "Drug-loaded, Magnetic, hollow silica nanocomposites for nanomedicine," *Nanomedicine: Nanotechnology, Biology and Medicine*, 2005, 1:233-237.

Zhu et al., "Biocompatibility of Fe-O films synthesized by plasma immersion ion implantation and deposition," *Surface and Coatings Technology*, vol. 203, 2009, pp. 1523-1529.

Zhu et al., "Biocompatibility of pure iron: In Vitro assessment of degradation kinetics and cytotoxicity on endothelial cells," *Materials Science and Engineering*, vol. 29, 2009, pp. 1589-1582.

Zou et al., "Preparation of a phosophopolyoxomolybdate $P_2Mo_{18}O^{6-}{}_{62}$ doped polypyrrole modified electrode and its catalytic properties," *Journal of Electroanalytical Chemistry*, 2004, 566: 63-71.

Zucchi et al., "Electrochemical behaviour of a magnesium alloy containing rare earth elements," *Journal of Applied Electrochemistry*, 2006, vol. 36, pp. 195-204.

Zucchi et al., "Influence of a silane treatment on the corrosion resistance of a WE43 magnesium alloy," *Surface Coatings Technol.*, 2006, 200:4136-4143.

International Search Report and Written Opinion from PCT/US09/043591, mailed Jun. 30, 2010, 10 pages.

International Search Report from PCT/US07/005671, mailed Jun. 2, 2008, 10 pages.

Ma et al , "Inhibition effect of self-assembled films formed by gold nonoparticles on iron surface," *Applied Surface Science*, 2006, 252: 4327-4334.

Li et al., "The corrosion inhibition of the self assembled Au, and Ag nonoparticles films on the surface of copper," Colloids and Surfaces A: Physiochem. Eng. Aspects, 2006, 273: 16-23.

International Preliminary Report on Patentability from PCT/US08/75976 dated Mar. 25, 2010, mailed Nov. 25, 2008, 8 pages.

Wikipedia, the Free Encyclopedia, "Galvanic Corrosion." <http://en.wikipedia.org/wiki/Galvanic_corrosion> on Mar. 11, 2011, 7 pages.

Authorized Officer Mary Celine, International Search Report from PCT/US2010/060412 mailed Feb. 21, 2011, 10 pages.

Dumas et al., "Characterization of magnesium fluoride thin films produced by argon ion beam-assisted deposition," *Thin Solid Films*, 2001, pp. 61-68.

Authorized Officer Razik Menidjel, International Preliminary Report on Patentability from PCT/US09/059424, mailed May 5, 2011, 8 pages.

\* cited by examiner

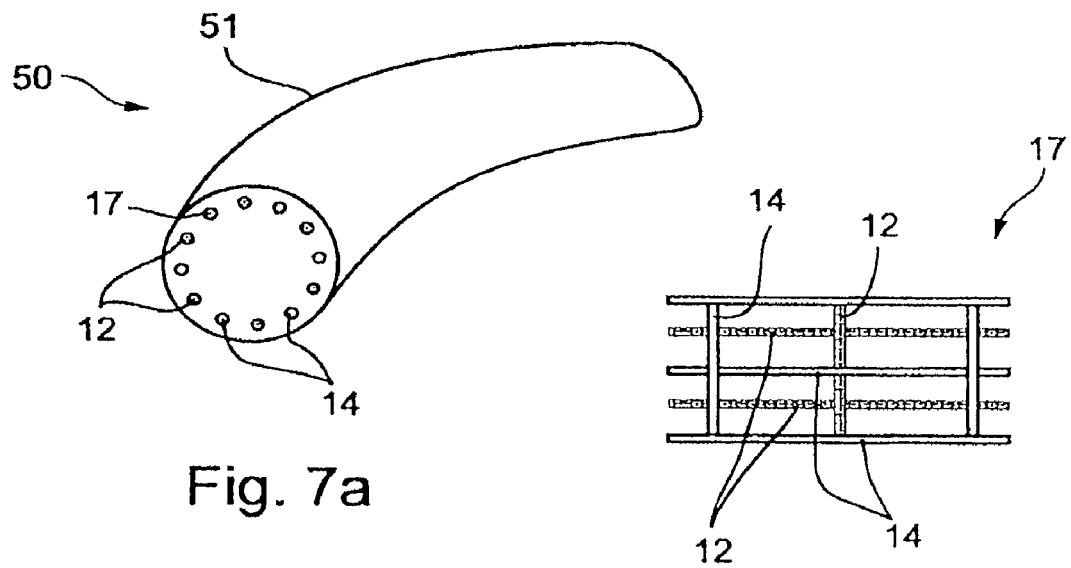
Fig. 7a
Fig. 7b
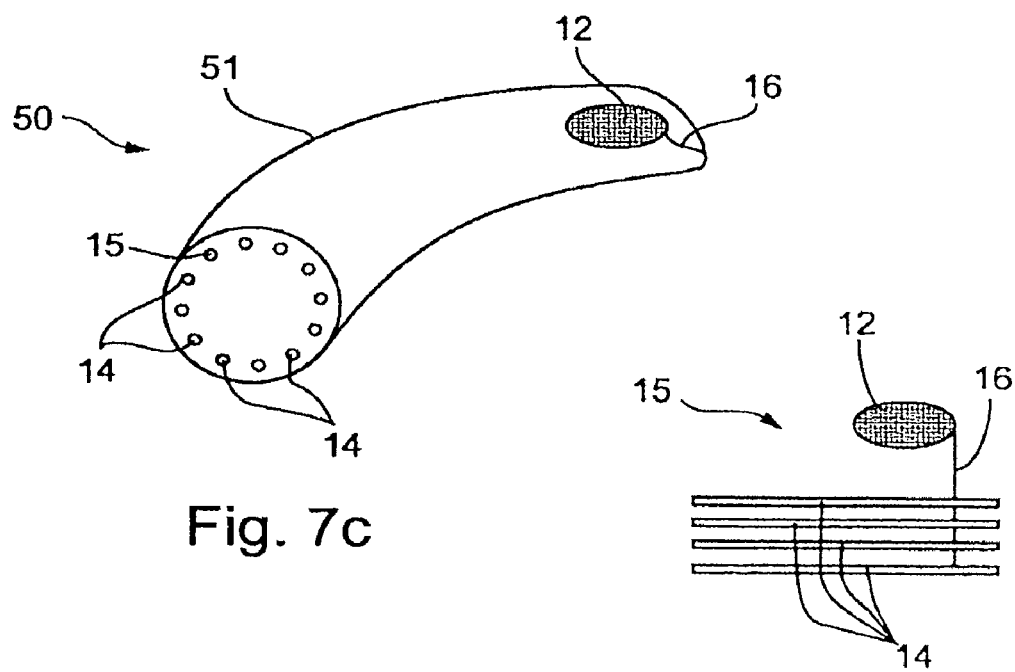
Fig. 7c
Fig. 7d

METHOD AND DEVICE FOR ELECTROCHEMICAL FORMATION OF THERAPEUTIC SPECIES IN VIVO

CROSS-REFERENCE TO RELATED APPLICATIONS

This application is a divisional application of and claims priority to U.S. application Ser. No. 10/477,514, filed on Nov. 19, 2003, now U.S. Pat. No. 7,727,221. The above noted application is hereby incorporated by reference in its entirety.

FIELD OF THE INVENTION

The present invention relates generally to in vivo electrochemical formation of therapeutic species, and in particular, to in vivo electrochemical formation of therapeutic species with no use of external power.

BACKGROUND OF THE INVENTION

Electrochemical reactions are chemical reactions in which electrons are transferred from one atom to another. Electrochemistry is thus a branch of chemistry that deals with the chemical changes produced by electricity and conversely, the production of electricity by chemical changes. A basic overview of electrochemistry may be obtained, for example, from Chemical Sciences, by James A. Plambeck, http://www.compusmart.ab.ca/plambeck/che/p102/p02071.htm, 1995, and from Stoner et al. Bioelectrochemistry and Bioengineering, 9, (1982) 229-243.

Three types of electrochemical reactions may be distinguished, as follows:

i. An oxidation reaction, in which electrons are lost by atoms of the species involved in the reaction, so that the atoms become more positive, i.e., their oxidation state increases. In an oxidation reaction, electrons appear as products.

ii. A reduction reaction, in which electrons are gained by the species involved in the reaction, so that they become less positive, i.e., their oxidation state decreases. In a reduction reaction, electrons appear as reactants.

iii. A redox reaction, which involves both a reduction and an oxidation, and is called redox as an abbreviation to these. The stoichiometry of a redox reaction is such that all the electrons lost in the oxidation are gained in the reduction, so in a redox reaction, electrons do not appear explicitly.

One may thus define a reducing agent, as a species that reduces another species, and is itself oxidized in the process. Similarly, one may define an oxidizing agent, as a species that oxidizes another species, and is itself reduced in the process.

Two types of electrical conductors are operative in electrochemical reactions. An electronic conductor, such as a metal, and an ionic conductor, such as a solution containing ions, often called an electrolyte solution, or an electrolyte.

An electronic conductor, such as a metal, in contact with an electrolyte, is termed, an electrode. An electrode on whose surface an oxidation reaction takes place is defined as an anode. The anode acts as an electron sink to the electrolyte. Similarly, an electrode on whose surface a reduction reaction takes place is a cathode. The cathode acts as an electron source to the electrolyte.

In corrosion reactions, an electrochemical reaction may be sustained by a single metal, immersed in an electrolyte. The corroding metal acts both as the anode and the cathode. For example, when a strip of zinc is immersed in an acidic solution, an oxidation reaction takes place on its surface, as follows:

$$Zn \rightarrow Zn^{2+} + 2e^- \quad \text{[I]}$$

This process cannot continue for any significant length of time, without a suitable cathodic process, in which the electrons are consumed. Thus the strip of metal zinc also acts as a cathode, providing a nucleation site and a source for the electrons, for example, in the cathodic reaction:

$$2H^+ + 2e^- \rightarrow H_2 \quad \text{[II]}$$

Corrosion reactions may also take place in a neutral environment, wherein the cathodic reaction may cause the solution to become more alkaline:

$$O_2 + 2H_2O + 4e^- \rightarrow 4(OH)^- \quad \text{[III]}$$

Although the zinc strip may act both as anode and as cathode, the addition of a second conducting strip, connected by wire to the zinc strip, will form an electrode pair. If the second strip is less active than the zinc, then the zinc strip will operate as the anode, and the second strip will operate as the cathode.

Certain metals such as platinum, though inert to electrochemical reactions, have a catalytic effect on the corrosion reaction. For example, when using platinum as a cathode, for reaction [II], the rate of the reaction may increase by a factor of $10^4$-$10^5$, compared to its rate on zinc Two or more electrodes, immersed in an electrolyte and connected by an electronic conductor, form an electrochemical cell.

In a galvanic electrochemical cell, current flows, power is produced, and the cell reaction proceeds spontaneously.

In an electrolytic electrochemical cell, current flows, power is consumed, and the cell reaction, which is driven, is the reverse of the spontaneous reaction of the glavanic cell.

In a reversible electrochemical cell, an infinitesimal change in cell potential can cause the reaction to proceed in either direction.

Chemists have selected the electrode reaction of hydrogen, under standard conditions of pressure and concentration, as a basis against which others electrode reactions are compared, and have termed it, standard hydrogen electrode (S.H.E.). The physically measured potential difference across a reversible cell made up of any electrode and a standard hydrogen electrode is called the reversible potential of the electrode, E. If the electrode (other than hydrogen) is also being operated under standard conditions of pressure and concentrations, the potential difference across the cell is the standard electrode potential, $E^0$ of the electrode other than hydrogen.

The Nernst Equation for an electrode links the actual (measurable) reversible potential of an electrode E, to the standard reversible potential, $E^0$. It may be described as:

$$E = E^0 - (0.05915/n) \log(\text{activity of the reactants/activity of the products}),$$

where n is the reaction charge (the number of electrons that are transferred).

Another use of the Nernst equation is to provide the activity ratio, which is approximately equal to the concentration ratio between the reactants and products.

Given the reversible potential at an electrode E, and the concentration of the reactants, the concentration of the products may be calculated, and vise versa.

While electrochemistry is extensively applied in many technological fields, its application in vivo is limited to fewer reports and applications.

Electrochemical treatment of tumors is referred to in the medical literature as ECT.

In an ECT procedure, electrodes are implanted at spaced positions in or around the malignant tumor to be treated. Applied across these electrodes is a low DC voltage usually having a magnitude of less than 10 volts, causing a current to flow between the electrodes through the tumor. Due to an electrochemical process, reaction products are formed, which include cytotoxic agents that act to destroy the tumor cells.

In the ECT technique disclosed by Li et al., in Bioelectromagnetic 18:2-7 (1997), in the article "Effects of Direct Current on Dog Liver: Possible Mechanisms For Tumor Electrochemical Treatment" two platinum anode and cathode electrodes were inserted in a dog's liver with a 3 cm separation therebetween. Applied across these electrodes was a DC voltage of 8.5 volts, giving rise to an average current through the liver of 30 mA. This was continued for 69 minutes, with a total charge of 124 coulombs.

The concentration of selected ions near the anode and cathode were measured. The concentration of $Na^+$ and $K^+$ ions were found to be higher around the cathode, whereas the concentration of $Cl^-$ ions was higher around the anode. Water content and pH were determined near the anode and cathode, the pH values being 2.1 near the anode and 12.9 near the cathode. The released gases were identified as chlorine at the anode and hydrogen at the cathode. The series of electrochemical reactions which took place during ECT resulted in the rapid and complete destruction of both normal and tumor cells in the liver.

Another example of ECT appears in the article "Electrochemical Treatment of Lung Cancer" by Xin et al. in Bioelectromagnetics 18:8-13 (1997). In this ECT procedure platinum electrodes were inserted transcutaneously into a tumor, the voltage applied thereto was in the 6-8 volt range, the current was in the 40 to 100 mA range, and the electric charge, 100 coulombs per cm of tumor diameter.

According to this article, the clinical results indicate that ECT provides a simple, safe and effective way of treating lung cancers that are surgically inoperable and are not responsive to chemotherapy or radiotherapy.

Also disclosing ECT techniques are Chou et al., Bioelectromagnetics 18:14-24 (1997); Yen et al., Bioelectromagnetics 20:34-41 (1999); Turler at al., Bioelectromagnetics 21:395-401 (2000); Ren at al., Bioelectromagnetics 22:205-211 (2001); U.S. Pat. No. 5,360,440 to Andersen and U.S. Pat. No. 6,021,347 to Herbst et al.

Electrochemical reactions as a function of pH and electrode potential can be predicted by means of a Pourbaix diagram, as disclosed in the Atlas of Electrochemical Equilibria in Aqueous Solutions—Pergamon Press, 1986—by Pourbaix.

While U.S. Pat. No. 5,458,627 to Baranowski Jr., et al. does not relate to ECT but to the electrochemically controlled stimulation of osteogenesis, it is nevertheless of prior art interest, for it discloses that reaction products produced by an electrochemical reaction includes not only hydrogen and oxygen, but also hydrogen peroxide.

In the text Methods in Cell Biology, Vol. 46—Cell Death—published by Academic Press, it is noted (on page 163), that hydrogen peroxide has been reported to be an inducer of cell death in various cell systems. This type of cell death is attributed to the direct cytotoxicity of $H_2O_2$ and other oxidant species generated from $H_2O_2$.

The above described ECT technologies are limited in several aspects. First, they all pertain to the treatment of solid tumor masses, yet other applications are not envisaged. Second, they all fail to teach implantable electrochemical devices which are controlled and/or powered via telemetry.

U.S. Pat. Nos. 5,797,898 and 6,123,861 to Santini Jr. et al. both describe microchips which comprise a plurality of drug containing capped reservoirs, whereas in one embodiment the release of the drug therefrom is effected by disintegration of the caps via an electrochemical reaction.

While Santini Jr. et al. teach an electrochemical in vivo drug release mechanism effected by telemetry, Santini Jr. et al. fails to teach the in vivo electrochemical production of therapeutic agents.

U.S. Pat. No. 6,185,455, teaches functional neuromuscular stimulation (FNS) or functional electrical stimulation (FES) devices, designed also to locally release drugs that inhibit physiological reactions against the devices.

U.S. Pat. No. 5,938,903 teaches a microelectrode for inserting in vivo, in vitro into a warm-blooded or cold blooded animal brain or body, or extra-corporeally and measuring intracellular and/or extracellular concentration and/or release and/or reuptake of one or more biogenic chemicals while measuring said chemical in vivo or in vitro.

U.S. Pat. No. 5,833,715 teaches a pacing lead having a stylet introduced anti-inflammatory drug delivery element advanceable from the distal tip electrode. The element is formed as a moldable biocompatible composite material. The element has a biocompatible matrix material which may be combined with drugs and therapeutic agents to deliver the drugs and agents by co-dissolution or diffusion to the point of either passive or active fixation. The drug delivery element may be rigid and serve to center an active fixation mechanism, preferably a helix, which penetrates the myocardium.

U.S. Pat. No. 3,868,578 teaches a method and apparatus for electroanalysis.

U.S. Pat. No. 6,201,991 teaches a method and system for preventing or treating atherosclerosis in which a blood vessel susceptible to or containing atherosclerotic plaque is subjected to a low-frequency electrical impulse at an effective rate and amplitude to prevent or impede the establishment or decrease the size of the plaque in the vessel. The system can be implanted into the body of a patient or applied externally to the skin.

U.S. Pat. No. 5,360,440 teaches an apparatus for the in situ generation of an electrical current in a biological environment characterized by including an electrolytic fluid. The apparatus comprises first and second electrodes of differing electrochemical potentials separated by an insulator. The apparatus is adapted to be implanted in the environment. The presence of the electrolytic fluid and formation of a current path by hyperplastic cells bridging the electrodes enables electrolysis to occur and a direct current to pass through the current path to impede hyperplastic cell growth.

U.S. Pat. No. 6,206,914 teaches an implantable system that includes a carrier and eukaryotic cells, which produce and release a therapeutic agent, and a stimulating element for stimulating the release of the therapeutic agent. The system can also include a sensing element for monitoring a physiological condition and triggering the stimulating element to stimulate the delivery device to release the therapeutic agent. Alternatively, the patient in whom the system is implanted can activate the stimulating element to release the therapeutic agent. In one embodiment the carrier is medical electrical electrodes.

U.S. Pat. No. 6,366,808 describes an implantable electrical method and apparatus for the treatment of cancer tumors based on the usage of various levels of electrical fields and current to assist in specific ways to reduce tumor size. The method comprises: (1) implanting at least one electrode into or near a tumor, (2) implanting a source of electrical power, (3) connecting the electrode to the source of electrical power and (4) delivering electrical current into the tumor. Alternatively, the method comprises: (1) implanting at least one electrode into a tumor, (2) implanting a source of electrical power, (3) connecting the electrode to the source of electrical power, (4) monitoring at least one voltage from within tissue, and (5) delivering electrical current into the tumor. In both cases, it is the electrical current that provides the therapeutic action.

U.S. Pat. No. 5,951,458 describes a method for inhibiting restenosis by local application of an oxidizing agent to blood vessel walls. Preferred oxidizing agents include peroxides, most preferably hydrogen peroxide. Oxidizing agents can be delivered utilizing drug delivery balloon catheters. Preferred delivery catheters include an inflatable balloon having a perfusion lumen therethrough to allow for longer application periods. Oxidizing agents can be delivered either alone or in conjunction with radiation or stent delivery. One method includes local delivery of 0.1% hydrogen peroxide to a dilated stenosis wall for a period of 10 minutes at a rate of 0.5 cc per minute.

Each one of these patents, however, fails to teach in vivo electrochemical production of therapeutic agents.

There is thus a great need for and it would be highly advantageous to have methods, systems and devices for in vivo electrochemical production of therapeutic agents.

SUMMARY OF THE INVENTION

Hence, according to one aspect of the present invention, there is provided a method of producing a therapeutic agent in a body, the method comprising implanting an active metal in a tissue, for electrochemically converting at least one substance present in the body fluid into the therapeutic agent.

According to an additional aspect of the present invention, electrochemically converting the at least one substance present in the body fluid into the therapeutic agent comprises direct conversion.

According to an additional aspect of the present invention, electrochemically converting the at least one substance present in the body fluid into the therapeutic agent comprises indirect conversion.

According to an additional aspect of the present invention, the at least one substance is a normal body fluid constituent.

According to an additional aspect of the present invention, the normal body fluid constituent is selected from the group consisting of water, molecular oxygen, nitrite and nitrate ions and L-arginine.

According to an alternative aspect of the present invention, the at least one substance is administered to the body.

According to an additional aspect of the present invention, the at least one substance is administered to the body through a diet.

According to an alternative aspect of the present invention, the at least one substance is administered to the body through a medical administration.

According to an additional aspect of the present invention, the at least one substance is selected from the group consisting of nitrite ion, nitrate ions, and a combination thereof.

According to an additional aspect of the present invention, the therapeutic agent is the vasodilating agent, nitric oxide (NO).

According to an alternative aspect of the present invention, the therapeutic agent is an oxidizing agent.

According to an additional aspect of the present invention, the oxidizing agent is selected from the group consisting of molecular chloride, perchloric acid, superoxide, ozone, molecular oxygen, singlet oxygen, hydroxyl radical, hypochlorite, hydrogen peroxide and a combination thereof.

According to an additional aspect of the present invention, the active metal comprises zinc.

According to an alternative aspect of the present invention, the active metal comprises iron.

According to an additional aspect of the present invention, implanting comprises implanting a stent formed of a biologically inert metal, fully coated with the active metal.

According to an alternative aspect of the present invention, implanting comprises implanting a stent formed of a biologically inert metal, having:

a portion coated with the active metal, operative as an anode; and an uncoated portion, operative as a cathode.

According to an additional aspect of the present invention, the implanting further comprises implanting the portion coated with the active metal, downstream of the uncoated portion, so that the therapeutic agents, produced at the cathode, will migrate downstream with the body fluid, to effect therapy at the anode as well.

According to an alternative aspect of the present invention, the coated and uncoated portions are equally distributed along the length and width of the stent.

According to an additional aspect of the present invention, the uncoated portion is further operative as a catalyst to the conversion.

According to an alternative aspect of the present invention, implanting comprises implanting a stent formed of a biologically inert material, wherein the stent includes a piece of the active metal attached thereto.

According to an additional aspect of the present invention, the stent is further operative as a catalyst to the conversion.

According to an alternative aspect of the present invention, implanting comprises implanting an anchor formed of a biologically inert metal, fully coated with the active metal.

According to an additional aspect of the present invention, implanting comprises implanting an anchor formed of a biologically inert metal, having:

a portion coated with the active metal, operative as an anode; and an uncoated portion, operative as a cathode.

According to an additional aspect of the present invention, the implanting further comprises implanting the portion coated with the active metal, downstream of the uncoated portion, so that the therapeutic agents, produced at the cathode, will migrate downstream with the body fluid, to effect therapy at the anode as well.

According to an alternative aspect of the present invention, the coated and uncoated portions are equally distributed along the length and width of the anchor.

According to an additional aspect of the present invention, the uncoated portion is further operative as a catalyst to the conversion.

According to an alternative aspect of the present invention, implanting comprises implanting an anchor formed of a biologically inert material, wherein the anchor includes a piece of the active metal attached thereto.

According to an additional aspect of the present invention, the anchor is further operative as a catalyst to the conversion.

According to an additional aspect of the present invention, the tissue is a blood vessel.

According to an additional aspect of the present invention, the tissue is a renal artery.

According to an alternative aspect of the present invention, the tissue a brain tissue.

According to an alternative aspect of the present invention, the tissue is a cancerous tissue.

According to an alternative aspect of the present invention, the tissue is a blood vessel feeding a cancerous tissue.

According to an alternative aspect of the present invention, the tissue is a blood vessel feeding a tissue for which therapeutic treatment is desired.

According to another aspect of the present invention, there is provided a method, comprising implanting an active metal in the body, for electrochemically converting at least one substance, present in the body, into the oxidizing agent.

According to another aspect of the present invention, there is provided a method, comprising implanting an active metal in the tissue, for electrochemically converting at least one substance, present in the body fluid, into an oxidizing agent, in an amount sufficient for reducing cell proliferation in the tissue.

According to another aspect of the present invention, there is provided a method, comprising implanting an active metal in a tissue, for electrochemically converting at least one substance present in the body fluid into the vasodilating agent, nitric oxide.

According to another aspect of the present invention, there is provided a medical implant for producing a therapeutic agent in a body, the medical implant comprising an active metal for electrochemically converting in a body fluid stream environment, at least one substance present in the body fluid into the therapeutic agent.

According to another aspect of the present invention, there is provided an implanted vessel, comprising an active metal, for electrochemically converting in a body fluid stream environment, at least one substance present in the body fluid into the therapeutic agent. The present invention successfully addresses the shortcomings of the presently known configurations by providing a device and method for spontaneous electrochemical production of therapeutic species, within a tissue, by implanting in the tissue an active metal, which undergoes corrosion, thus acting as a reducing agent to constituents in the tissue, so as to cause these constituents to form the therapeutic agents.

Unless otherwise defined, all technical and scientific terms used herein have the same meanings as are commonly understood by one of ordinary skill in the art to which this invention belongs. Although methods and materials similar or equivalent to those described herein can be used in the practice or testing of the present invention, suitable methods and materials are described herein.

In case of conflict, the patent specification, including definitions, will prevail. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIGS. 7A-7D are schematic illustrations of implantable vessels, in accordance with another preferred embodiment of the present invention.

DESCRIPTION OF THE PREFERRED EMBODIMENTS

The present invention is of a device and method for spontaneous electrochemical production of therapeutic species, within a tissue. Specifically, the present invention relates to implanting in the tissue an active metal, which undergoes corrosion, thus acting as a reducing agent to constituents in the tissue, so as to cause these constituents to form the therapeutic agents.

The principles and operation of the device according to the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Figure 1:
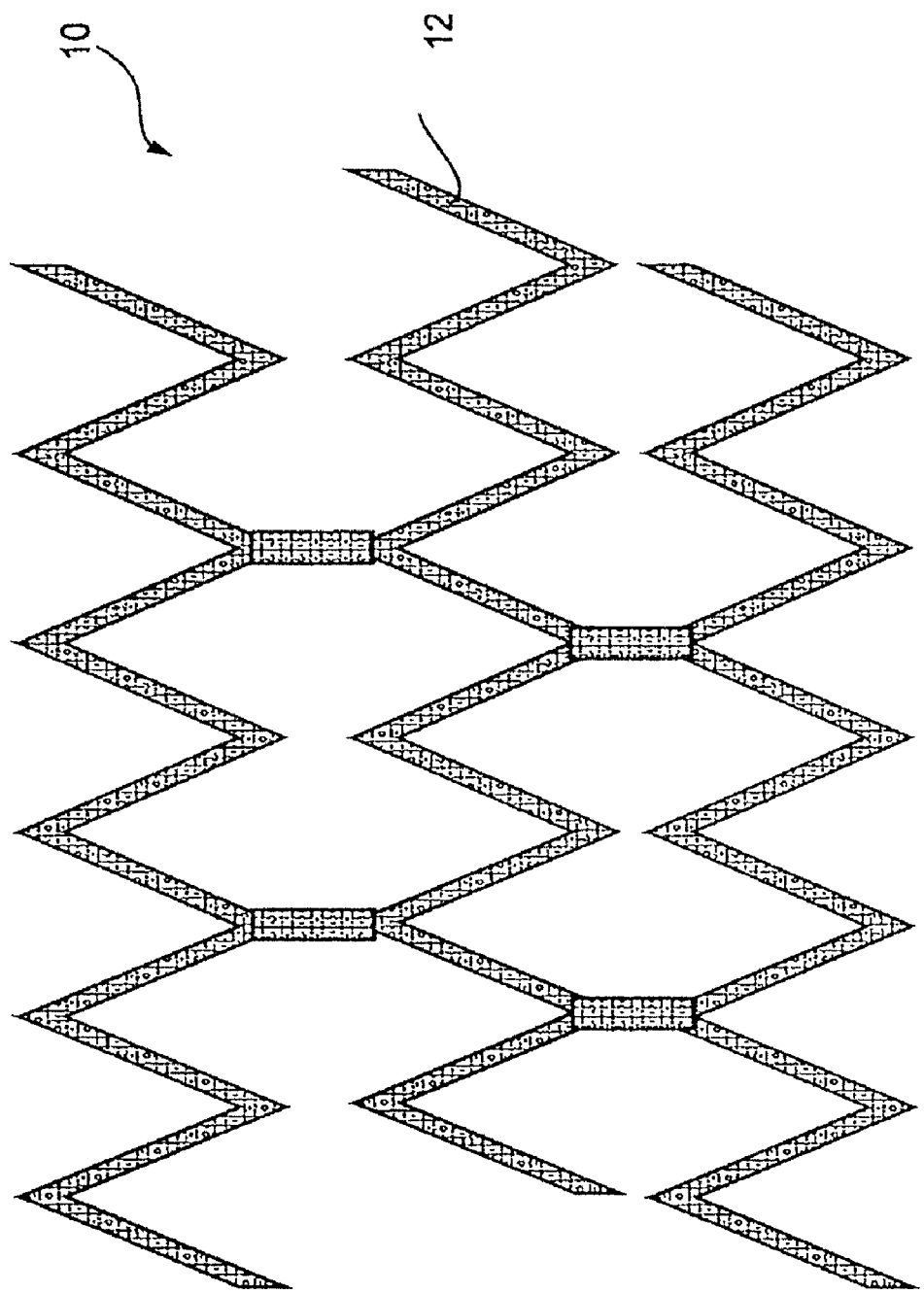
FIG. 1 is a schematic illustration of a stent, coated with an active metal, in accordance with another preferred embodiment of the present invention.

Referring now to the drawings, FIG. 1 is a schematic illustration of an implant 10, formed as a stent 10, fully coated with an active metal 12, in accordance with a first preferred embodiment of the present invention. An active metal in the present context is a metal that will corrode in the body environment, and thus act as a reducing agent. Active metal 12 may be for example, zinc. Alternatively, it may be iron.

Stent 10 is adapted for implantation in a blood vessel, where active metal 12 will corrode and act as a reducing agent for blood constituents, and (or) other body fluid constituents, as will be described hereinbelow, in conjunctions with Examples 1-8. In accordance with the first preferred embodiment of the present invention, stent 10 is homogeneous, and operative as an anode and a cathode, wherein both oxidation and reduction reactions occur on its surface. In the absence of a catalyst, such as platinum, the corrosion reaction is relatively slow. Thus the first preferred embodiment of the present invention is applicable to situations, where a slow reaction rate is preferred.

Preferably, stent 10 is operative as a reducing agent, water and molecular oxygen, leading to the production of hydrogen peroxide and hydroxide ions. These can be used to prevent unwanted cell proliferation in cases of, for example, cancer, stenosis, restenosis, in-stent stenosis, and in-graft stenosis. Their production by stent 10 is particularly useful for treatment of in-stent stenosis.

Additionally or alternatively, stent 10 is operative as a reducing agent to nitrite and nitrate ions, and L-arginine, leading to the production of the vasodilating agent nitric oxide (NO). Nitric oxide may be operative to dilate blood vessels. In particular, stent 10 may be placed in the renal artery, and the production of nitric oxide may enlarge renal blood vessels and blood capillaries. However, it will be appreciated that for significant production of nitric acid, nitrite and nitrate ions may need to be administered to the body, by diet, or intravenously.

As will be described hereinbelow, in conjunction with Examples 1-8, some reduction reactions are a single-step reduction process, so the electrochemical conversion of a substance into a therapeutic agent may be considered a direct conversion. Other reduction reactions include two or more steps, so the electrochemical conversion of a substance into a therapeutic agent may be considered indirect conversion.

It will be appreciated that since the active metal undergoes depletion, the therapeutic nature of the present invention is temporary.

Figure 2:
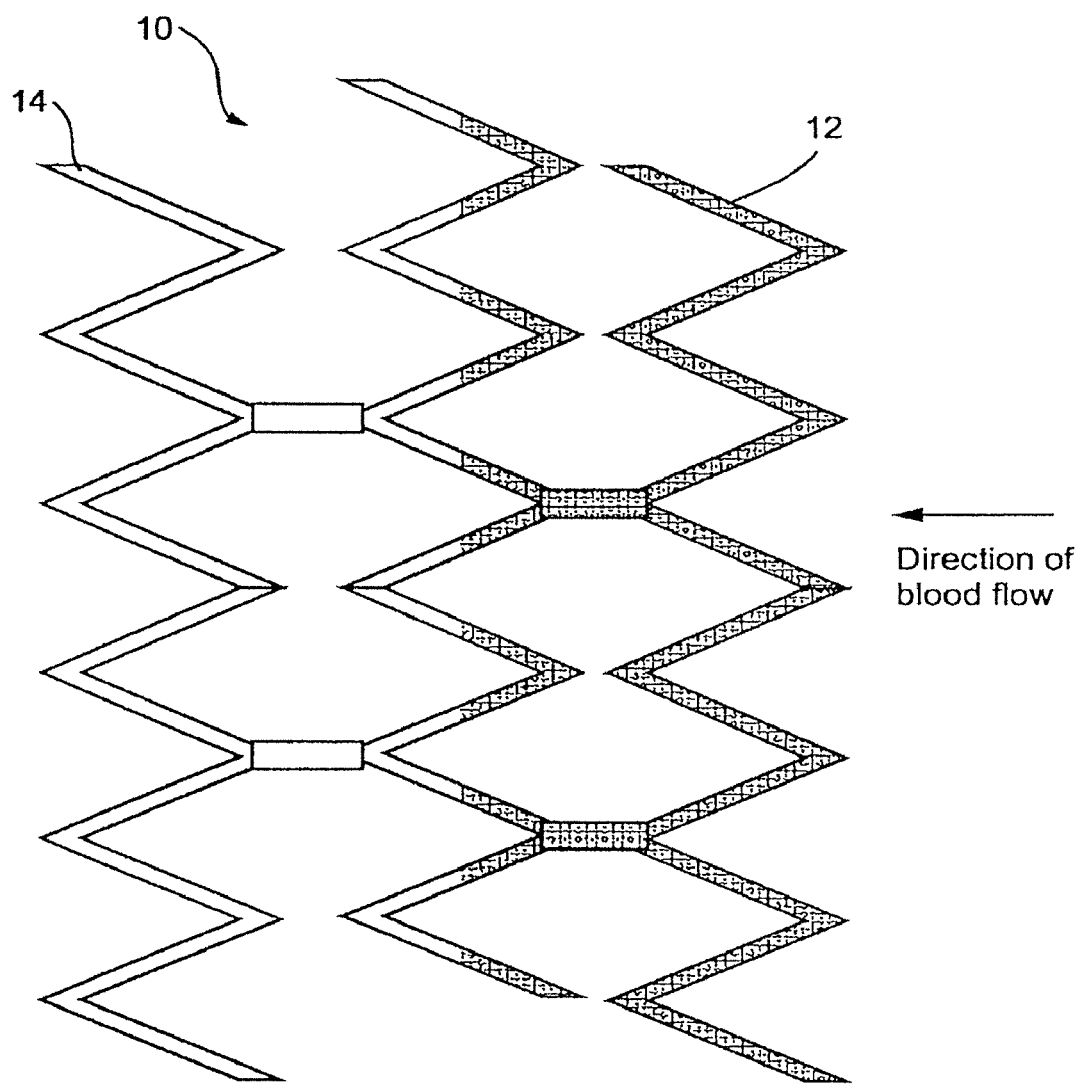
FIG. 2 is a schematic illustration of a stent, partially coated with an active metal, in accordance with another preferred embodiment of the present invention.

Referring further to the drawings, FIG. 2 is a schematic illustration of implant 10, formed as stent 10, formed of a platinum body 14, and partially coated with active metal 12, in accordance with a second preferred embodiment of the present invention. In this situation, the portion coated with active metal 12 acts as an anode while the portion formed of bare platinum body 14 acts as a cathode. In the presence of platinum, which acts as a catalyst, the corrosion reaction is considerably faster than that described in conjunction with FIG. 1. In accordance with the present embodiment, stent 10 is disposed with the cathode upstream of the anode, so that therapeutic compounds produced at the cathode, will migrate downstream with the blood, to effect therapy at the anode as well.

It will be appreciated that another biologically inert metal, operative as a catalyst, may be used for the cathode, in place of platinum. For example, palladium, iridium, nickel, a platinum-iridium alloy, or other alloys thereof may be used.

It will be appreciated that a biologically inert metal, which is a relatively poor catalyst, may still be used for the cathode, in place of platinum. For example, stainless steel, gold, or a gold alloy may be used. The use of a poor catalyst, such as stainless steel, will slow down the reaction, when compared to the use of platinum.

It will be appreciated that a biologically inert material, which is inoperative as a cathode, may still be used for the stent body, in place of platinum. For example, titanium, tantalum, alloys thereof, as well as various other materials such as a high-strength, high-resilience plastic may be used. The use of these materials will create a situation wherein active metal 12 is operative both as an anode and as a cathode, similar to the situation described in context of FIG. 1.

It will be appreciated that a combination of three or more materials may also be used in stent 10.

Figure 3:
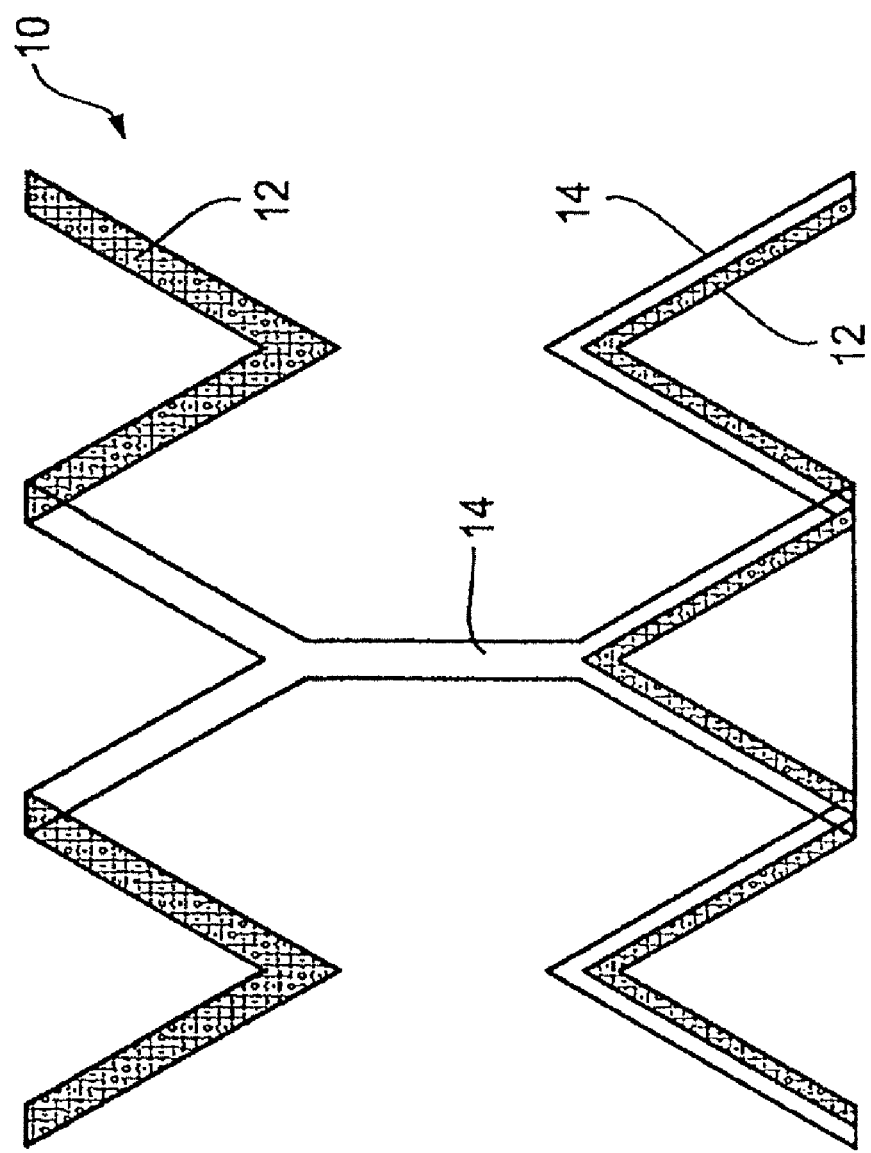
FIG. 3 is a schematic illustration of a stent, partially coated with an active metal, in accordance with another preferred embodiment of the present invention.

Referring further to the drawings, FIG. 3 is a schematic illustration of implant 10, formed as stent 10, formed of platinum body 14, and partially coated with active metal 12, in accordance with a third preferred embodiment of the present invention. In accordance with the present embodiment, the portions of bare platinum body 14 and active metal coating 12 are evenly distributed along stent 10. Alternating coating patterns may also be employed, generating a plurality of alternating cathodes and anodes. In these manners, the therapeutic compounds produced at the cathode generally reach all portions of stent 10, in a manner somewhat similar to that of FIG. 1.

The current density on the uncoated portions of the stent may not be uniform—it will be the highest in regions of contact between the coated and the uncoated portions, where the electrolytic path between the anodic and the cathodic sections of the surface is the shortest, which amounts to the lowest internal resistance of the local cells. A non-uniform current distribution may, in fact, be useful to create the highest concentration of therapeutic species, where restenosis is expected to be the most severe.

The total amount of zinc coated can be chosen to ensure that the electroless reduction occurs just as long as desired. The rate of corrosion of the zinc will depend on the location of the stent, the flow rate and the amount of oxygen in the blood, as well as on the nature of the metal of which the stent has been constructed.

It will be appreciated that with time, the situation of FIG. 1, hereinabove, will resemble that of FIG. 3, due to active metal depletion.

Figure 4:
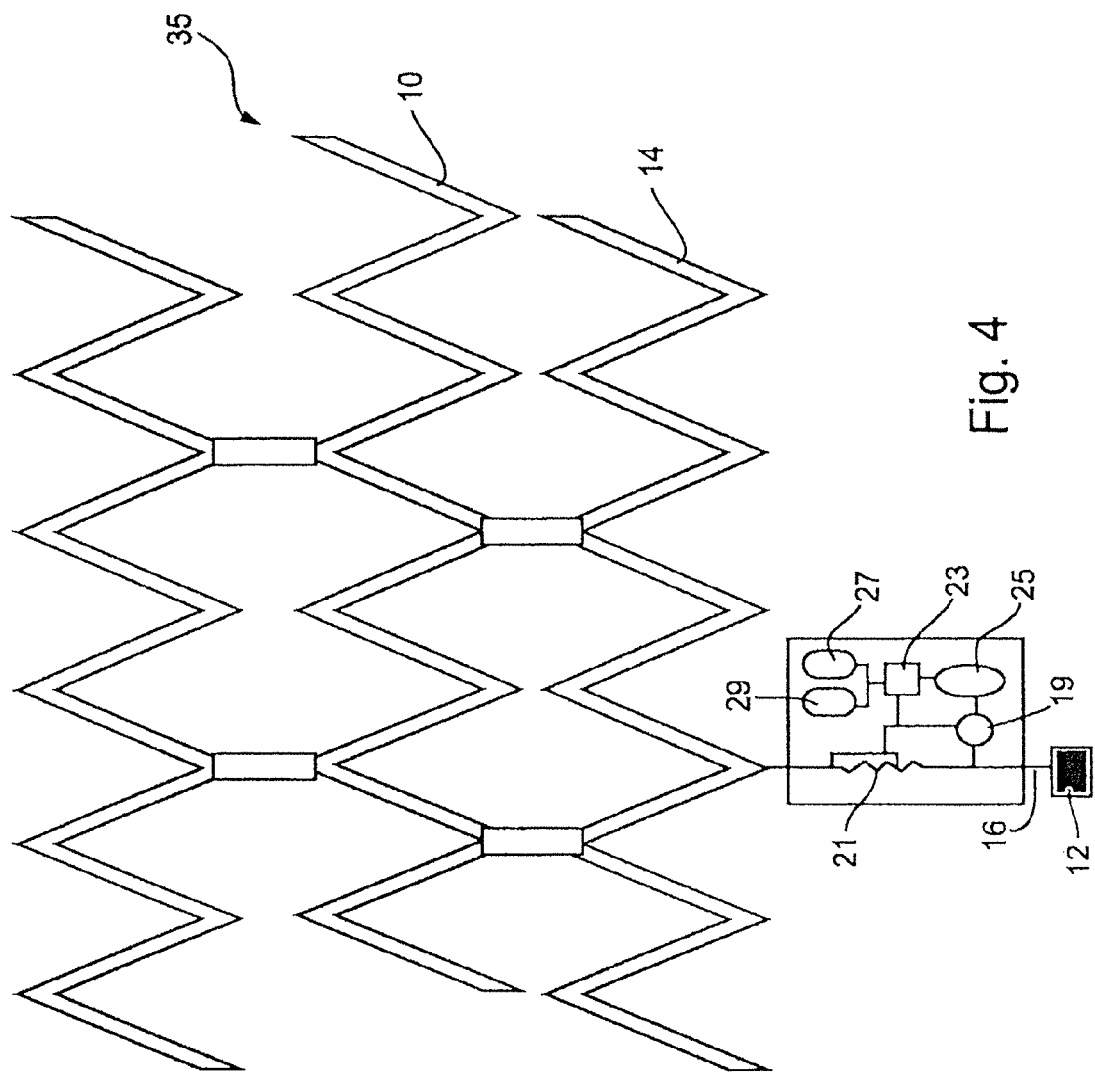
FIG. 4 is a schematic illustration of a stent, to which a strip of active metal is attached, in accordance with another preferred embodiment of the present invention.

Referring further to the drawings, FIG. 4 is a schematic illustration of an implant 35, which includes stent 10, formed of bare platinum body 14, in accordance with a fourth preferred embodiment of the present invention. Additionally, implant 35 includes a strip of active metal 12. An electronic conductor, such as a metal wire 16, connects active metal 12, forming the anode, and bare platinum body 14, forming the cathode.

There are several reasons for metal wire 16 of implant 35, as follows:

i. The anode and cathode may be implanted at different locations, for example, as will be described hereinbelow, in conjunction with FIGS. 6A and 6B.

ii. By providing an ammeter 19, or an equivalent thereof, in electrical communication with metal wire 16, the current through metal wire 16 may be measured, for providing an indication of the reaction rate.

iii. Additionally, by adding a variable resistor 21, controlled by a controller 23, wherein controller 23 is in signal communication with ammeter 19, and by adding a power source 25, one could control the current through metal wire 16, hence, the reaction rate, responsive to measurements of ammeter 19. Power source 25 may be, for example, a miniature battery. Miniature body implantable batteries are well known in the art. Such batteries are used, for example, for powering pace-makers and other devices and sensors implanted in the body.

iv. By adding a receiver 27 and a transmitter 29, in signal communication with controller 23, an extracorporeal station could receive signals, indicative of the reaction rate, as measured by ammeter 19, and transmit signals for varying the resistance of resistor 21, preferably responsive to the reaction rate signals.

v. By providing a telemetric energy transfer, battery 25 may be recharged. Telemetric energy transfer according to the present invention can be effected in any one of a plurality of ways known in the art, including radio frequency energy transfer, magnetic energy transfer and acoustic energy transfer.

Radio frequency energy transfer can be effected, for example, using an antenna coil and a rectifying circuit. Such circuits are well known and in common use in pacemakers and defibrillators, and therefore require no further description herein.

Magnetic energy transfer can be effected, for example, using a magnetic transducer which employs a magnet and a coil as is well known in the art. Examples of magnetic energy transfer are disclosed in, for example, U.S. Pat. Nos. 5,880,661, 6,185,457, 6,167,307, 6,164,284 and 6,162,238, which are incorporated herein by reference.

Acoustic energy transfer can be effected, for example, using an acoustic transducer as described, for example, in U.S. Pat. Nos. 6,140,740 and 6,170,488, which are incorporated herein by reference.

Telemetry can also be used, according to the present invention, to transmit data pertaining to the implant and (or) its effect from within the body outside thereof, for example as taught by U.S. Pat. No. 6,277,078, U.S. patent application Ser. No. 09/872,129, and U.S. patent application Ser. No. 09/690,615, whose disclosures are incorporated herein by reference.

Thus, implant 35 of the present invention may employ telemetry for accomplishing powering, control and/or communication of data. Different type telemetry can be employed for effecting each of these criteria.

In case telemetry is employed, an extracorporeal unit is provided, designed and constructed for powering, interrogating, controlling and/or receiving data from the implant.

Figure 5:
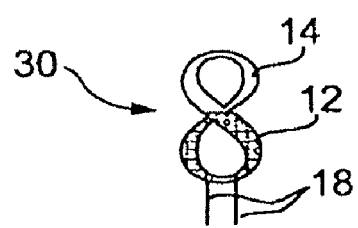
FIG. 5 is a schematic illustration of an anchor, partially coated with an active metal, in accordance with another preferred embodiment of the present invention.

Referring further to the drawings, FIG. 5 is a schematic illustration of an anchor 30, formed of platinum body 14, and partially coated with an active metal 12, in accordance with another preferred embodiment of the present invention. Anchor 30, which includes anchoring pins 18, or other means of anchorage, may be implanted in tissue other than the blood vessel, for example, in the brain, or within a cancerous tissue. When implanted in the brain, a brain fluid known as cerebrospinal fluid (CSF) is operative as the electrolyte for the electrochemical reaction. When implanted in cancerous tissue, or another tissue, the interstitial fluid is operative as the electrolyte for the electrochemical reaction. It will be appreciated that anchor 30 may be implanted also in the stomach, the intestines, and other body cavities and organs, such as the bladder cavity.

Figure 6A:
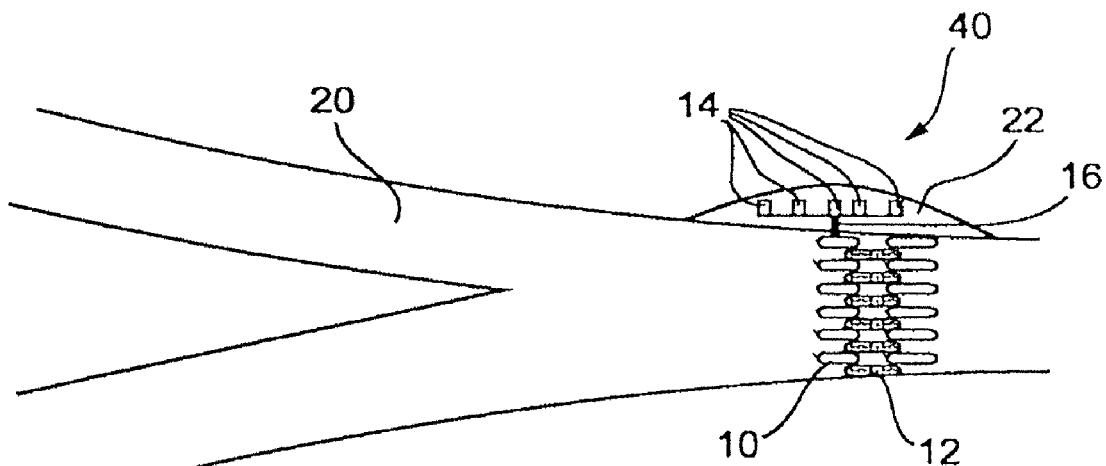
FIGS. 6A and 6B are schematic illustrations of an implant, adapted for cancer treatment, in accordance with another preferred embodiment of the present invention.
Figure 6B:
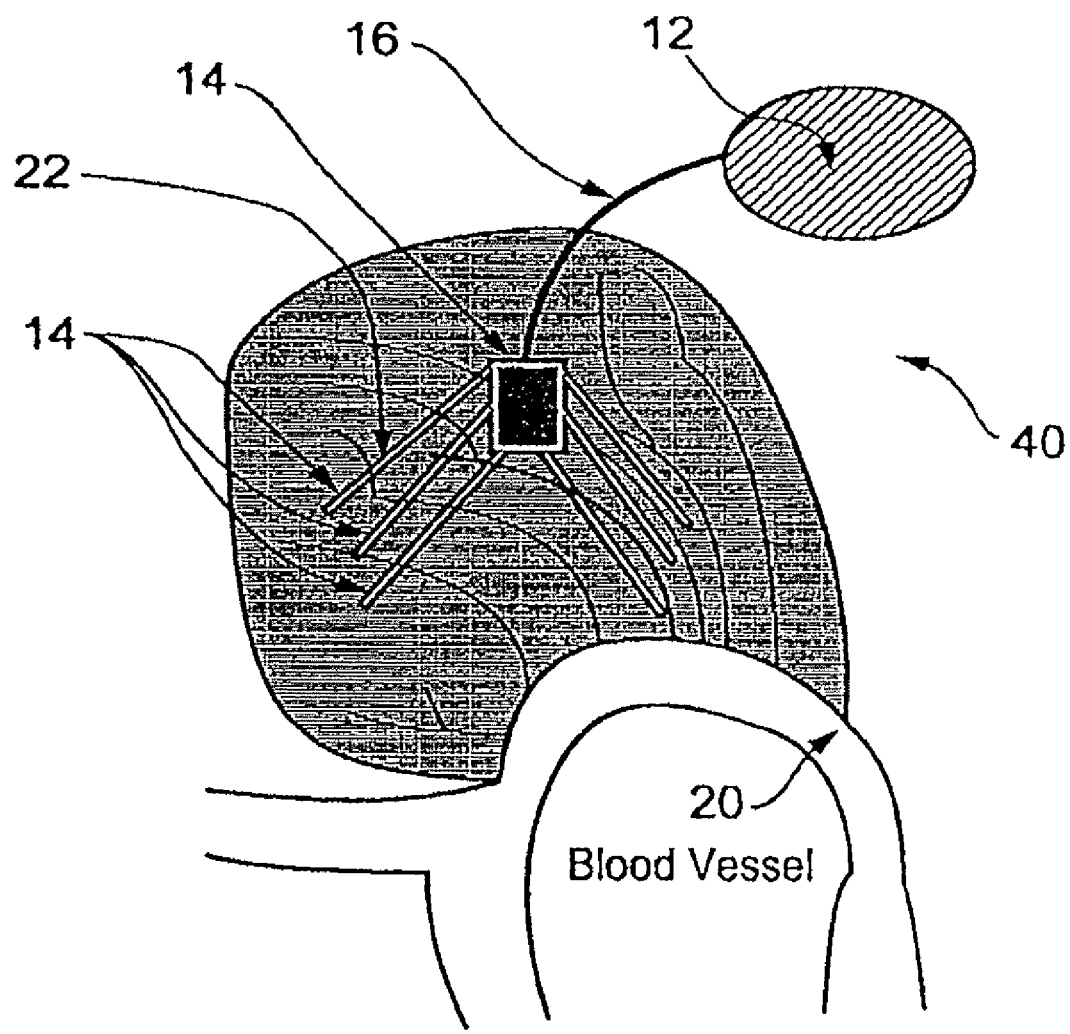

Referring further to the drawings, FIGS. 6A and 6B are schematic illustrations of implants 40, adapted for cancer treatment, in accordance with another preferred embodiment of the present invention. Preferably, implant 40 is formed of stent 10, fully coated with an active metal, and operative as an anode, adapted for implantation in a blood vessel 20 which feeds a tumor 22. At least one cathode, preferably formed of bare platinum 14, is implanted within tumor 22. Additionally, a plurality of cathodes of bare platinum 14, may be implanted, for a better distribution of the therapeutic compounds. Uniform production and concentration of the therapeutic compound in the tumor will ensure that all the tumor will be treated with minimal side effect on the healthy tissue and organ around it. The interstitial fluid is operative as the electrolyte for the electrochemical reaction, producing therapeutic agents within the tumor.

Referring further to the drawings, FIGS. 7A-7D are schematic illustrations of implantable vessels 50, in accordance with another preferred embodiment of the present invention. The problem of restenosis is not limited to stents, rather it is also characteristic of implantable vessels, including artificial or natural grafts such as by-pass grafts of veins or arteries, and shunts. Thus, an implantable vessel 50 includes a vessel body 51, defining a flexible tube. Body 51 may be an artificial body, made of an acceptable material such as ePTFE or Dacron.

However, vessel 50 may also be a natural blood vessel, obtained for, example from the lungs or the leg.

As seen in FIGS. 7A and 7B, body 51 includes a metal mesh 17, formed of bare platinum 14 wires, operative as cathodes, and zinc coated wires 12, operative as anodes.

Alternatively, as seen in FIGS. 7C-7C, body 51 includes a metal mesh 15, formed of bare platinum 14 wires, operative as cathodes. A zinc anode, may be located outside body 51, connected to cathodes 14 via wire 16.

It will be appreciated that a single zinc wire, or a pair of zinc and platinum wires, connected by a metal wire, or a stent, or a ring, fully or partly coated with zinc may also be used with the implantable vessel. It will be appreciated that other geometries are similarly possible.

It will be appreciated that another active metal, such as iron, may be used for the anode, and another inert metal may be used for the cathode, as has been described hereinabove.

Figure 8:
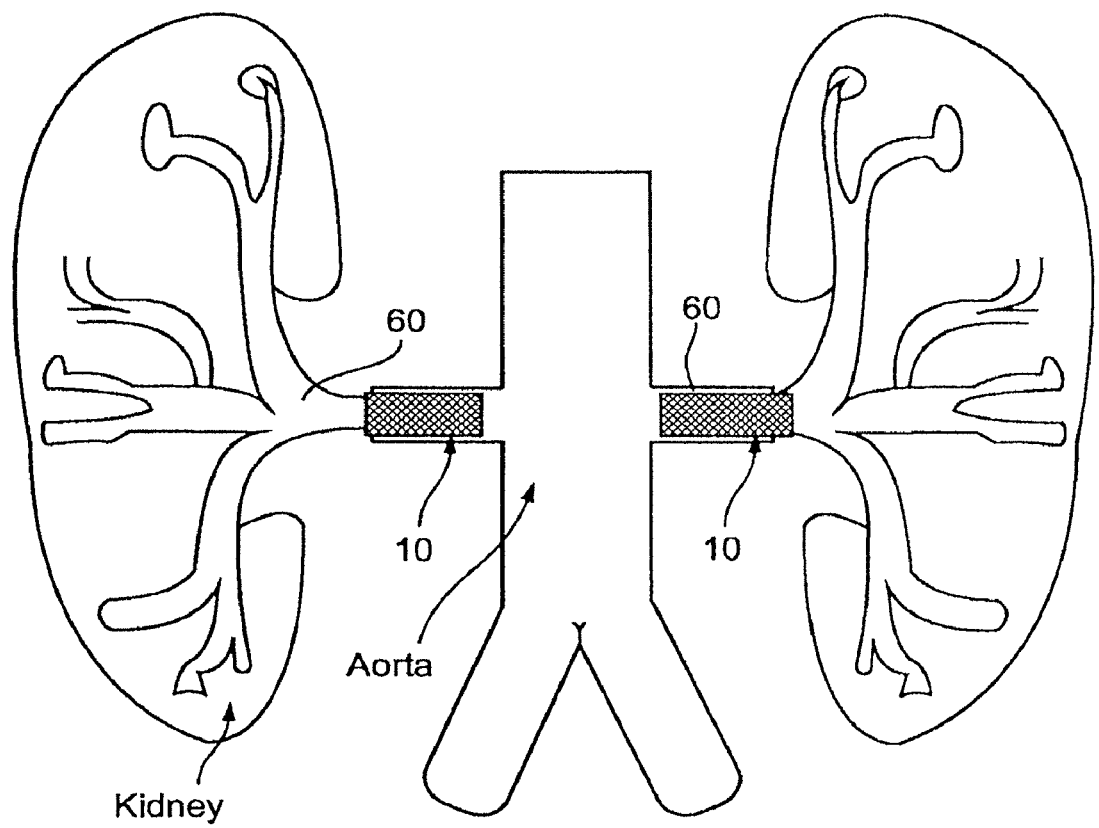
FIG. 8 is a schematic illustration of a stent, coated with an active metal, at the renal arteries, in accordance with the present invention.

Referring further to the drawings, FIG. 8 is a schematic illustration of a stent 10, coated with an active metal, at renal arteries 60, in accordance with the present invention.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non-limiting fashion.

Example 1

Open-Circuit Corrosion

When an active metal, such as zinc or iron, is placed in solution, it tends to corrode, by the anodic dissolution of the metal, for example, $$Zn \rightarrow Zn^{2+} + 2e^- \quad [1]$$

This process cannot continue for any significant length of time, without a suitable cathodic process, in which the electrons are consumed. In blood and other physiological fluids the typical pH is 7.4. Thus, the cathodic process may be described as:

$$O_2 + 2H_2O + 4e^- \rightarrow 4(OH)^- \quad [2]$$

The average potential measured vs. a suitable reference electrode will be somewhere between the reversible potentials for the anodic and the cathodic reactions. However, on the atomic scale, there will be sites on which the anodic reaction will take place and others on which the cathodic reaction will occur.

Zinc or iron are the preferred active metals for the present invention, because their reversible potentials are sufficiently negative and because they both exist naturally in blood and a small increase in their concentration is unlikely to be physiologically damaging or poisonous.

Example 2

Electroless In-Vivo Reduction of $NO_2^-$ and $NO_3^-$

The appropriate reactions for the anions of nitrous acid (the nitrate, $NO_3^-$) and nitric acid, (the nitrite, $NO_2^-$), and their reversible potentials in the blood and other body fluids, at pH=7.4, are given below.

$$NO_2^- + H_2O + e^- \rightarrow NO + 2(HO)^- \quad E = 0.329 \text{ V vs. SHE} \quad [3]$$

$$NO_3^- + 2H_2O + 3e^- \rightarrow NO + 4(HO)^- \quad E = 0.350 \text{ V vs. SHE} \quad [4]$$

If an active metal such as zinc or iron is attached to a stent and corrodes, as described in Equation [1], either one of the above reactions could take part in the corrosion process, as the cathodic reaction. In principle, Equations [3] and [4] may be considered single-step reduction processes, so that the electrochemical conversion is direct.

Oxygen reduction (Equation [2], as well as the equations of Example 3, hereinbelow) may also occur in parallel with Equations [3] and [4], so that the current efficiency for the reduction of the nitrogen-containing anion will probably be less than unity. This process may be called electroless in-vivo reduction.

Example 3

In-Vivo Electrochemical Production of Hydrogen Peroxide

Thermodynamically, oxygen reduction should lead to the formation of water. However, the high activation energy of the reaction makes it less favored, when compared with competing reactions, though thermodynamically unstable, as follows:

$$O_2 + 2H_2O + 2e^- \rightarrow H_2O_2 + 2(OH)^- \quad [5]$$

This reaction may then be followed by the reaction:

$$H_2O_2 + 2e^- \rightarrow 2(OH)^- \quad [6]$$

In this instance, one may consider the products of reaction [5] direct, while the product of reaction [6], the second-step reaction, indirect.

The following discussion analyzes and compares the thermodynamics and the kinetics of reaction [5] and [6], which lead to the presence of $H_2O_2$ in aquatious solutions, with those of alternative reactions, which may be thermodynamically stable, but kinetically very slow to proceed.

The other reaction that can take place and is relevant in the present context, although as pointed out, it is very slow, kinetically, is:

$$O_2 + 2H_2O + 4e^- \rightarrow 4(OH)^- \quad [7]$$

In addition, the following process, in which molecular hydrogen is formed, can occur at sufficiently negative potentials, but it is thermodynamically unfavored at a pH of 7.4, and in the presence of dissolved oxygen and other reducible materials, such as nitrite and nitrate ions:

$$2H_2O + 2e^- \rightarrow 2(OH)^- + H_2 \quad [8]$$

The corresponding standard reduction potentials at pH=0 and at the body pH of 7.4 are:

| Equation | Reaction | $E^0$ (volt SHE) at pH = 0 | $E^0$ (volt SHE) at pH = 7.4 |
|---|---|---|---|
| [9] | Reduction of $H_2O_2$ to $H_2O$ | 1.776 | 1.339 |
| [10] | Reduction of $O_2$ to $H_2O_2$ | 0.682 | 0.245 |
| [11] | Reduction of $O_2$ to $H_2O$ | 1.229 | 0.792 |
| [12] | Reduction of $H_2O$ to $H_2$ | 0.000 | −0.437 |

It follows from these data that hydrogen peroxide is not stable thermodynamically in water. To further demonstrate this, one may add reaction [6] with the reverse of reaction [5]:

$$H_2O_2 + 2e^- \rightarrow 2(OH)^- \quad E^0 = 1.339V \quad [6]$$

$$H_2O_2 \rightarrow O_2 2H^+ + 2e^- \quad E^0 = -0.245V \quad [\text{reverse of } 5]$$

$$2H_2O_2 \rightarrow O_2 + 2H_2O; \Delta E^0 = 1.094V \quad [13]$$

From thermodynamic considerations, the self-decomposition reaction of hydrogen peroxide (Equation [9]) is favored, since:

$$\Delta G^0 = -nF\Delta E^0 = -211 \text{ kJ/mole} \quad [14]$$

Specifically, is should not be possible to make and maintain an appreciable concentration of hydrogen peroxide in aqueous solution. At the positive electrode water is oxidized to hydrogen peroxide at 1.339 V (at pH=7.4), while hydrogen peroxide is oxidized to molecular oxygen at a much lower potential of 0.245 V. In other words, at the potential at which it is formed from water, $H_2O$, is highly unstable with respect to its further oxidation to $O_2$.

The relative stability of this compound in water is primarily due to the slow kinetics of its decomposition. This is not surprising, considering that during the reaction described in Equation [13], two H—O bonds are broken in one molecule and an O—O bond is broken in another. It also follows from Equation [13] that the rate of self-decomposition, which is a bi-homomolecular reaction, will decrease with dilution, as is well known experimentally.

Similarly, at the negative electrode, oxygen can be reduced to hydrogen peroxide at a potential of 0.245 V, where it is highly unstable towards further reduction to water, which can occur already at a potential of 1.339 V. This is a direct consequence of the thermodynamic instability of $H_2O_2$.

However, the kinetics of the different reactions plays a decisive role. In practice $O_2$ is reduced in two stages. A two-electron reduction step to $H_2O_2$ (Equation [5]) followed by another two-electron reduction step of the peroxide to $(OH)^-$ (Equation [6]). The slow kinetics of the second step (Equation [6]), or alternative step (Equation [7]) is not surprising. In Equation [5] two protons are attached to an oxygen molecule following charge transfer, but no bonds are broken. In Equations [6] and [7] the O—O bond must be broken. Indeed, one of the challenges facing the development of practical fuel cells is to develop efficient (and inexpensive) catalyst that can promote the reduction of oxygen to water and prevent its termination at the peroxide stage.

Hydrogen evolution (Equation [8]) can be a relatively fast reaction, comparable to or even faster than the reduction of $O_2$ to $H_2O_2$. However, its reversible potential is 0.682 V more negative. Therefore oxygen reduction to peroxide is found to occur first. The second reduction wave of oxygen (Equation [6]), associated with the reduction of $H_2O_2$ that is formed as an intermediate step, is at a high overpotential in the region of hydrogen evolution and can occur before, together with, or after the onset of hydrogen evolution.

In summary, the sequence of reactions occurring at the cathode in an aqueous solution containing oxygen is:

  [15]

If the current density applied is small and the concentration of oxygen in the solution is high enough, so that its concentration at the cathode surface is not significantly depleted, the first step, i.e., the production of $H_2O_2$ and the reduction of nitrite and nitrate to nitric oxide will probably be the main processes taking place at the cathode.

Example 4

Electrode Kinetic Considerations

Given an active metal, such as zinc, immersed in an electrolyte, operative as an anode, different second electrode selections and configurations will effect the reaction rate, as follows:

i. When no second electrode is provided, the anodic and the cathodic reactions occur on different parts of the active-metal surface, perhaps at locations very close to each other, but possibly further away, depending on the degree of inhomogeneity of the surface. This situation is illustrated in FIG. 1.

ii. When a second electrode, such as stainless steel, which is not a catalyst, is provided, for example, when a stent, formed of stainless steel, is partly coated with an active metal, the cathodic reaction may take place on the second electrode. However, the reaction rate will not be substantially affected by the presence of the second metal.

iii. When a second electrode, such as platinum, which is a known catalyst, is provided, for example, when a stent, formed of platinum, is partly coated with an active metal, with no electrical insulation between the two metals, the cathodic reaction will be preferential to the second electrode, and the reaction rate will greatly increase. This situation is illustrated in FIGS. 2 and 3.

iv. When a second electrode, whether operative as a catalyst or not (e.g., platinum or stainless steel) is provided, connected by an electronic conductor, such as a variable resistor, to the active metal, the reaction rate may be controlled, by controlling the rate of electron transfer between the cathode and the anode. This situation is illustrated in FIG. 4.

It will be appreciated that combinations of the above are possible.

It will be appreciated that the stent or anchor may be formed of inert materials that do not participate in the reactions and an anode, or an anode and a cathode, which may be further operative as a catalyst, may be attached to the stent or anchor.

Example 5

The Rate of Corrosion of an Active Metal in the Blood

The rate of the active metal corrosion determines the concentration of the electrochemical reaction products. The rate is controlled by the reversible potential of the metal at the given condition and by the reactant concentration (e.g., dissolved oxygen).

The following corrosion rate estimation is given for zinc, although other active metals can be used, such as iron.

The standard reversible potential for the $Zn^{+2}/Zn$ couple is −0.76 volts versus SHE (Standard Hydrogen Electrode). The reversible potential will depend on the concentration in the solution according to the Nernst equation. It is common, in considering corrosion problems, based on the Pourbaix's potential—pH diagrams, to assume that the concentration of the corrosion product ($Zn^{+2}$ in the present case) is 1 micro molar. The reversible potential will be:

$$E_{rev} = E_0 + (0.0295 RT) \log|Zn^{+2}| = -0.937 \text{ SHE} \quad [16]$$

The above is independent of pH. For the reduction of $O_2$ to $H_2O_2$ at pH=7.4, one has $E_{rev}$=0.68 V and for $NO_3^-$ $E_{rev}$=0.350 V.

As will be shown, the open circuit corrosion potential will be very close to the reversible potential for zinc, perhaps less than 50 mV anodic to it. At such a negative potential, the reduction of both oxygen and the nitrate ion will be almost equal to the rate of anodic dissolution of the metal.

The concentration of oxygen and nitrate in the blood are approximately 0.13 mM and 0.038 mM respectively. The diffusion coefficient of oxygen is $2 \times 10^{-5}$ cm$^2$/s. That of nitrate is probably somewhat lower, but since this ion is at a lower concentration, one can use the same value for both species as a good approximation.

The limiting current density will be given by:

$$i = \frac{FD(n_{O_2} C_{O_2} + n_{NO_3^-} C_{NO_3^-})}{\delta}. \quad [17]$$

The Nernst diffusion-layer thickness, $\delta$, depends on many factors, including the rate of flow of the blood and the accumulative deposition of cells or any other substance, such as blood proteins that may cover the surface. A value of 0.01 cm is a good estimate for a bare surface. Using this value yields:

$$i = \frac{96.485 \cdot 10^3 \times 2 \cdot 10^{-5} \times (2 \times 1.3 \cdot 10^{-7} + 3 \times 0.38 \cdot 10^{-7})}{1 \cdot 10^{-2}} = 72.2 \cdot 10^{-6} A/cm^2 \quad [18]$$

Converting this rate into mg/cm$^2$sec results in:

$$72 \mu A/cm^2 = \frac{72 \cdot 10^{-6}}{96.485 \cdot 10^3} \times 32.7 \quad [19]$$
$$= 24.4 \cdot 10^{-9} gr/cm^2 sec$$

This value corresponds to a rate of about 2.1 mg/cm$^2$ in a 24 hour period.

Note that this is only a gross estimation. The actual rate of zinc dissolution will be probably lower than the calculated value. The reasons for that are twofold. First, the diffusion coefficient in blood is lower than the values based on diffusion in diluted aqueous solution. Second, cells, platelets and proteins may cover metallic surfaces, resulting in a reduction of the reactants (oxygen and nitrate) flow rate and (or) their diffusion rate.

Example 6

An Estimate of the Concentration of No Produced at the Surface of the Stent

The total rate of corrosion, according to Equation [18], is $72.2 \times 10^{-6}$ A/cm$^2$. Assuming that all of this current is consumed in the 1-electron reduction of $NO_2^-$ to NO, the rate of production of NO will be:

$$\frac{72.2 \times 10^{-6}}{96.5 \times 10^3} = 0.76 \times 10^{-9} \text{mole/s} = 22.6 \times 10^{-9} \text{g/s} \quad [20]$$

The diffuse double layer thickness at the surface is given by:

$$\delta = \sqrt{\pi D t} \quad [21]$$

Using the values of $D=2\times10^{-5}$ cm$^2$/s and t=1 sec, one gets, $\delta=8\times10^{-3}$ cm, hence the average concentration of NO in the surface layer will be:

$$22.6\times10^{-9}/8\times10^{-3} = 2.86 \text{ ppm} \quad [22]$$

Note that if the source of NO will be the nitrate ion $NO_3^-$, the above number will be divided by three, since three electrons are needed to reduce each nitrate ion to NO, while only one electron is needed to reduce a nitrite ion to NO.

Example 7

Zinc-Coated Coronary Stent

Taking a typical coronary stent 15 mm long expanded to 3 mm diameter with a metal coverage percentage of 15%. This stent has a metallic surface area of:

$$S_{stent} = \pi \cdot D \cdot L \cdot 2 \cdot 0.15 = 0.424 \text{ cm}^2 \quad [23]$$

where:
$S_{stent}$ is the stent internal and external surfaces;
D is the stent diameter; and
L is the stent length.

The rate of zinc dissolution from the surface of such a device (assuming a corrosion rate calculated in Equation [19]) results in:

$$\text{Rate} = (24.4\times10^{-9} \text{ gr/cm}^2\text{s}) \times (0.424 \text{ cm}^2 = 1.0\times10^{-8} \text{ gr/s} \quad [24]$$

Assuming that the stent will be coated with 40 μm of zinc (density=7.14 gr/cc) resulting in a total of:

$$W_{Zn} = 0.424 \times 40 \times 10^{-4} \text{cm}^3 \times 7.14 \text{gr/cm}^3 = 12 \text{mg} \quad [25]$$
$$\Downarrow$$
$$T_{corrosion} = 12 \cdot 10^{-3} / 1.0 \cdot 10^{-8} \text{s} = 1.2 \cdot 10^6 s \approx 14 \text{days}$$

$$\text{Corrosion rate} = 1 \times 10^{-8} \text{gm/s} = 8.6 \times 10^{-4} \text{gm/d} \approx 1 \text{mg/d} \quad [26]$$

It will be appreciated in this context that by selecting the amount of active metal, one can control the time by which electrode depletion will result is cessation of the reactions.

Example 8

Biological Effect of the Dissolved Metal

Zinc is an essential element in our diet. Too little zinc can cause health to problems, but too much zinc is also harmful.

Based on the Agency for Toxic Substances and Disease Registry (ATSDR). 1994, Toxicological profile for zinc, (Atlanta, Ga.: U.S. Department of Health and Human Services, Public Health Service), the recommended dietary allowance (RDA) for zinc is 15 milligrams a day for men; 12 mg/day for women; 10 mg/day for children; and 5 mg/day for infants. Insufficient zinc in one's diet can result in a loss of appetite, a decreased sense of taste and smell, slow wound healing and skin sores, a damaged immune system, poorly developed sex organs, in men and growth retardation of fetuses.

Too much zinc, however, can also be damaging to one's health. Harmful health effects generally begin at levels from 10-15 times the RDA (in the 100 to 250 mg/day range). As can be appreciated the zinc amount released by the implant is far lower than these levels. Thus, a systemic or a local damage due to a high zinc level is highly improbable.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub combination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A stent adapted to be implanted in a blood vessel comprising:
 a stent body comprising a biologically inert metal selected from the group consisting of platinum, palladium, iridium, gold, and alloys thereof; and
 a coating of an active metal adapted to corrode when implanted in the blood vessel, the active metal comprising zinc or iron, wherein one or more portions of the stent body are uncoated to allow for direct exposure of the one or more portions of the stent body to body fluid when the stent is implanted within a body lumen, wherein the coating is upstream or downstream of at least one uncoated portion.

2. The stent of claim 1, wherein the active metal comprises zinc.

3. The stent of claim 1, wherein the active metal comprises iron.

4. The stent of claim 1, wherein the biologically inert metal comprises platinum.

5. The stent of claim 1, wherein the biologically inert metal comprises palladium.

6. The stent of claim 1, wherein the biologically inert metal comprises gold.

7. The stent of claim 1, wherein the active metal acts as an anode and the biologically inert metal acts as a cathode when the stent is implanted within a blood vessel.

8. The stent of claim 7, wherein the active metal and the biologically inert metal are both directly exposed to the flow of body fluid in a blood vessel when the stent is implanted in a blood vessel.

9. The stent of claim 1, wherein the stent comprises a body of the biologically inert metal and a coating of the active metal.

10. The stent of claim 9, wherein the coating of the active metal is a partial coating such that the active metal acts as an anode and uncoated portions of the body act as a cathode.

11. The stent of claim 10, wherein the uncoated portions of the body are upstream of the coated portions of the body.

12. The stent of claim 1, wherein the active metal is adapted to electrochemically convert, in a body fluid stream environment, at least one substance present in the body fluid into a therapeutic agent.

13. The stent of claim 12, wherein the at least one substance is a normal body fluid constituent.

14. The stent of claim 13, wherein the normal body fluid constituent is selected from the group consisting of water, moledular oxygen, nitrite and nitrite ions and L-arginine.

15. The stent of claim 12, wherein the at least one substance is a substance administered to the body.

16. The stent of claim 15, wherein the at least one substance is selected from the group consisting of nitrite ions, nitrate ions, and a combination thereof.

17. The stent of claim 12, wherein the therapeutic agent is an oxidizing agent.

18. The stent of claim 12, wherein the therapeutic agent is the vasodilating agent, nitric oxide.

19. A stent adapted to be implanted in a blood vessel comprising:
- a stent body comprising a biologically inert metal selected from the group consisting of palladium and alloys thereof; and
- a coating of an active metal adapted to corrode when implanted in the blood vessel, the active metal comprising iron, wherein one or more portions of the stent body are uncoated to allow for direct exposure of the one or more portions of the stent body to body fluid when the stent is implanted within a body lumen, wherein the coating is upstream or downstream of at least one uncoated portion.

* * * * *

UNITED STATES PATENT AND TRADEMARK OFFICE
CERTIFICATE OF CORRECTION

PATENT NO.        : 8,303,643 B2
APPLICATION NO.   : 12/784708
DATED             : November 6, 2012
INVENTOR(S)       : Avi Penner and Eilezer Gileadi It is certified that error appears in the above-identified patent and that said Letters Patent is hereby corrected as shown below:

1) Column 19, Claim 14, Line 9: delete "moledular" and insert --molecular--.

Signed and Sealed this
Fifth Day of February, 2013

Teresa Stanek Rea
*Acting Director of the United States Patent and Trademark Office*